(12) United States Patent
Karami

(10) Patent No.: US 7,621,901 B2
(45) Date of Patent: Nov. 24, 2009

(54) DISPOSABLE PANT TYPE ABSORBENT ARTICLE HAVING IMPROVED MULTIFOLD FASTENING SYSTEM AND METHOD OF MAKING SAME

(75) Inventor: Hamzeh Karami, Lockhaven, PA (US)

(73) Assignee: First Quality Products, Inc., Great Neck, NY (US)

( * ) Notice: Subject to any disclaimer, the term of this patent is extended or adjusted under 35 U.S.C. 154(b) by 667 days.

(21) Appl. No.: 10/646,937

(22) Filed: Aug. 22, 2003

(65) Prior Publication Data

US 2004/0039364 A1 Feb. 26, 2004

Related U.S. Application Data

(63) Continuation-in-part of application No. 10/442,913, filed on May 21, 2003, now abandoned, which is a continuation-in-part of application No. 10/346,607, filed on Jan. 17, 2003, now abandoned, which is a continuation-in-part of application No. 10/329,889, filed on Dec. 26, 2002, now abandoned, which is a continuation-in-part of application No. 10/266,420, filed on Oct. 8, 2002, now abandoned, which is a continuation-in-part of application No. 09/965,381, filed on Sep. 27, 2001, now Pat. No. 6,752,796, which is a continuation-in-part of application No. 09/844,726, filed on Apr. 27, 2001, now abandoned, which is a continuation-in-part of application No. 09/797,334, filed on Mar. 1, 2001, now abandoned, which is a continuation-in-part of application No. 09/247,629, filed on Feb. 10, 1999, now abandoned.

(51) Int. Cl.
*A61F 13/15* (2006.01)

(52) U.S. Cl. .............. 604/386; 389/385.28; 389/385.27; 389/391; 389/387

(58) Field of Classification Search .................. 604/386, 604/389, 390, 391, 385.01, 385.03, 387, 604/385.28, 385.27
See application file for complete search history.

(56) References Cited

U.S. PATENT DOCUMENTS

| | | | | |
|---|---|---|---|---|
| 3,724,464 | A | * | 4/1973 | Enloe .......................... 604/365 |
| 3,931,666 | A | * | 1/1976 | Karami ......................... 24/304 |
| 3,999,544 | A | * | 12/1976 | Feldman et al. ............. 604/390 |

(Continued)

FOREIGN PATENT DOCUMENTS

| | | |
|---|---|---|
| EP | 0 528 282 A2 | 2/1993 |
| EP | 1 077 054 A2 | 2/2001 |
| GB | 2 267 024 A | 11/1993 |
| WO | WO 00/35396 | 6/2000 |
| WO | WO 00/74621 A1 | 12/2000 |
| WO | WO 02/41816 A2 | 5/2002 |

OTHER PUBLICATIONS

European Search Report from Application No. EP 02 02 1771, dated Sep. 20, 2007.

*Primary Examiner*—Jacqueline F. Stephens
(74) *Attorney, Agent, or Firm*—Amster, Rothstein & Ebenstein LLP

(57) ABSTRACT

An absorbent article is provided having a back waist portion with a fibrous outer surface and two lateral ends, a front waist portion with a fibrous outer surface and two lateral ends adjacent the lateral ends of the back waist portion, two prefolded nonwoven connectors each connecting two adjacent ends of the back waist portion and the front waist portion, and a hook fastener prefastened to one of said nonwoven connectors such that the prefastened hook is pre-engaged with the outer fibrous surface of the front waist region. Each nonwoven connector may be folded n times wherein n is an integer of front 2 to 30. The front and back lateral edges may be folded over the top surface of said article, and secured in place by a securement means.

8 Claims, 41 Drawing Sheets

U.S. PATENT DOCUMENTS

| | | | |
|---|---|---|---|
| 4,938,753 A | 7/1990 | Van Gompel et al. | |
| 5,053,028 A * | 10/1991 | Zoia et al. | 604/385.21 |
| 5,326,612 A | 7/1994 | Goulait | |
| 5,407,439 A | 4/1995 | Goulait | |
| 5,496,298 A | 3/1996 | Kuepper et al. | |
| 5,624,428 A * | 4/1997 | Sauer | 604/391 |
| 5,830,206 A | 11/1998 | Larsson | |
| 5,843,068 A | 12/1998 | Allen et al. | |
| 5,858,515 A | 1/1999 | Stokes et al. | |
| 5,885,574 A | 3/1999 | Elliott | |
| 5,968,030 A * | 10/1999 | Shimizu et al. | 604/390 |
| 6,007,527 A * | 12/1999 | Kawaguchi et al. | 604/386 |
| 6,027,484 A | 2/2000 | Romare | |
| 6,036,805 A | 3/2000 | McNichols | |
| 6,086,571 A | 7/2000 | Guevara et al. | |
| 6,287,287 B1 | 9/2001 | Elsberg | |
| 6,447,497 B1 | 9/2002 | Olson | |
| 6,454,752 B1 | 9/2002 | Huang et al. | |
| 6,461,344 B1 | 10/2002 | Widlund et al. | |
| 6,579,275 B1 | 6/2003 | Pozniak et al. | |
| 6,667,085 B1 | 12/2003 | McNichols | |

* cited by examiner

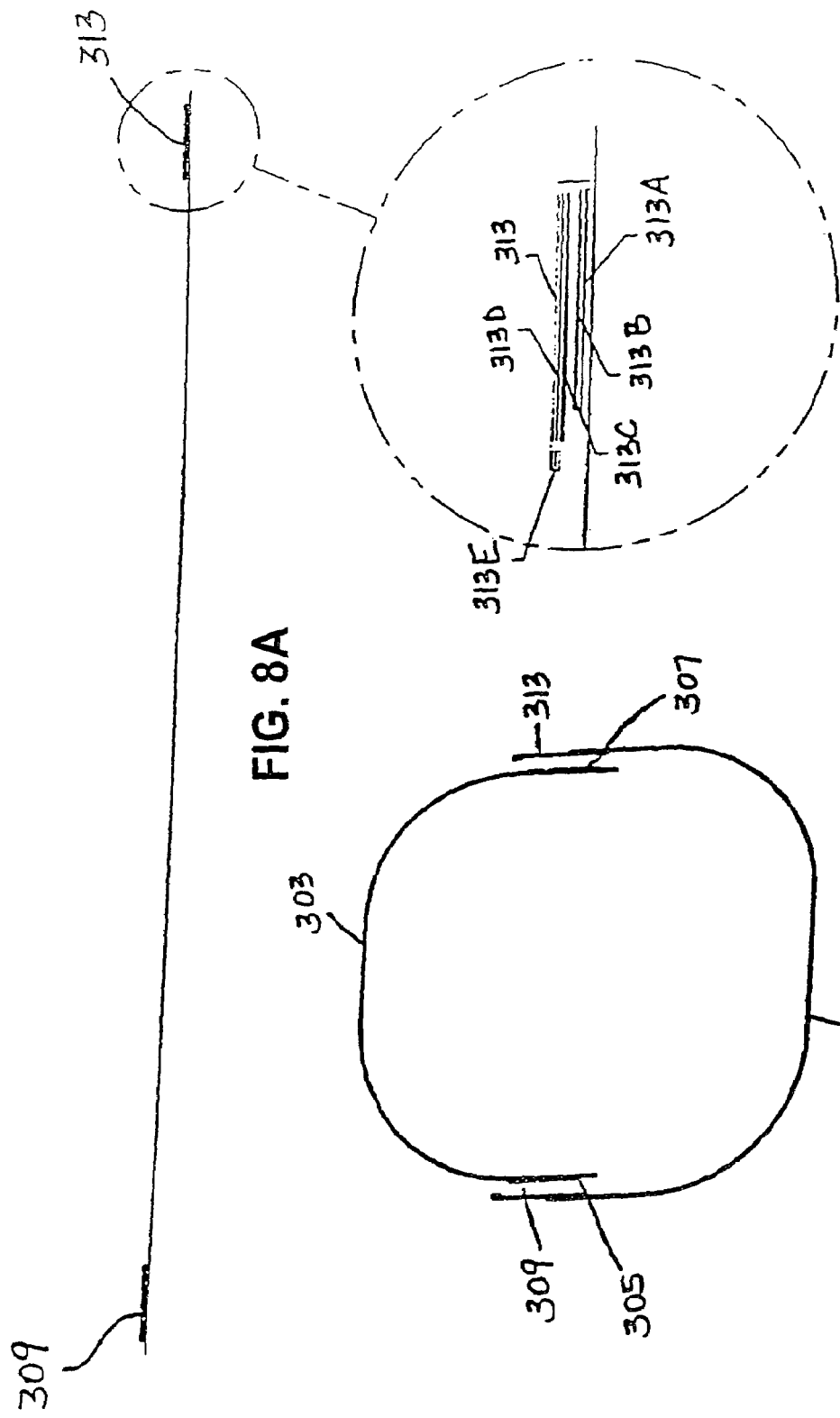

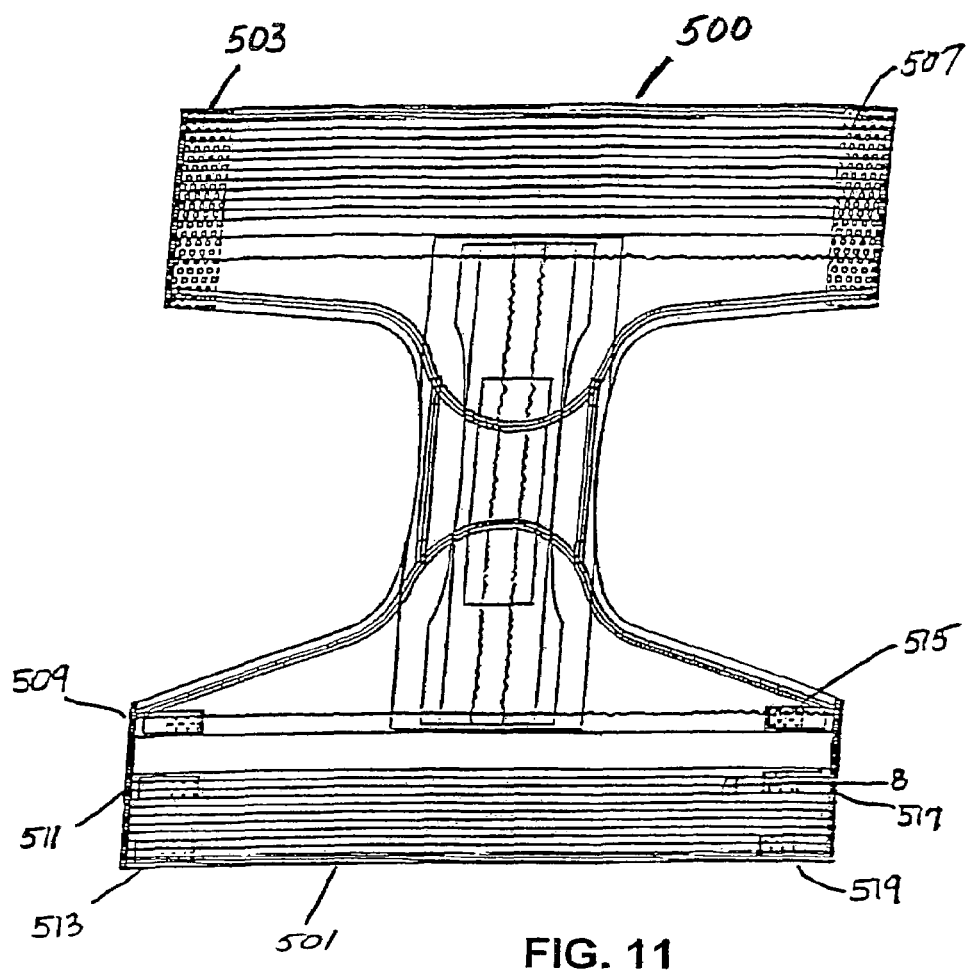
FIG. 11
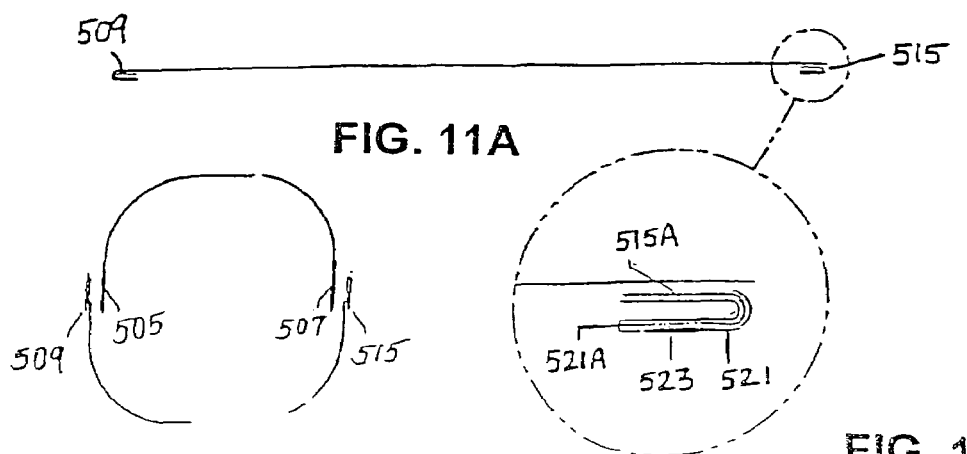
FIG. 11A
FIG. 11C
FIG. 11B

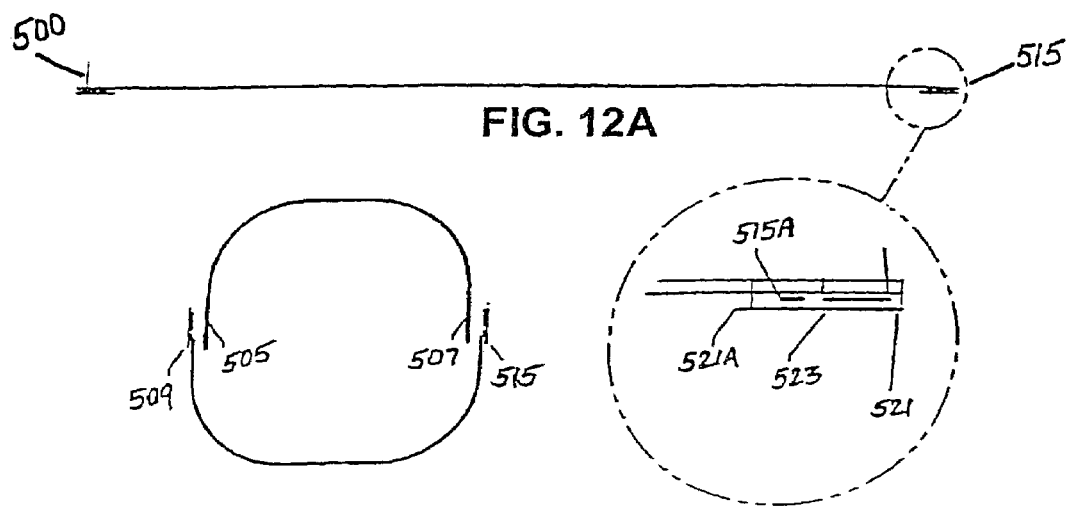

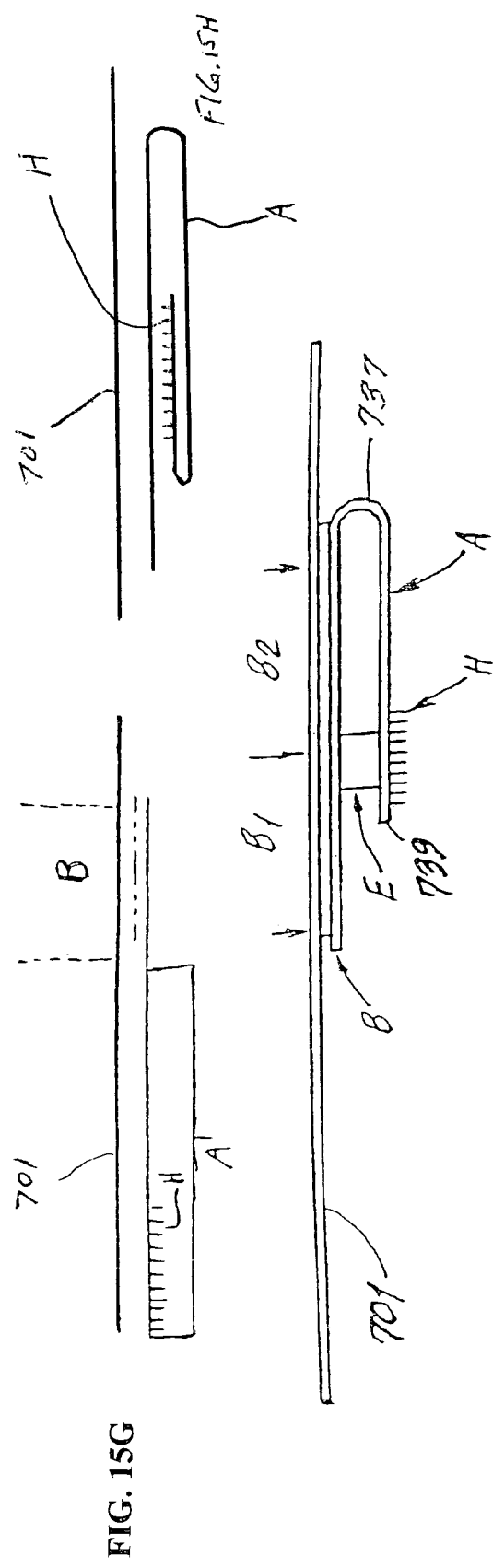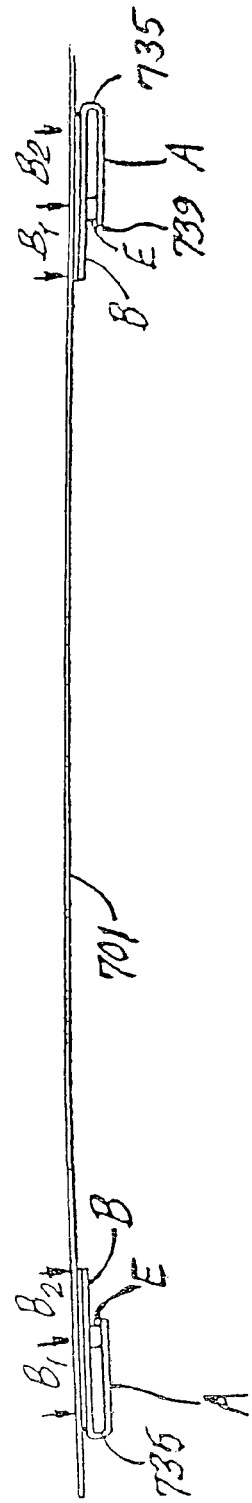
FIG. 15G
FIG. 15
FIG. 16

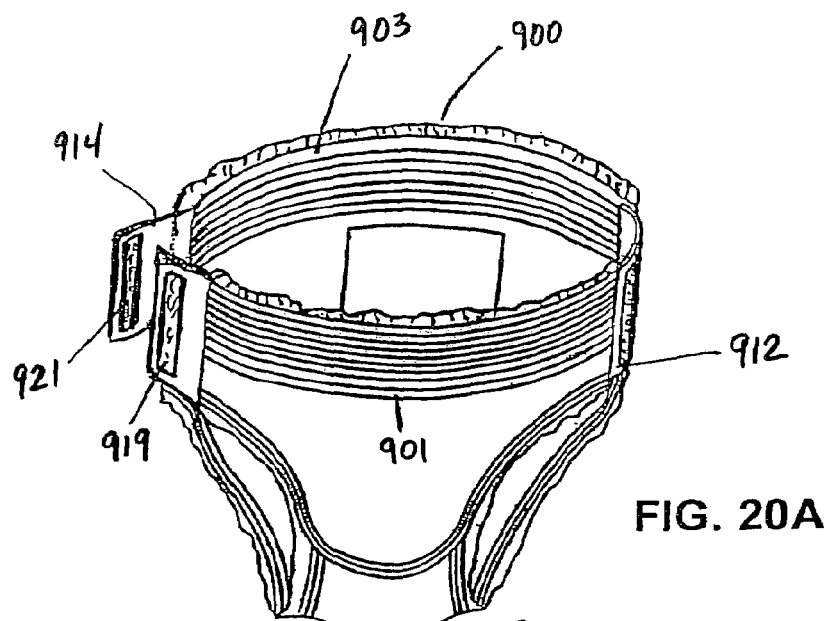
FIG. 20A
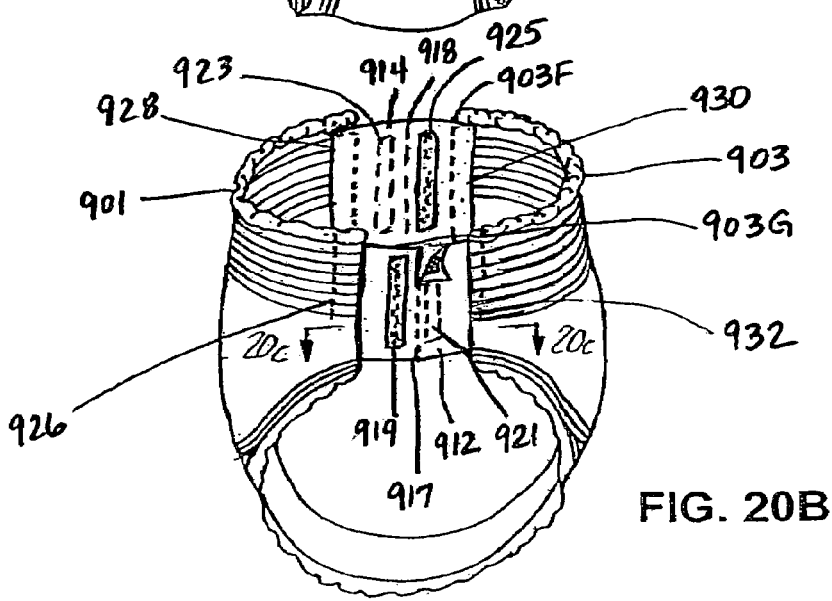
FIG. 20B
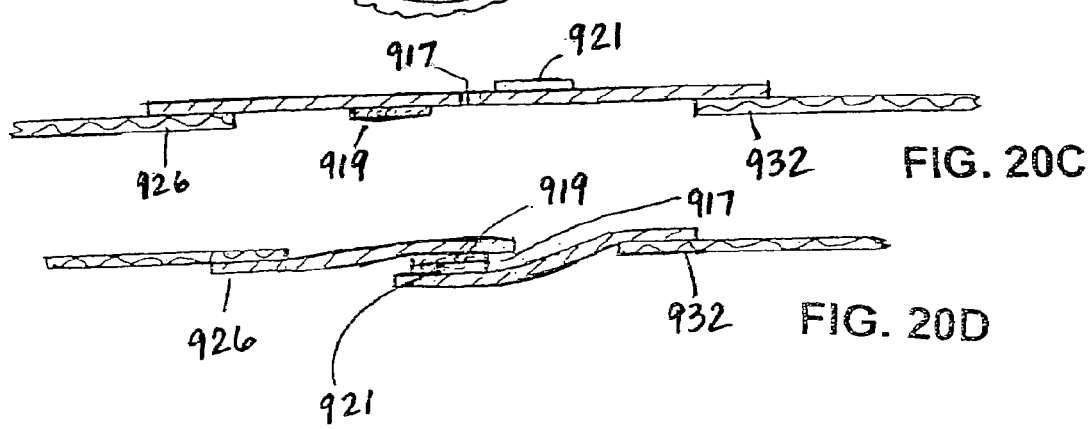
FIG. 20C
FIG. 20D

1112

DISPOSABLE PANT TYPE ABSORBENT ARTICLE HAVING IMPROVED MULTIFOLD FASTENING SYSTEM AND METHOD OF MAKING SAME

RELATED APPLICATIONS

This application is a continuation in part of commonly assigned, copending application Ser. No. 10/442,913 filed May 21, 2003, now abandoned which is a continuation-in-part of application Ser. No. 10/346,607 filed Jan. 17, 2003 now abandoned which is a continuation-in-part of application Ser. No. 10/329,889 filed Dec. 26, 2002 now abandoned which is a continuation-in-part of application Ser. No. 10/266,420 filed Oct. 8, 2002, now abandoned which is a continuation-in-part of application Ser. No. 09/965,381 filed Sep. 27, 2001, now abandoned which is: (1) a continuation-in-part of application Ser. No. 09/844,726 filed Apr. 27, 2001, now abandoned which is, a continuation-in-part of application Ser. No. 09/797,334 filed Mar. 1, 2001, now abandoned: and (2) a continuation-in-part of application Ser. No. 09/247,629 filed Feb. 10, 1999 now abandoned.

FIELD OF THE INVENTION

The present invention relates generally to disposable absorbent articles such as training pants (e.g., pull-ups and pull-ons), diapers, undergarments, T-shaped articles and briefs. In one aspect, the present invention relates to an absorbent article of the aforementioned types which, due to its unique construction and improved fasteners, assures fitness and comfort to the wearer, protects against leakage of fluids and other body exudates and which can be readily opened for inspection and removal by the wearer.

BACKGROUND OF THE INVENTION

Disposable absorbent articles such as disposable baby diapers and adult incontinent briefs, underpants, guards and the like articles are widely used in homes and in various health care facilities and institutions. Indeed the use of such articles has become a common sanitary practice, and while initially such absorbent articles were used mostly for infant care, more recently their use has been expanded to include adults as well. In both instances, the absorbent article must be designed to effectively prevent leakage of urine and other fecal materials, while insuring body fit and comfort.

Most presently available absorbent articles are generally unitary in structure, pre-shaped and pre-folded, and comprise an absorbent pad having a liquid permeable top sheet facing the wearer's body, a liquid impermeable backsheet on the opposite side, and an absorbent sheet or panel disposed between the top sheet and the back sheet. The absorbent article comprises a front side portion, a crotch portion and a backside portion, and further includes elastic members along the circumference of the waist and around the leg openings. While the heretofore commercially available absorbent articles have been somewhat effective against leakage of body fluids and fecal materials, and have therefore met some degree of acceptability, they have not been entirely satisfactory for their intended applications. In other words, they have not proven to be entirely leak proof, nor have they completely prevented issuance of the body exudates outside the diaper or the underpants. These deficiencies are primarily due to inadequate and loose body fit, which result in leakage of the body fluids and solids through the legs' openings. These problems are even more pronounced in case of adults because of their diverse body shapes and varying contours. Another disadvantage of the commercially available absorbent articles such as diapers, incontinent briefs and the like, is associated with opening and removing the soiled article for inspection without soiling the wearer's leg or body, or changing the diaper while the wearer has his or her shoes and pants on.

There are several patents which disclose various attempts made in the prior art over the past years to eliminate, or at least minimize, the shortcomings of the present commercially available absorbent briefs. Some of these patents are referred to in the aforementioned commonly assigned, copending application Ser. No. 09/965,381, filed Sep. 27, 2001. That patent application describes a pull-up diaper comprising a coversheet, a backsheet, an absorbent layer disposed between the coversheet and the backsheet, a front waist region, a back waist region, a crotch region and a pair of leg openings through which extends the legs of the wearer of the diaper. The front and back waist regions are provided with fasteners for fastening the two regions together. In one embodiment, the fastening system comprises a pair of loop strips located at the lateral edges of the front waist region and a pair of correspondingly aligned hook strips located at the lateral edges of the back waist region such that when the back waist region and the front waist region are overlapped during wear, each hook strip releasably engages a correspondingly aligned loop strip. Other fastening systems are disclosed and in one variation the back waist region comprises one or more tape tabs located at its lateral edges. Each tab has one surface attached to the back waist region and an opposed hook surface aligned with a loop strip in the waist region. In order to fasten the diaper such as during wear, the back waist region and the front waist region are overlapped so as to engage the hook surface of each tab with a correspondingly aligned loop strip on the front waist region.

In a recent patent, i.e., U.S. Pat. No. 6,027,484 issued Feb. 22, 2000 to Anette Remare, a pant diaper is described comprising a piece of fibrous nonwoven or plastic elastic material 9 having two parts 13 and 14 which can be pulled apart to define the side parts or flaps of the diaper. The side parts are fastened together by means of the hooks 15,16 and the loop 17 as shown in FIGS. 1 and 2. The piece 9 is joined to the outer casing 3 of the front part of the diaper by the glue points 10 which may be homogeneously distributed as shown in FIG. 1 or non-homogenous glue points or fastening means 110 as shown in FIG. 3.

A more recent patent, i.e., U.S. Pat. No. 6,287,287 B1 issued Sep. 11, 2002 to Laura Linda Elsberg describes a prefastened disposable article which includes a pair of primary fasteners located on opposed side edges of one waist region. The primary fasteners overlap and releasably engage the opposite waist region. A pair of passive bonds releasably connect the overlapped portion of one waist portion to the opposite waist region in order to maintain the article in prefastened condition.

In general, the pull-up diapers described in the prior art patents have a common structural deficiency in that they are provided with side seams which are welded together by heat and pressure or vibration (ultrasonic welding). Side seals must be sufficiently strong to hold the diaper on the person and must be capable of being torn so that the wearer can tear it easily in order to inspect or change the diaper while having his or her shoes on. Diapers having hook and loop fastening systems as described in the aforementioned copending application Ser. No. 09/965,381 provide improvements over the prior art diaper, but nevertheless there is still a need for pull up type absorbent articles and other diapers which are comfortable to wear, highly effective against leakage of fluids and feces, can be readily inspected for soil and which a have compact fastener that is folded in place when the diaper is not being used.

Accordingly, it is an object of the present invention to provide an absorbent article such as infant diapers, adult incontinent briefs, underpants, conventional diapers, pull-up and T-shaped diapers, and other like articles, which overcome the deficiencies and shortcomings of the prior art absorbent articles.

It is another object of this invention to provide disposable absorbent articles which, due to their unique construction, provide improved fit to the body and prevent leakage of urine and other body exudates through the leg openings, and which are easy to take apart for soil inspection.

It is also an object of this invention to provide such disposable absorbent articles which utilizes a unique multifold hook and loop fastening system in order to assure leakage prevention, simplify opening, inspection and reassembling of the diaper after inspection, and which is comfortable to wear by incontinent persons.

The foregoing and other objects and features of the present invention will be more fully comprehended and appreciated from the ensuing detailed description and drawings which form parts of this application.

SUMMARY OF THE INVENTION

In order to achieve the foregoing objects and desirable features, the present invention provides a disposable absorbent article such as, for example, pull-up diaper which comprises a liquid permeable coversheet, a liquid, air and vapor impermeable backsheet, an absorbent core or layer, made of fiberized wood pulp containing superabsorbent polymer (SAP) disposed between the coversheet and the backsheet, an outer layer of air and liquid permeable spunbond nonwoven polypropylene and an inner layer of air and liquid permeable spunbond polypropylene. The diaper also comprises elasticated crotch region having elastics on each side of the absorbent layer such that none of the "active length" of the elastic bands intersects the thigh elastic. The term "active length" refers to the length of the elastic band which is attached on the insert sides, under tension. A contoured insert containing the absorbent core is sandwiched between the coversheet and the backsheet.

In one embodiment, the absorbent article, which may be a diaper, comprises a back waist portion and a front waist portion connected together by nonwoven connectors. The back waist portion has an inner surface, an outer surface and two lateral ends, and a front waist portion having an inner surface, an outer surface and two lateral ends, wherein each one of said lateral ends of said back waist portion is adjacent and spaced apart in relation to one of said two lateral ends of said front waist portion. A first nonwoven connector connects one end of said two lateral ends of the waist portion to the adjacent lateral end of the front waist portion, and a second nonwoven connector connects the other lateral end of the back waist portion to the other adjacent end of the front waist portion. A hook fastener strip is provided on at least one of said nonwoven connectors, and a loop fastener strip is provided on the inner surface of the front waist portion. The hook and loop fasteners are pre-engaged thus providing a prefastened diaper.

The absorbent article may comprise six side seals, two lateral side seals, as in conventional pull-up diapers, two permanent side seals and two peelable side seals as more fully described hereinafter. The nonwoven connector may be folded n times wherein n is an even integer of 2 to 30. The folded nonwoven connectors are secured by a suitable securement means.

BRIEF DESCRIPTION OF THE DRAWINGS

In the drawings, wherein like reference numerals are employed to designate like parts wherein possible:

FIG. 8A is a cross-sectional view taken along the line 8A-8A of FIG. 8;

FIG. 8B is a cross-sectional view taken along the line 8B-8B of FIG. 8;

FIG. 8C is a view similar to FIG. 5 showing the overlapping of the front waist and the back waist of the diaper;

FIG. 11 is a stretched plan view of a different embodiment of the present invention similar to the embodiment illustrated in FIG. 10 with the tape tabs located on the outside surface of the back waist region, folded and adhesively secured to said surface;

FIG. 11A is a cross-sectional view taken along the lines 11A-11A of FIG. 11;

FIG. 11B is a cross-sectional view taken along the line 11B-11B of FIG. 11;

FIG. 11C is a view similar to FIG. 10C showing the overlapping of the front waist and back waist of the diaper;

FIG. 12A is a cross-sectional view taken along the line 12A-12A of FIG. 12;

FIG. 12B is a cross-sectional view taken along the line 12B-12B of FIG. 12;

FIG. 12C is a view similar to FIG. 10C showing fastening system;

FIG. 15 is a sectional view taken along the line 15-15 of FIG. 14 showing the manner of attachment the tape tab with a hook surface to the back waist portion of the diaper;

FIG. 15G is similar to FIG. 15 but illustrates an alternate fastener construction.

FIG. 15H is another fold construction wherein the hook engages the fastener's permanent attachment back surfaces, or the product backing;

FIG. 16 is a sectional view taken along the line 16-16 of FIG. 14;

FIG. 20A is a front perspective view of an alternate diaper construction having nonwoven connector portions connecting the back waist and front waist of the diaper and illustrating the hook and loop positions on different sides of the connector portions;

FIG. 20B is a right side view of the diaper shown in FIG. 20A;

FIG. 20C is a sectional view taken along the line 20C-20C in FIG. 20B showing a perforated line between the hook and loop;

FIG. 20D is a view similar to FIG. 20C with the perforated line broken and the hook and loop engaged with one another;

DETAILED DESCRIPTION OF THE INVENTION

Figure 1:
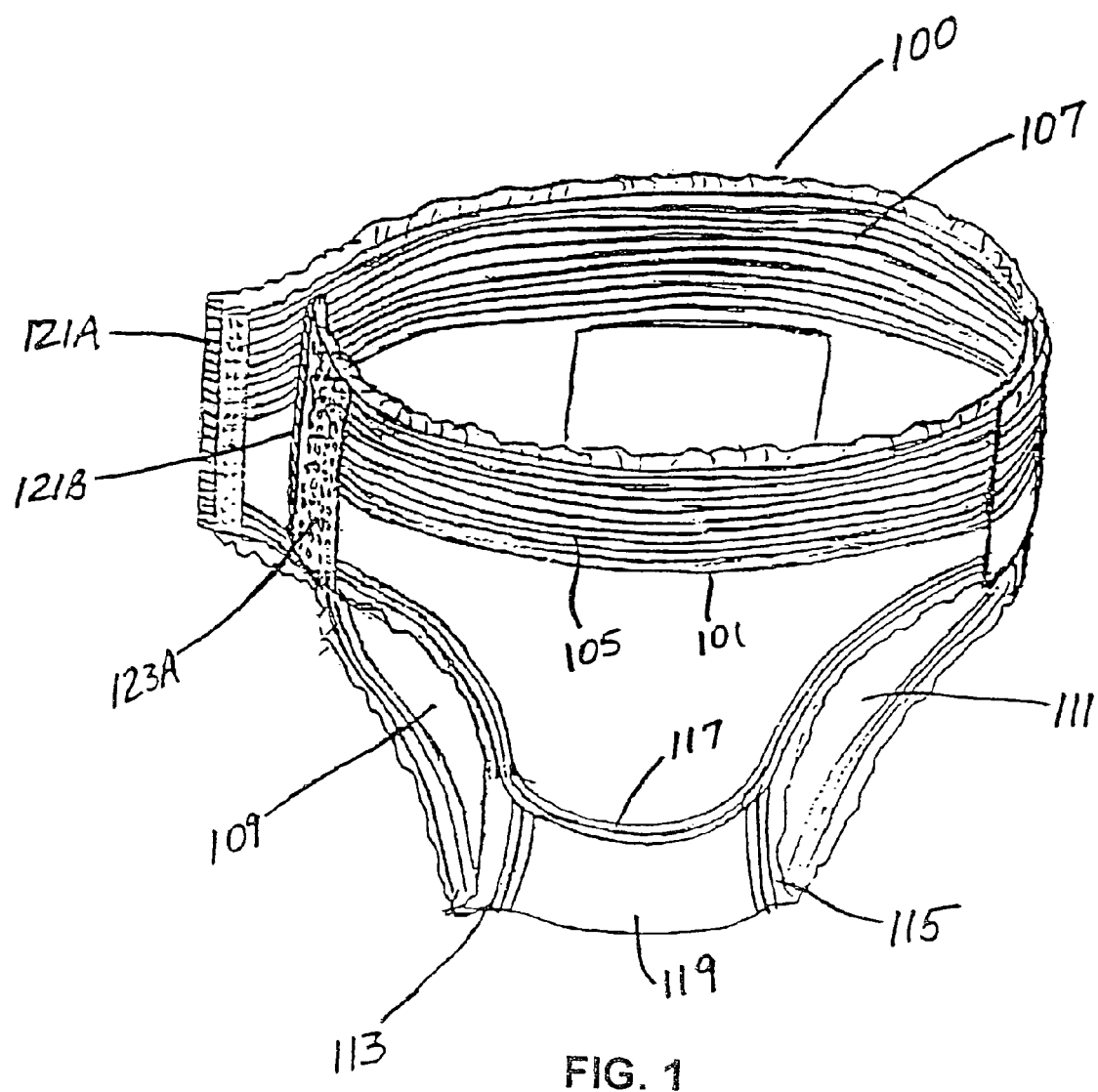
FIG. 1 is a perspective view of the disposable absorbent article of the present invention shown as a pull-up diaper having side seals which are broken apart on one side for illustrative purposes.
Figure 2:
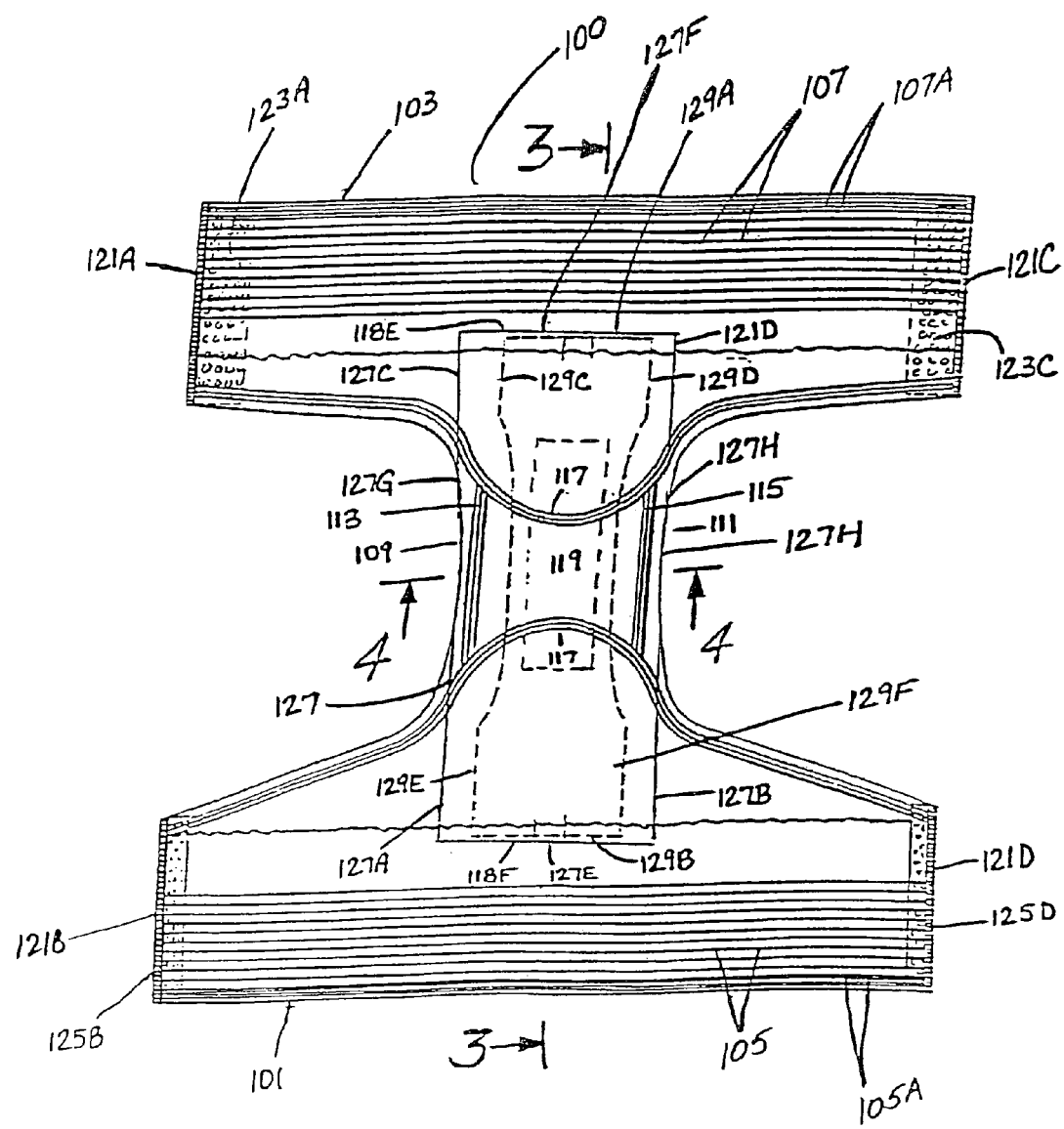
FIG. 2 is a stretched plan view of the pull-up diaper shown in FIG. 1.

Referring to FIG. 1, there is shown a pull-up diaper as an example of an absorbent article, generally designated as 100 comprising an elasticated back waist region 101 and an elasticated front waist portion 103. The elasticated back waist region 101 includes an elastic band comprising a plurality of elastic members 105 and belly elastics 105A spanned across the back waist 101, and the elasticated front waist region 103 includes an elastic band comprising a plurality of elastic members 107 and belly elastics 107A spanned across the front waist 103. The diaper 100 also comprises a pair of elasticated leg openings, i.e., a right elasticated leg opening 109 and a left-elasticated leg opening 111. The right leg opening 109 is provided at its peripheral edges with the crotch elastic members 113 and the right leg opening 111 is also provided at its peripheral edges with the crotch elastic member 115. Each leg opening also comprises a thigh elastic member 117 which is usually tensioned from about 0 to about 400 percent elongation, preferably from about 150 to about 250 percent elongation. The peripheral crotch elastic members 113 and 115 may also tensioned from about 0 to about 400 percent elongation, preferably from about 200 to about 300 percent elongation so that the leg openings fit snugly against the crotch region 119 of the wearer in order to prevent leakage of urine or other body exudates through the leg openings. The front and back of the diaper 100 are provided with the side seals formed by sealing the lateral edges 121A,121B disposed at the outer right edges of the back waist region 101 and the front waist region 103, and similar side seals formed by sealing the lateral edges 121C and 121D disposed at the outer left edges of the back waist region 101 and the front waist region 103 as shown in FIG. 2. These side seals may be formed by heat, pressure, combination of heat and pressure, or by a suitable adhesive in a manner known in the prior art. The side seals preferably have low peel strength so that when the seals are torn or peeled away their external edges remain clean. Preferably, the side seals strength may be from 1 to about 3 pounds per inch, and more preferably less than about 1 pound per inch.

The diaper is shown with elastics at the belly portion in the front or back but such belly elastics are not strictly necessary for some diapers.

Ordinarily, in order to change the diaper during wear and when a person has his shoes and pants on, the side seal is ripped open and the diaper is inspected for the presence of feces or exudates. Once inspected, the diaper is disposed of since it is often difficult to effectively reseal the side seals. In the embodiment of the present invention shown in FIG. 2, the diaper is provided with two strips of loop material 123A, 123C disposed adjacent the side seals 121A and 121C. Both the side seals and the strips of the loop fastener material are disposed parallel to the vertical axis of the diaper. Similarly, strips of hook material 125B, 125D are disposed adjacent the side seals 121B,121D, parallel to the vertical axis of the diaper. During use, when the front and back portions of the diaper are folded, the hook strips 125B and 125D engage onto the loop strips 123A and 123C, respectively thus providing additional sealed regions at the lateral edges of the front waist portion and the back waist portion. This construction permits opening the diaper for inspection by disengaging the hook and loop strips 123A and 125B, or the hook and loop strips 123C and 125D in order to inspect the diaper. If no feces or exudates are found, the diaper is closed, i.e., resealed by re-engaging the hook and loop strips without disposing of the diaper. FIG. 1 shows the diaper during wear with one edge partially open and the hook and loop strips in disengaged positions. It is preferable that the loop strips be located on the inside surface and the hook be located on the outer surface of the diaper.

Referring again to the drawings, more specifically to FIGS. 2-5, the diaper 100 comprises an insert member 127 which contains the absorbent core 129 sandwiched between the cover or top layer or sheet 131 (facing the body of the wearer) and the polyethylene backing film 133. The insert 127 is secured, adhesively or by some other suitable means, to a spunbond nonwoven layer 135. Optionally, the absorbent core 129 may be covered by the bottom tissue layers 137 generally made of wood pulp fibers or similar material. An acquisition layer 139 is interposed between the cover sheet 131 and the core layer 129 and serves to temporarily retain the body exudates and slowly distribute them through the absorbent core 129 in order to keep the skin dryer. The various layers are generally coextensive with one another and are sealed together to form a sealed composite structure.

As shown in FIG. 2, the absorbent core 129 spans substantial part of the length of the diaper 100 terminating at the front edge 129A, the back edge 129B, the right side edges 129C, 129E, and left side edges 129D and 129F. However, as it can also be seen from this figure, the back edge 129B and the front edge 129A of the absorbent core 129 are spaced apart a finite distance, which may be varied, relative to the diaper. The insert 127 is defined by the longitudinal side edges 127A, 127B, 127C and 127D, the lateral edges 127E and 127F, and includes the necked down region defined by the necked down contoured side edges 127G and 127H. The necked down region defined by the necked down side edges is elasticated at both sides by the elastic members 113,115. Three elastic members are shown although fewer or greater numbers of elastic members may be used if desired.

As previously mentioned, each leg opening 109, 111 is tensioned by a thigh elastic member 117 shown as a curved elastic in FIG. 2, but may be straight elastic element if desired. The thigh elastic may be tensioned from about 0 to about 400 percent elongation, preferably from about 150 to about 300 percent elongation for more improved fitness around the legs.

As is further shown in FIG. 2, the diaper 100 of the present invention has an elasticized crotch region 119 which is provided with one or more spaced-apart right elastic members 113 disposed interiorly of the leg right opening 109 on the right side edge of the insert, and one or more spaced-apart left elastic members 115 disposed interiorly of the leg opening 111 of the left side of the insert 127.

Figure 3:
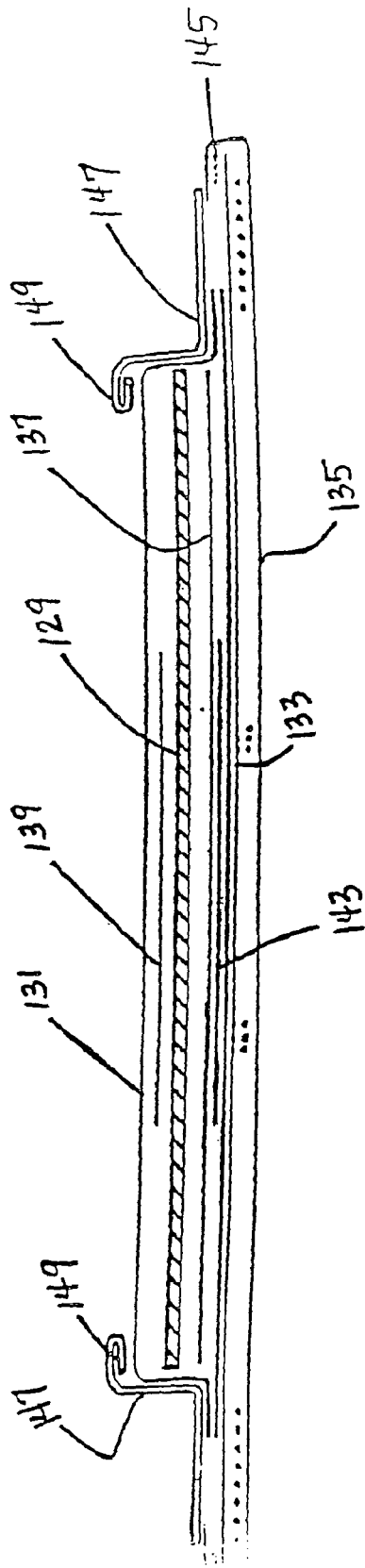
FIG. 3 is a sectional view taken along the line 3-3 of FIG. 2.
Figure 4:
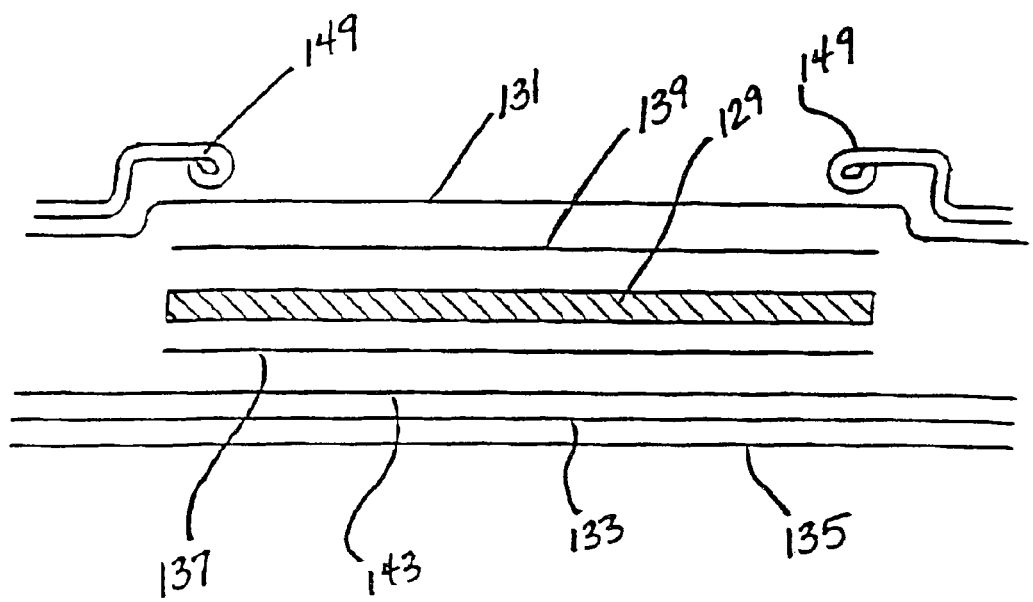
FIG. 4 is a sectional view taken along the line 4-4 of FIG. 2.
Figure 5:
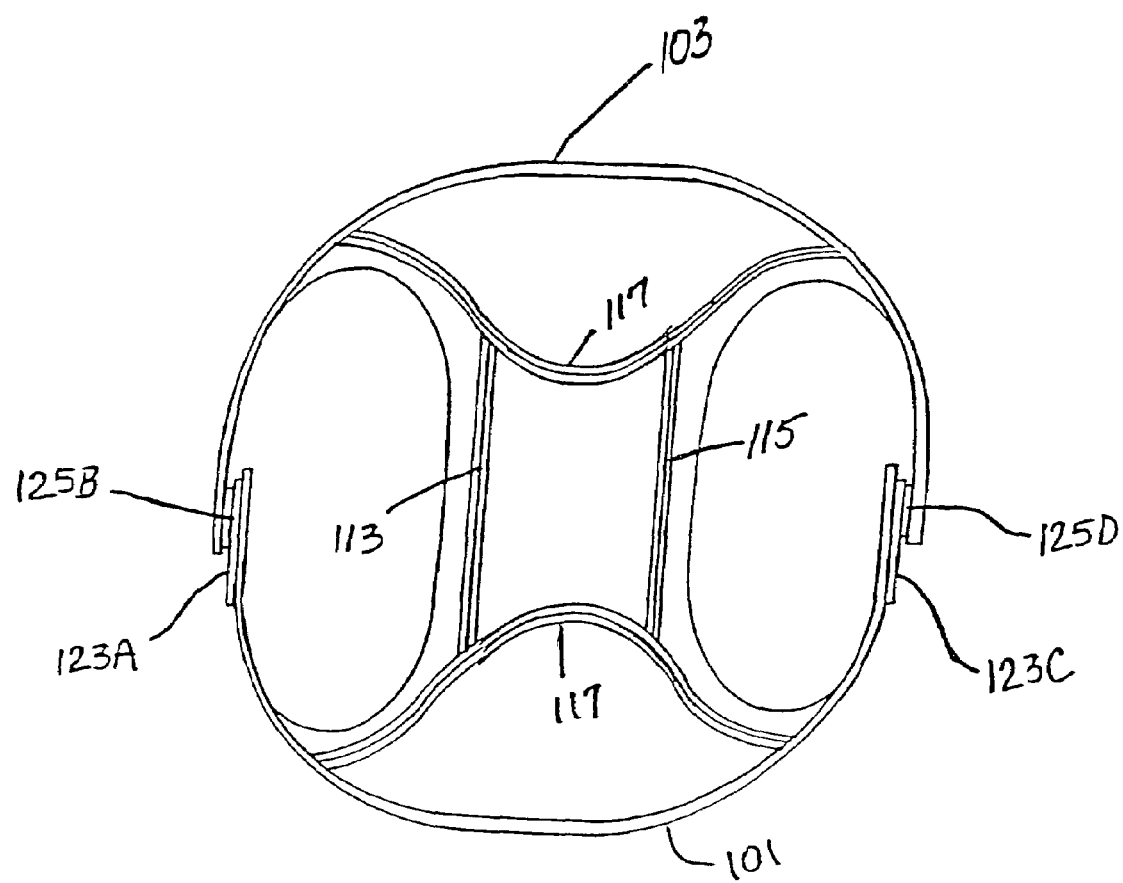
FIG. 5 is a schematic view illustrating overlapping of the front waist region and back waist region of the diaper shown in FIG. 1 and the manner of their attachment by hook and loop.

Referring to FIGS. 3 and 4, the coversheet or layer 131 is conveniently made of spunbond nonwoven polypropylene which is available from First Quality Fibers, Inc., McElhattan, Pa. The acquisition layer 139 is usually made of chemically bonded nonwoven polypropylene available from American Nonwovens, Columbus, Mo. Preferably, the width of this layer is substantially the same as the width of the absorbent core 129. This core may be made pulp fibers and superabsorbent polymers such as IM 7000 series available from Clariant Products, Inc., Portsmouth, Va., and Chemdal 200 series, available from Chemdal, Inc., Palantine, Ill. Alternatively, the absorbent core 129 may be made of dual layer construction, in which case, the absorbent polymer may be securely positioned between each layer of the absorbent material.

The film backing 133 is usually a polyethylene layer which is liquid, air and preferably vapor impermeable, and is placed under the absorbent core member 129 to prevent body exudates from leaking and otherwise soiling the user's bed and clothing. The width and length of the backing film 133 are generally at least equal to the width and length of the absorbent core 129. Polyethylenes suitable as backing film for the purpose of this invention are available from Clopay Plastics, Cincinnati, Ohio as is further shown in FIGS. 3 and 4, a layer 135 of spunbond nonwoven polypropylene is disposed as a backing layer and covers the area under the insert 127. This layer is usually coextensive with the overall width and length of the pull-up diaper.

As is further shown in FIGS. 2 and 3, there is one elasticated crotch cuff 149 on each side of the garment. Each of these crotch cuffs is formed of a layer of spunbond nonwoven polypropylene laminated by hot-melt adhesive or by heat, and forms a fluid and an air impermeable composite structure. The crotch cuffs are under no tension or are tensioned from about 100 to about 200 percent so that the garment can fit snugly against the body and prevent leakage of body fluids of exudates, without pinching the body of the wearer. Additionally, these cuffs act as barriers against fluid leakage on each side of the absorbent core.

The garment of the present invention also has an elasticated waist cuff 145 which, similar to crotch cuffs, is not tensioned or is minimally tensioned between about 1 to about 100 percent elongation in order to provide a tight body fit which is leak-proof without pinching the body or causing discomfort to the wearer.

The insert 127 is adhesively secured to the nonwoven backing film 133 and, as shown in FIG. 2, the crotch width of the insert 127 is narrower than its width at the waist. As previously mentioned, there are usually three elastic members 113,115 on each side, although fewer or more elastic members can be used, as desired.

As is further shown in FIG. 3, the pull-on diaper of this invention has a waist cuff base 147 on both the front and back of the article. Similar to the crotch cuffs, these waist cuffs prevent fluid leakage from the ends of the core members 129.

In the embodiment shown in FIG. 2, the hook and loop fastener strips are located adjacent the side seals. However, in a variation of this embodiment, the hook and loop fastener strips may be used without the side seals and put on the diaper without the wearer taking of his or her shoes or pants. When in use, the wearer may disengage the strips, inspect the diaper for leaks and/or exudates and if free from such materials, the hook and loop strips may be refastened. The hook and loop fasteners may be attached to the inside or outside of the diaper. However, it is preferable to attach the loops on the inside surface and the hooks on the outside surface since the hook material has a rough surface which would irritate the skin. If the diaper is provided with side seals, the seal may be torn and the hook and loop fasteners are used to fasten the diaper. In an alternative construction, no loop fasteners need to be used. In this construction, the product backside may have a nonwoven inner or outer surface and, therefore, the hook fastener will engage onto the nonwoven surface.

Figure 6:
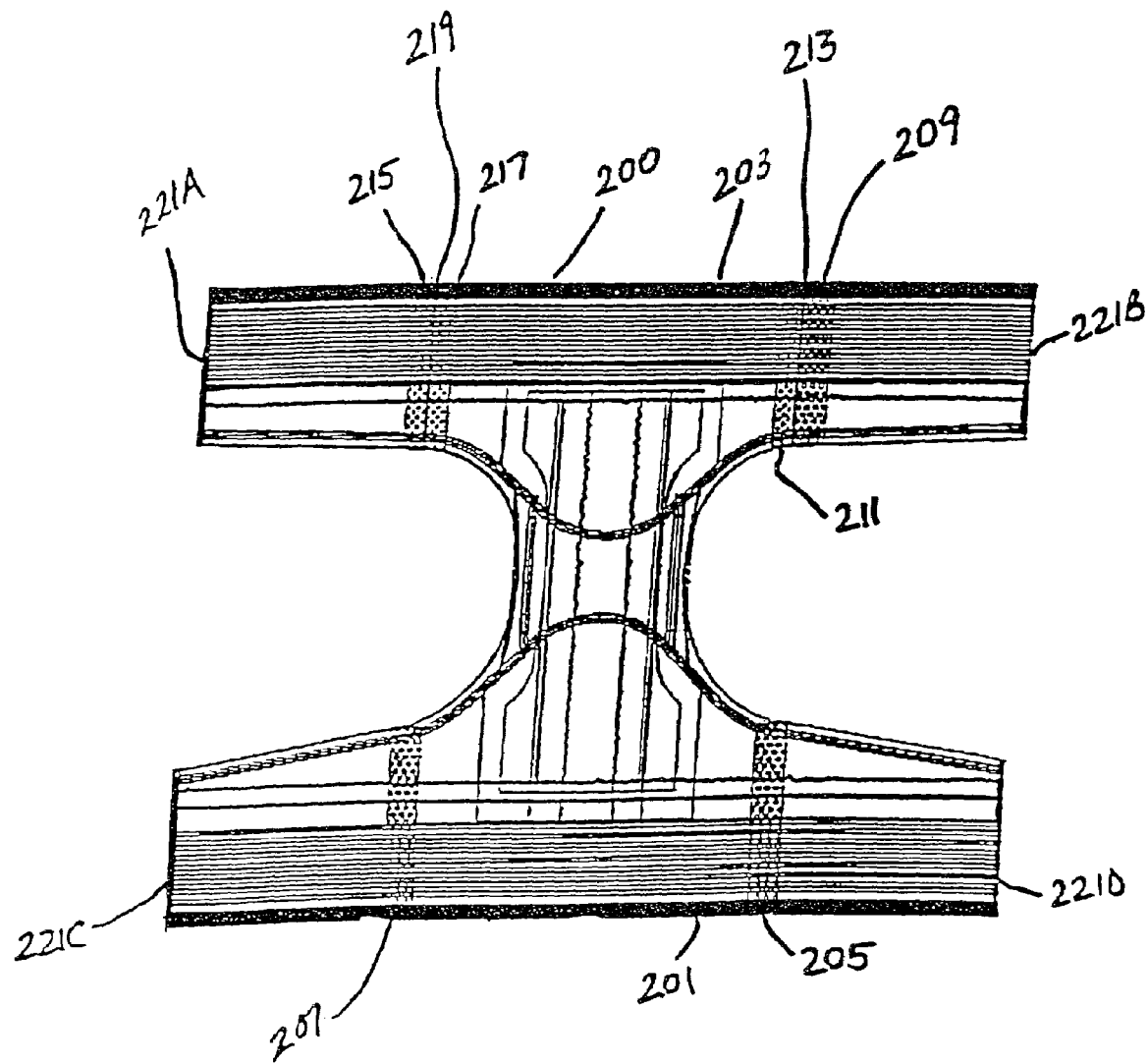
FIG. 6 is a stretched plan view similar to FIG. 2 but illustrating another variation of hook and loop fasteners.

Another variation of the fastening system for the diaper of this invention is shown in FIG. 6. The basic components of the diaper in this figure is the same as the diaper shown in FIG. 2 except for the number and location of the hook and loop strips. Thus, referring to FIG. 6, the front and back of the diaper 200 are provided with the side seals 221A, 221B disposed at the edges of the front waist region 203, and side seals 221C and 221D are located at the outer left edges of the back waist region 201. These side seals may be formed by heat, pressure, combination of heat and pressure, or by a suitable adhesive in a manner known in the prior art. The back waist region 201 comprises a pair strips 205,207 of a loop material, with the loop strip 205 spaced inward relative to the edge or side seal 221D on the inner surface of the back waist region and the loop strip 207 spaced inward relative to the edge or side seal 221C on the outer surface of the back waist region. The term "strip" as used herein is not limited to any particular configuration as it may be rectangular, square, circular or any other shape and may be a patch or a section of the surface of material itself. Thus, the material itself may constitute a loop suitable for engagement with the hook strips. The front waist region 203 comprises the loop strip 209 spaced apart relative to the edge or side seal 221B on the outer surface and a hook strip 211 on the inner surface adjacent the loop strip 209 and separated therefrom by a weakened tear line such as the perforated line 213. The front waist region 203 also comprises a pair of side-by-side hook strips 215,217 spaced inward relative to the edge or side seal 221A, and separated from each other by a weakened tear line such as the perforated line 219. Both hook strips 215,217 are located on the inner surface of the front waist region 203. In order to assemble and fasten the diaper, when the perforated lines 213 and 219 are torn and the waist region 201 and waist region 203 are folded on each other, the hook strip 209 engages the hook strip 215 and the hook strips 211 and 217 engage the loop strips 205 and 207, respectively. A segment of a nonwoven material or some other suitable material may be used as enforcement or backup portion for the perforated lines in order to assure a clean tear of the perforated line.

Figure 7:
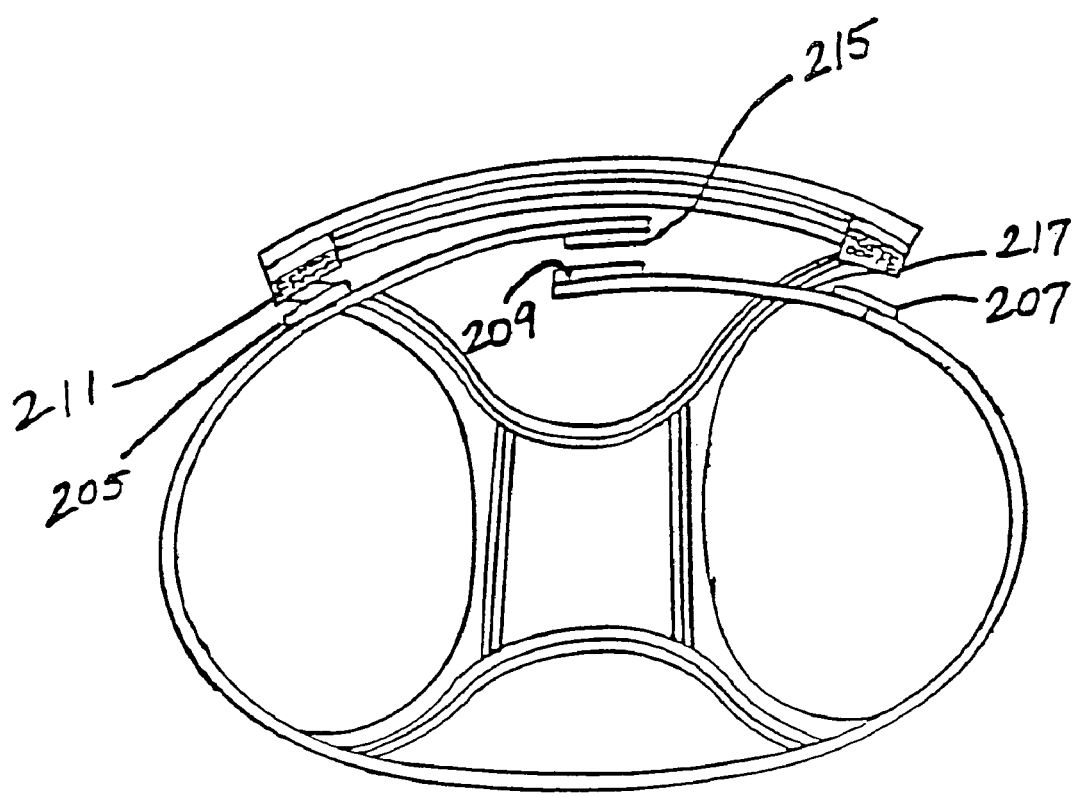
FIG. 7 is a schematic view similar to FIG. 5 but illustrating the hook and loop fastener arrangement in FIG. 6.

FIG. 7 is a schematic representation of the manner of fastening the hook and loop system shown in FIG. 6.

FIGS. 8-13 illustrate those embodiments of the invention using tape tabs as the male components of the fastening system. Otherwise, the structure of the diaper in these embodiments is the same as in FIGS. 2 and 6.

Figure 8:
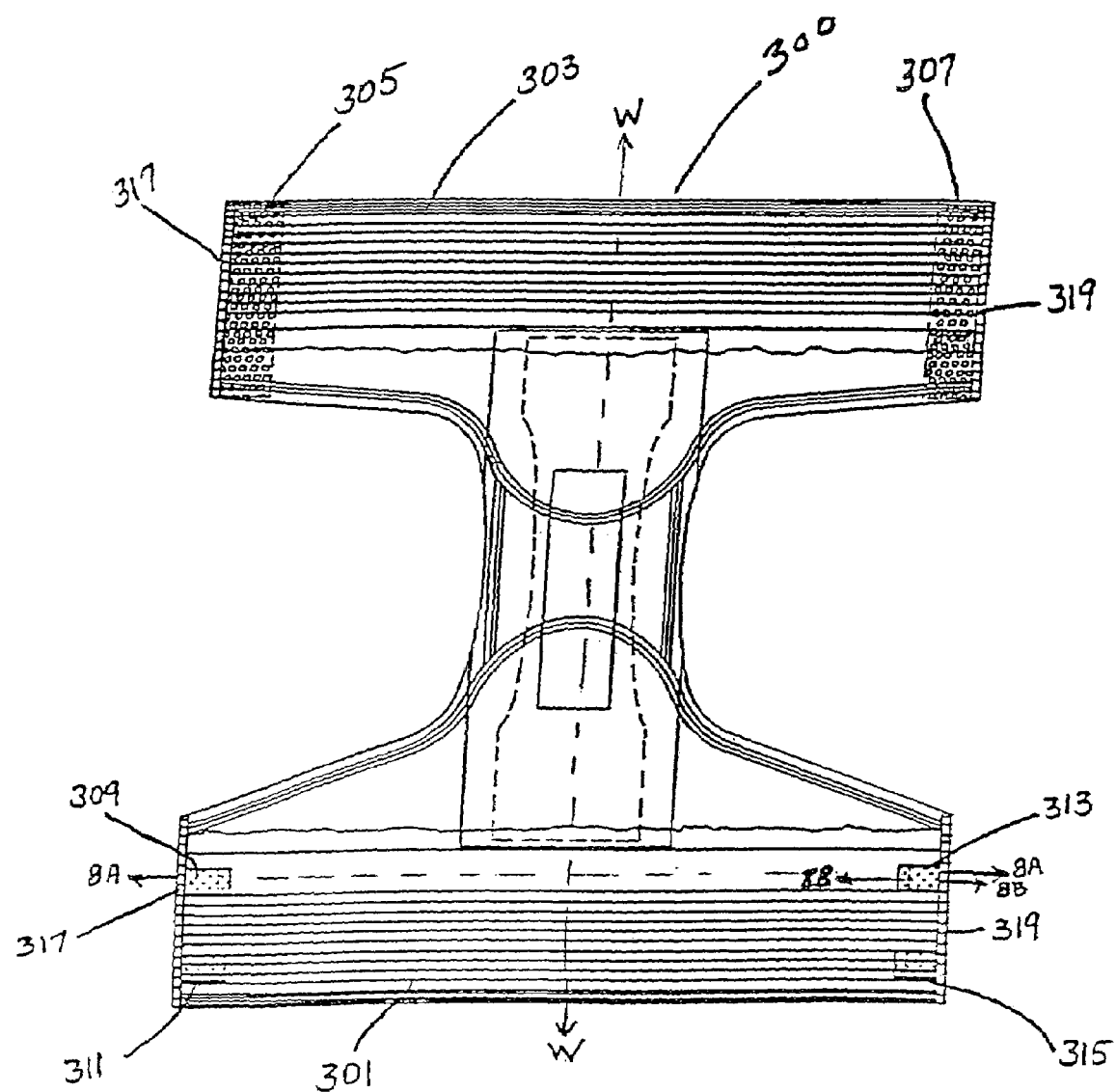
FIG. 8 is a view similar to FIG. 2 but using tape tabs with hooks in combination with loop fasteners wherein the tape tabs are located on the inside surface of the back waist.

Thus referring to FIG. 8 the diaper shown therein is generally designated as 300 comprising a back waist region 301 having opposed lateral wings, and a front waist region 303 having similar opposed lateral wings, relative to the longitudinal axis W-W of the diaper. The front waist region 303 comprises a pair of strips 305,307 of loop material disposed on the outer surface near or at the lateral edge of the respective wings, and the back waist region 301 has tape tabs 309, 311, 313 and 315 attached thereto on the inside surface at or near the edge of the wings. As shown in FIGS. 8A and 8B the tape tab 313 has an adherent surface 313A attached to the back waist portion, a release paper 313B, a hook surface 313C opposite said adherent surface, and an adherent surface 313D for attaching said hook surface to the back waist region. The tape tab 313 has a finger lift 313E in order to expose the hook surface. The release paper 313B and the finger lift 313E are optional and not strictly necessary.

In order to fasten the diaper the side seals 317,319 are torn and the adherent surface 313D is pulled away by lifting and pulling the finger lift 313E, the front waist region and the back waist region are then overlapped thereby engaging the tape tabs 309, 311, 313 and 315 onto the corresponding aligned loop strips 305 and 307. In the embodiment illustrated in FIG. 8 the front waist portion comprises the edge seal 317,319 at each lateral edge of the front waist region, and edge seals 321,323 at the lateral edges of the back waist region.

Figure 9:
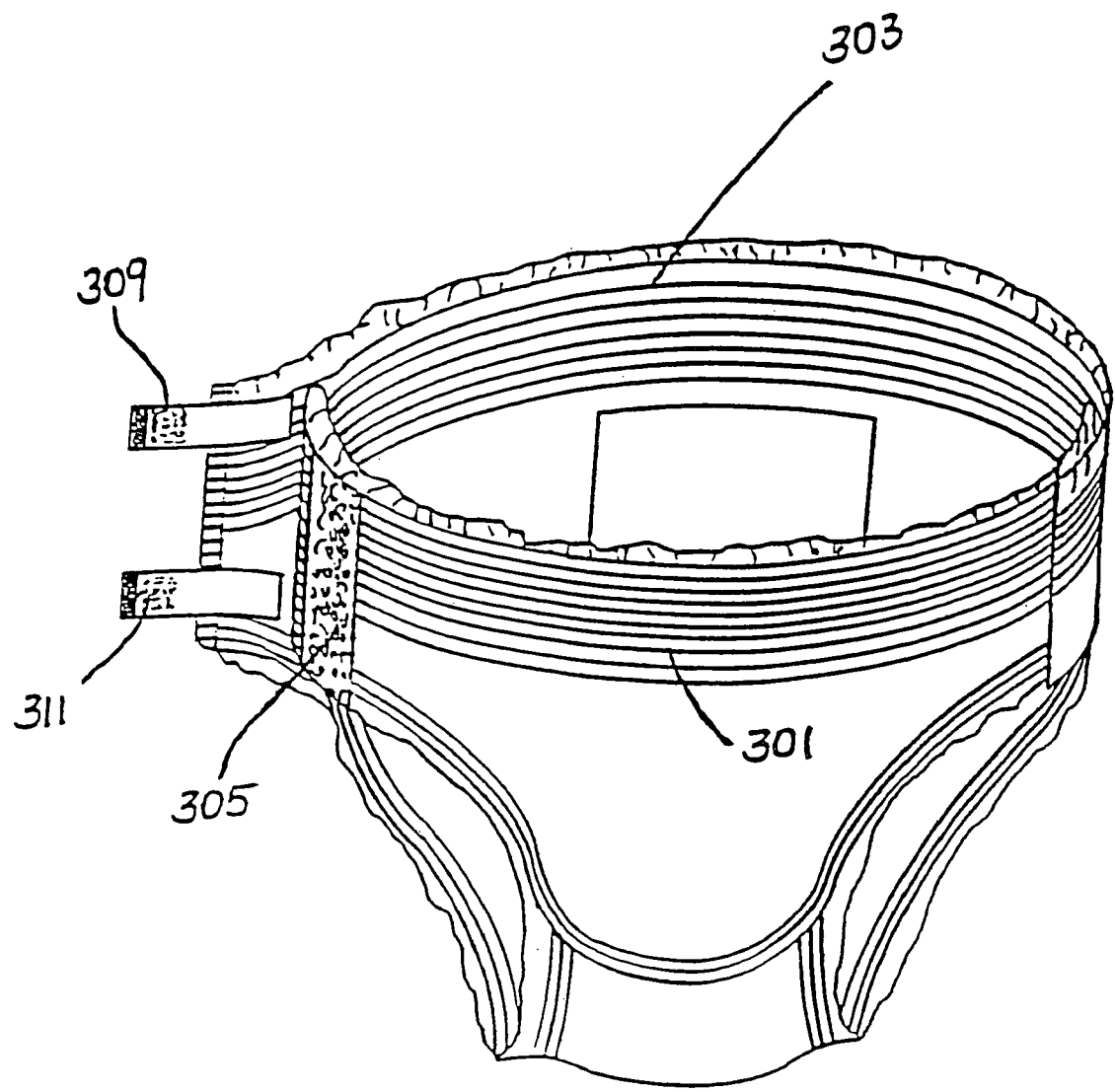
FIG. 9 is a perspective view of the diaper shown in FIG. 8 with the tape tabs pulled away from the loop fasteners and the diaper ready to wear.

FIG. 9 is a perspective view of the pull-up diaper shown in FIG. 8 and is similar to the diaper shown in FIG. 2 except for the provision of the tape tabs having hook surfaces. Otherwise, the structures of the two diapers are the same.

Figure 10:
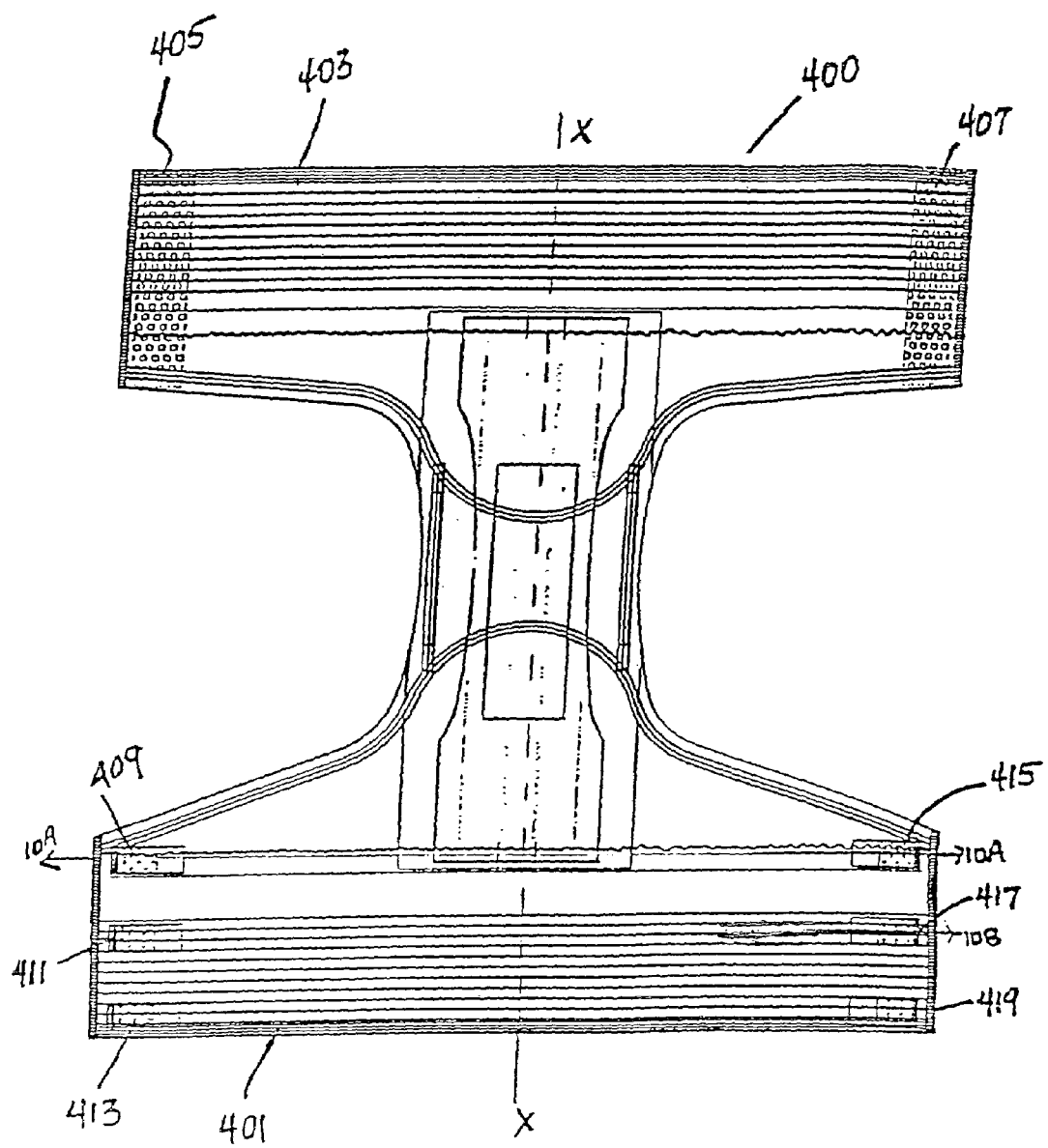
FIG. 10 is a stretched plan view of a pull-up diaper according to another embodiment of the present invention wherein the tape tabs are located on the outer surface of the back waist.
Figures 10A, 10B, 10C:
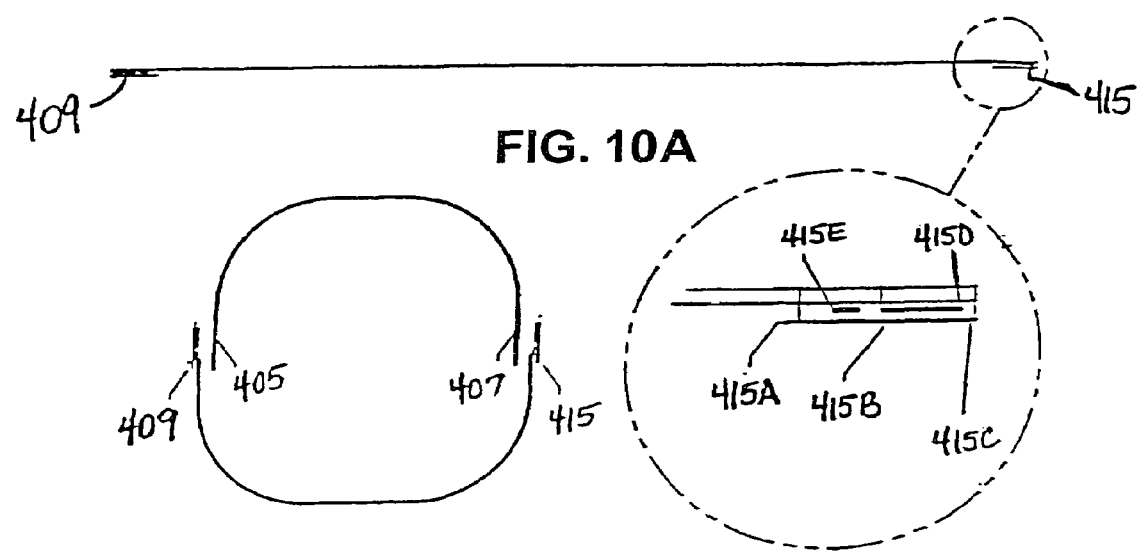
FIG. 10A is a cross-sectional view taken along the line 10A-10A of FIG. 10.
FIG. 10B is a cross-sectional view taken along the line 10B-10B of FIG. 10.
FIG. 10C is a view similar to FIG. 8C but showing the manner of fastening the front waist and back waist of the diaper shown in FIG. 10.

FIG. 10 is a stretched plan view of another embodiment of the invention similar to FIG. 8 but wherein the back waist region comprises three spaced apart tabs near the edge seal at each wing. Otherwise, the construction of the diaper is similar to the diaper shown in FIG. 8. Thus, the diaper shown in FIG. 10 is generally designated as 400 comprising a back waist region 401 having opposed lateral wings, and a front waist region having similar opposed lateral wings, relative to the longitudinal axis X-X of the diaper. The front waist region 403 comprises a pair of strips 405,407 of loop material, each strip being disposed near or at the lateral edge of its respective wing, and the back waist region 401 has three tape tabs 409, 411, 413 attached thereto near the edge of one of said wings, and three tape tabs 415, 417, 419 attached near the other wings. As shown in FIG. 10, the external edges of the tape tabs are spaced inwardly relative to the edge of each wing. Each of the tape tabs is attached to the outside surface of the back waist region 401. Thus, referring to FIGS. 10A-10C, tape tab 415 has an adherent surface 415A and a backing film 415B for attaching the tape tab to the back waist region 401. A finger lift portion 415C permits lifting the backing film away from the waist's outer surface. The tape tab has a hook surface 415D and a release paper 415E. The remaining tape tabs, i.e., tape tabs 409, 411, 413, 417 and 419 have a structure similar to tape tab 415 and are positioned on the outer surface of the back waist region in the same manner. These tapes are attached to the back waist surface such that each finger lift edge is adjacent to the side seals.

The back waist region 401 and the front waist region 403 are fastened together in the same manner described in connection with the diaper shown in FIG. 8. Also, shown in FIG. 10, the front and back waist regions comprise edge seals at each lateral edge or wing.

The embodiment shown in FIG. 11 is similar to the embodiment shown in FIG. 10 with the tape tabs located on the outer surface of the back waist region 501 of the diaper 500 except that the tapes are folded as shown in FIG. 11B. Referring to FIG. 11B which is an enlarged view of the tape tab 515, as shown therein, the tape tab construction is identical to the tapes shown in FIGS. 10, 10A, 10B and 10C. Thus, the tab has an adhesive surface 515A which is attached on the back side of the diaper and the remainder of the tape is folded to prevent the edges of the tape from interfering with the side seals. This tape also comprises a portion attached on the backside of the diaper waist, a release layer 521, a hook fastener 523 and a finger lift portion 521A.

Figure 12:
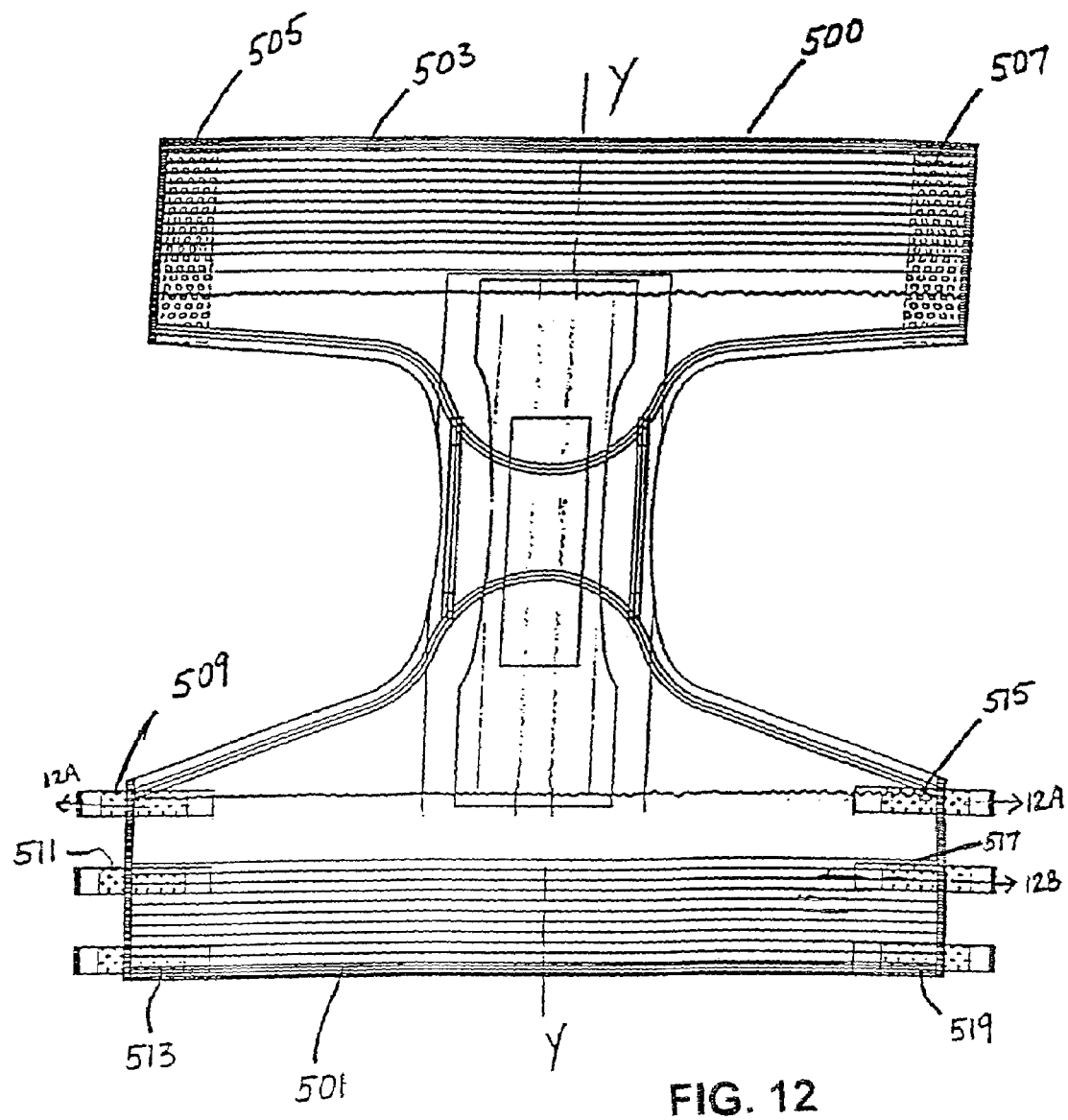
FIG. 12 is a stretched plan view of a different embodiment of the present invention similar to the embodiment illustrated in FIG. 10 with the tape tabs located on the outside surface of the back waist region and projecting outside of the lateral edges.

The embodiment shown in FIG. 12 is similar to the embodiment illustrated in FIG. 11 except that tape tabs attached to the back waist region project laterally beyond the edges of the respective wings. The diaper in FIG. 12 generally designated by 500 comprises a back waist region 501 having opposed lateral wings, a front waist region 503 having similar opposed lateral wings, a front waist region 503 having similar opposed lateral wings, relative to the longitudinal axis Y-Y of the diaper. The front waist region 503 comprises a pair of strips 505, 507 of loop material disposed near or at the lateral edges of the respective wings. The back waist region 501 has three tape tabs 509, 511, 513 attached thereto near the lateral edge of one of said wings, and the tape tabs 515, 517, 519 attached near or at the lateral edge of the other wing. Each of the tape tabs 509, 511, 513, 515, 517, 519 has a portion 509A, 511A, 513A, 515A, 517A and 519A, respectively, partly projecting beyond the lateral edge of each wing. These tapes are engaged with the respective loops on the back surface of the front waist region.

The manner of fastening the front and back waist regions to assemble the diaper is similar to the embodiments shown in FIG. 11. As shown in FIG. 12, if desired, side seals are provided at the respective lateral edges of each wing of the front and back waist regions. When one wishes to inspect or change the diaper, the tapes are disengaged from the loops, the side seal is torn and the diaper is inspected or changed.

Figure 13:
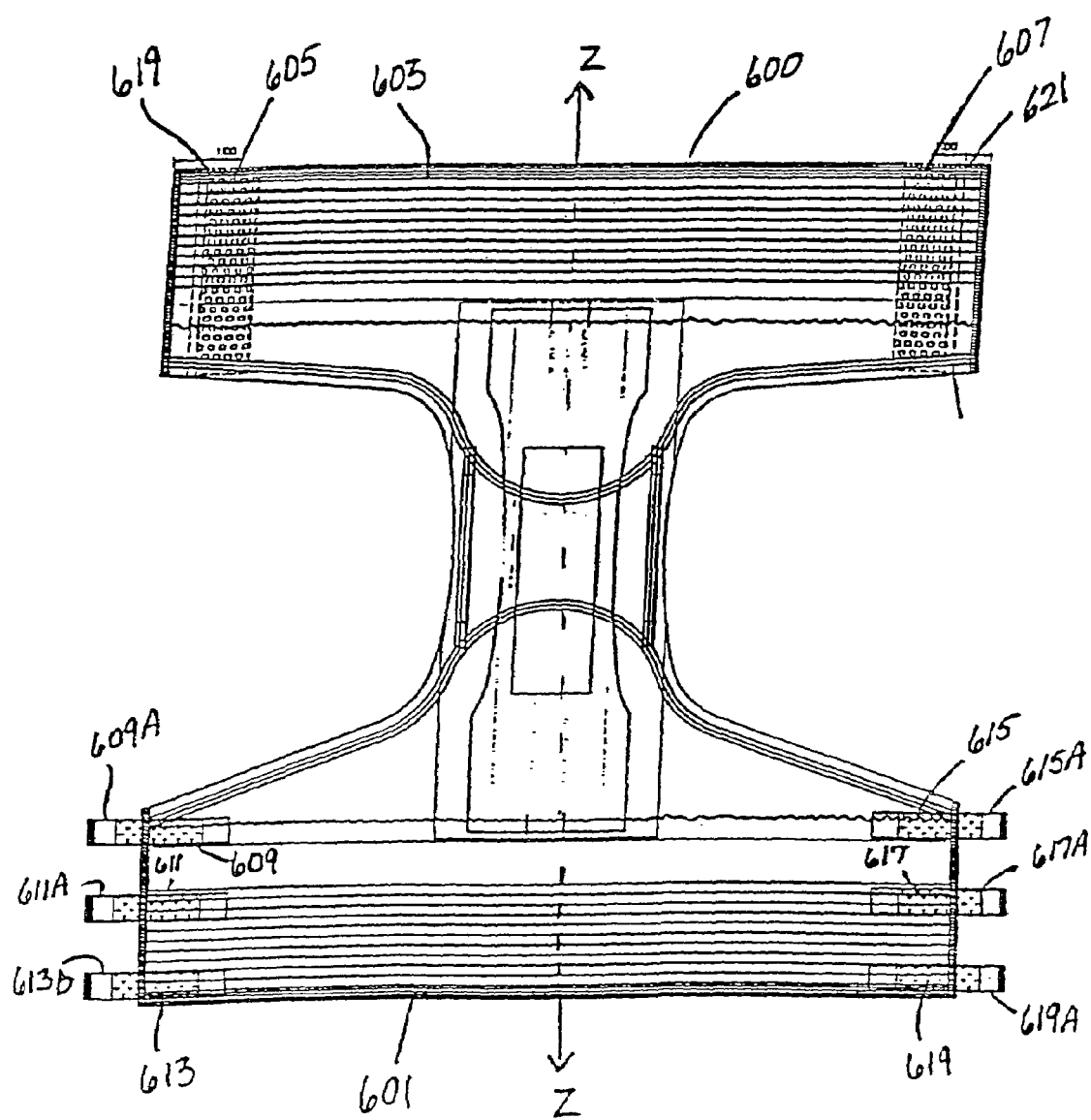
FIG. 13 is a stretched plan view of still another embodiment of the invention similar to FIG. 12 but having a weakened perforated line adjacent the side seal.

Another embodiment of the invention is illustrated in FIG. 13. The diaper shown in this figure is similar to FIG. 12 comprising a back waist region 601 having opposed lateral wings, and a front waist region 603 having similar opposed lateral wings, relative to the longitudinal axis Z-Z of the diaper. The front waist region 603 comprises a pair of loop strips 605,607 disposed adjacent their respective lateral edges and spaced apart therefrom. The back waist region 601 has three tape tabs 609, 611, 613 attached thereto near one lateral edge of one of said wings, and tape tabs 615, 617, 619 attached near or at the lateral edge of the other wing. The tape tabs in this embodiment are similar to the tape tabs in the embodiment shown in FIG. 12 having laterally projecting portions 609A, 611A, 613A, 615A, 617A and 619A. The difference between these two embodiments is that in the diaper shown in FIG. 13, the loop strips 605, 607 are spaced inward relative to the edges of the respective lateral wings and the front waist region 603 comprises weakened lines such as a perforated line 619 and 621 disposed adjacent each of the loop strips 605,607. Thus, when the diaper is fastened, the diaper may be inspected by tearing along the perforated lines to inspect the inside of the diaper for presence of urine or fecal material. Also, as shown in FIG. 13, the wings of the front and back waist regions have side seals for sealing the edges of the diaper.

The provision of perforated line in FIG. 13 permits tearing the diaper along the perforated lines without tearing the side seals, in order to inspect the diaper and engage the tapes with hooks to the loop surface. Each of the perforated lines may be disposed between the loop strip and the side seal or it may be disposed over the loop strip. If the diaper has perforated lines as aforesaid, the provision of side seals is optional. Whether or not the diaper is provided with side seals, the tapes with a hook surface may be engaged onto the loop strips to form the ready-to-wear diaper, and this may be performed even during the manufacture of the diaper.

Figure 14:
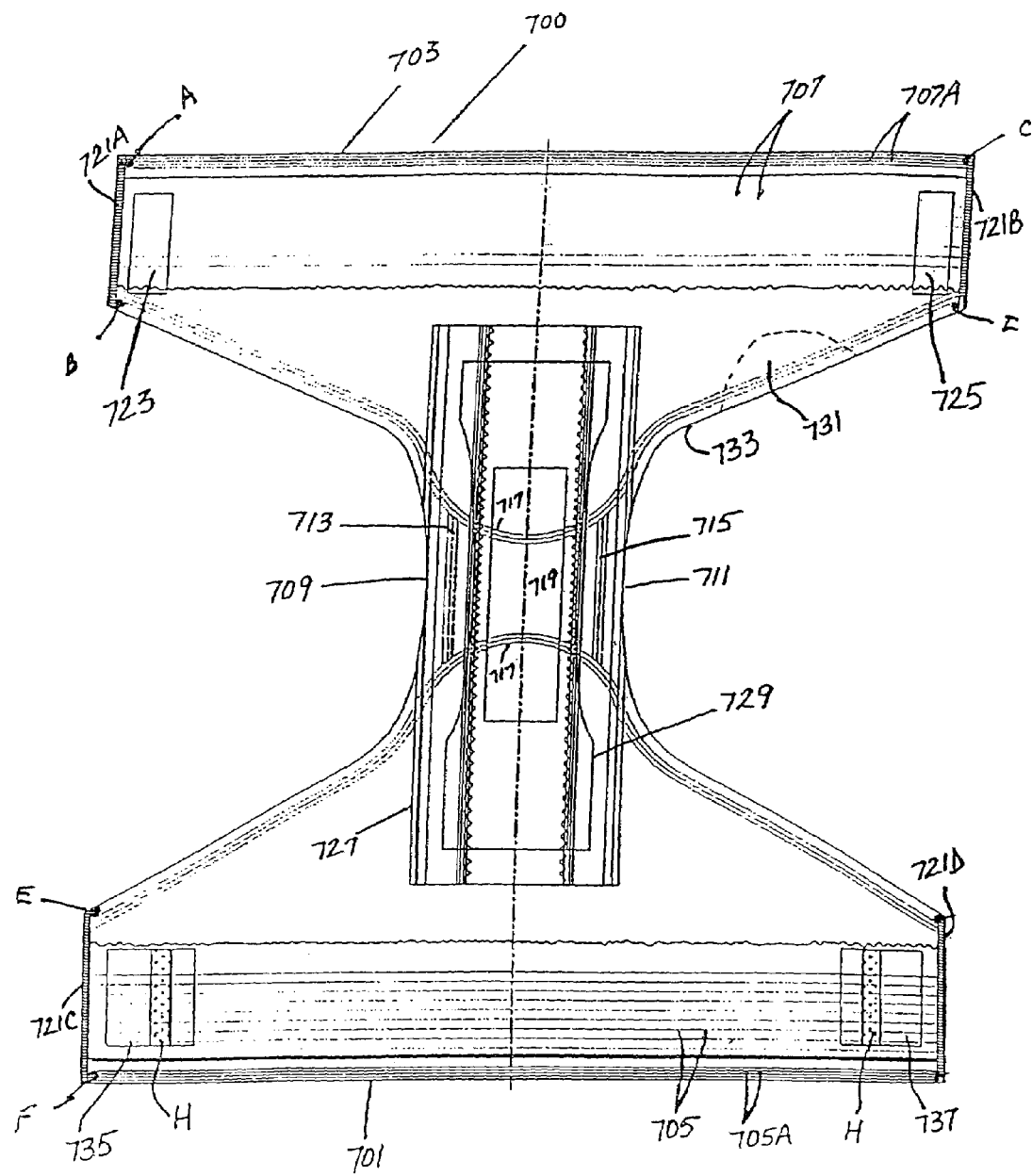
FIG. 14 is a view similar to FIG. 8 but illustrating the improved hook and loop arrangement in accordance with the present invention.

Referring to FIG. 14, there is shown a diaper generally designated by 700 in stretched view position comprising a back waist portion 701 and an elasticated front waist portion 703. Spanned across the back waist portion are a plurality of elastic elements or members 705 and belly elastic elements 705A, and a plurality of elastic elements or members 707 and belly elastic elements 707A are also spanned across the front waist portion 703. The diaper 700 also has a pair of elasticated leg openings, i.e., a right leg opening 709 and a left leg opening 711. Each of the right and left leg openings 709 and 711 is provided at its peripheral edge with a crotch elastics 713 and 715, respectively. Each leg opening also comprises thigh elastic 717 which are usually tensioned between about 0 to about 400 percent elongation, preferably between about 150 to about 250 percent elongation. The peripheral crotch elastic members 713 and 715 are tensioned between about 0 and about 400 percent elongation, preferably between about 200 and about 300 percent elongation so that the leg openings fit snugly against the crotch region 719 of the wearer in order to prevent leakage of urine or other body exudates through the leg openings. The front and back waist portions of the diaper 700 are provided with the side seals 721A,721B disposed at the outer right edges of the front waist region 703, and similar side seals 721C and 721D are disposed at the outer right edges of the back waist region 701. These side seals may be formed by heat, pressure, combination of heat and pressure, or by a suitable adhesive in a manner known in the prior art. The side seals preferably have low peel strength so that when the seals are torn or peeled away their external edges remain soft and clean. Preferably, the side seals strength may be from 1 to about 3 pounds per inch, and more preferably less than about 1.5 pound per inch. Also, a suitable material such as a nonwoven may be attached on the side seal on the back waist so that when the side seals are torn both external edges remain soft and clean.

In order to assure the mechanical integrity of the side seals, the end of each side seal, both in the front waist region and the back waist region, may be provided with a heat spot or a hot melt point such as A, B, C and D in the front waist region, and E, F, G and H in the back waist region.

The diaper 700 is shown provided with elastics at the belly portion in the front or back but such belly elastics are not strictly necessary for some diapers. An insert member 727 containing absorbent core 729 is sandwiched between the coversheet 731 and the backsheet 733.

In the embodiment illustrated in FIG. 14 the diaper construction is basically similar to the diaper shown in FIGS. 8 and 13 however, it has a different fastening system designed to further improve production and assembly of the diapers and facilitate their utilization. Thus, the diaper shown in FIG. 14 comprises a liquid permeable coversheet made of 100 percent polypropylene spunbond nonwoven which is treated with a surfactant and a backsheet made of a liquid, air and vapor impermeable polyethylene film. An absorbent core or layer is interposed between the coversheet and the backsheet. The absorbent core is made of fiberized wood pulp (fluff) containing superabsorbent polymer (SAP), preferably crosslinked polyacrylic polymer in the amount of from about 20 to about 45 weight percent of SAP based on the weight of the fiberized wood. The backsheet is placed under the absorbent layer to prevent fluid from leaking out and soiling the user's clothes or bed. Optionally, an acquisition layer may be interposed between the absorbent core and the coversheet. The acquisition layer is usually made of chemically or thermally bonded nonwoven polyester film.

The diaper shown in FIG. 14 has an elasticized back waist portion and an elasticized front waist portion, both elasticized under the same tension, with the elastic elements being attached to the outer nonwoven polypropylene, a crotch region, a belly/back portion which may comprise elastic bands attached between the outer and inner nonwoven polypropylene, under the same tension relative to each other, and an elasticized crotch region having elastic elements wherein none of the "active length" of the elastic elements intersect the through elastic. The diaper edges are sealed with side seals as hereinbefore described. Also, the belly/back elastics and the thigh elastics are usually sandwiched between the inner and outer nonwoven.

In accordance with the embodiment of the invention shown in FIGS. 14-16, the front waist portion 703 of the diaper is provided with two loop strips 723 and 725 each located at the respective lateral edges of the front waist portion adjacent the seal strips 721A and 721B. In the back waist portion 701, there are two tape tabs 735 and 737 located adjacent the seal strips 721C and 721D. The novel attachment of the tape tabs are shown in FIGS. 15 and 16. The tape tabs 735 and 737 shown in FIG. 16 are similar in construction and hence only one of them will be described in further detail. Thus, the tape tabs 737 shown in FIGS. 14-16 may be elastic or non-elastic nonwoven material comprising a fastener A portion and a portion B which is permanently secured to the outer surface of the back waist. The tab 737 may also be a composite of nonwoven elastomer-nonwoven, or nonwoven film, if desired. Alternatively, portion B may consist of a subportion B1 which is permanently secured to the outer surface of the back waist region and another subportion B2 which is releasably adhered to the outer surface back waist region. A strip of hook material H is secured to the fastener A by a suitable adhesive and a portion of the fastener A is folded as shown in FIG. 15 and the fold is maintained in place by a securement means such as a hot melt adhesive, ultrasonic bond or heat spot E. The securement mean may conveniently be a series of adhesive points of a variety of patterns, shapes and sizes, and may be aligned linearly or non-linearly.

In order to avoid contact between the hook material and the clothing of the wearer of the diaper, the fastener portion A may be folded inwardly in which case the surface of the hook will stick to the surface of the nonwoven backing. This will obviate the use of securement means, but if desired, a securement means may still be used.

Another desired construction of the fastener A is shown in FIG. 15G, which is similar to the construction illustrated in FIG. 15 except that the fastener portion A is not folded under the permanently secured subportion B1 while the product is in storage. In use, the fastener A is folded under the portion B so as to be capable of engagement with the loop strip. Another construction shown in FIG. 15H contemplates that the hook H engages the fastener's permanent attachment back surface, or the product backing.

The fastener A may be folded n number of times wherein n is an integer of 1 to 5 depending on location of the tape tabs and whether they are on the inner or outer surface of the back waist region. As a practical matter, however, less than 4 folds are preferred. Also, the folded portion of the fastener A terminates at a finger lift 739 (see FIGS. 15 and 16) which serves to grip the end of the fastener and lift it away from the back waist of the diaper. As shown in FIGS. 15G and 15H, the folds can be such that the hook on fastener portion A may point outwardly or inwardly, and the hook engages B1, B2 or the product back surface.

Figure 15A:
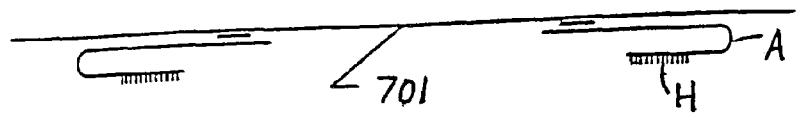
FIGS. 15A, 15B, 15C, 15D, 15E and 15F each represents a schematic diagram of different arrangement of the hook surface, at different positions.
Figure 15B:
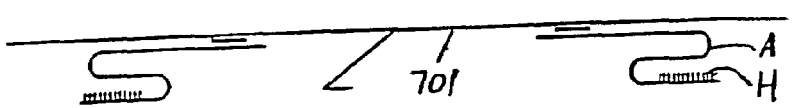

As previously described in FIG. 15A the fastener A is folded once and the hook surface is secured to the fastener A away from the outer back waist surface. In FIG. 15B the fastener A is folded twice, and in FIG. 15C the fastener A is folded three times. Consequently, the hook surface H faces toward the outer surface 701 of the back waist (FIG. 15B) or away from the outer surface 701 of the back waist (FIG. 15C).

Figure 15C:
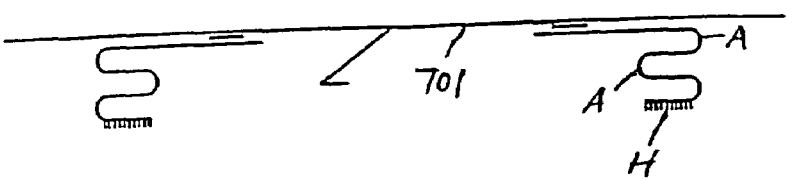
Figure 15F:
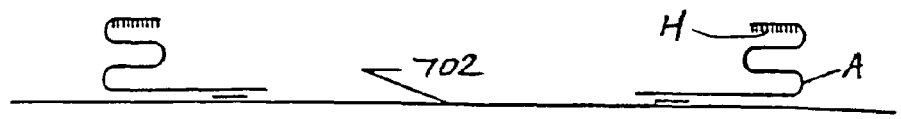
Figure 15E:
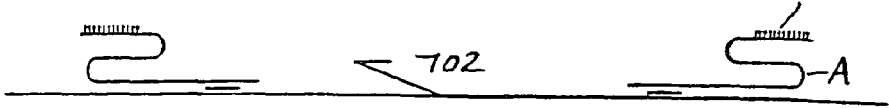
Figure 15D:
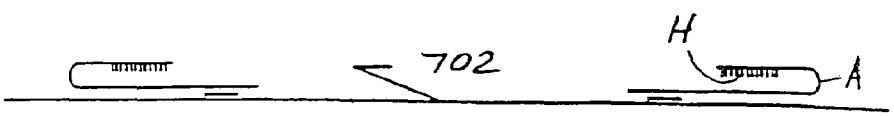

FIGS. 15D, 15E and 15F are similar to FIGS. 15A, 15B and 15C, respectively but the fastener A is attached to the inner surface 702 of the back waist, with the hook surface in each case facing in opposite direction, i.e., toward the inner surface 702 of the back waist (FIG. 15D), away from inner surface 702 of the back waist (FIG. 15E) and toward the inner surface 702 of the back waist (FIG. 15F).

It must be mentioned that in the construction of a diaper chassis, the diaper may be preformed, if desired, with the inner and outer surface of the front waist region made of nonwoven material. This enables the hook to engage into the nonwoven inner or outer surface of the front waist region. A particularly suitable hook is one manufactured by Bender Macroplast, Schaumburg, Ill., designated by code no. 42-288-HX2000-PP3-Tape 50.

Figure 17:
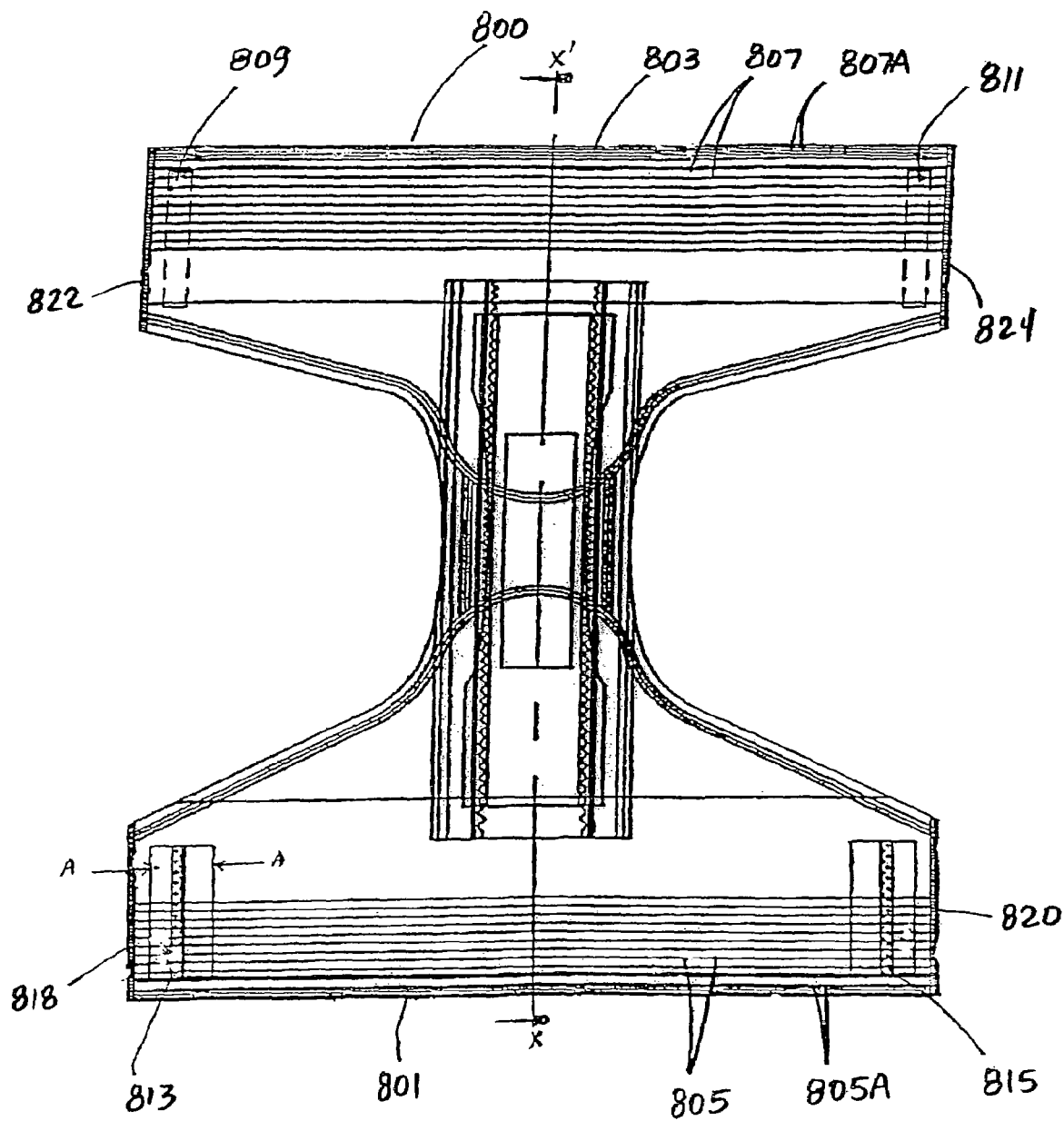
FIG. 17 is a stretched view of a pull-up absorbent article incorporating the fastening system of the present invention.

Referring to FIG. 17, there is shown a diaper generally designated as 800 having the general construction and configuration of the diaper hereinbefore described in connection with FIG. 14 except for differences in the fastening system and diaper side seals. The diaper 800 comprises a back waist region 801 having opposed lateral wings, and a front waist region 803 having similar opposed lateral wings, both relative to the longitudinal axis x'-x' in FIG. 17. Spanned across the back waist region 801 are a plurality of elastic elements 805 and belly elastic elements 805A, and similarly, a plurality of waist elastic elements 807 and belly elastic elements 807A are spanned across the front waist region 803. Other structural features of the diaper 800 are similar to the diaper 700 illustrated in FIG. 14 except as hereinbefore mentioned and therefore will not be described further. Attention will be focused on the multifold fastening system of the diaper 800 and the side seals. As shown in FIG. 17, the lateral edges of the front waist region 803 are provided with loop fasteners 809,811 and the lateral edges of the back waist region 801 are provided with folded tape tabs with hook fasteners 813,815 aligned with, and adapted to engage the corresponding loop fasteners 809, 811 when the back waist 801 is folded over the front waist 803.

As shown in FIG. 17, each of the lateral wings terminates at their respective lateral ends 818,820 in the back waist portion and at the lateral ends 822 and 824 in the front waist portion. Thus when the back waist portion is folded onto the front waist portion, the lateral ends 818 and 822 overlap and can be sealed to form one lateral side seal, and the lateral ends 820 and 824 overlap and can be sealed to form another lateral side seal. It must be mentioned that such lateral side seals are conventionally formed during the manufacture of conventional pull-up diaper as described, for example, in copending, commonly assigned application Ser. No. 09/965,381 filed Sep. 27, 2001 and the patents referred to therein, the disclosures of which are fully incorporated herein by reference. These side seals must have sufficient strength to hold the diaper intact during manufacturing, packaging and use of the diaper, yet they must be readily peelable in order to be able to widen the waist portion when desired. These side seals will also be referred to herein as lateral side seals.

Figure 17A:
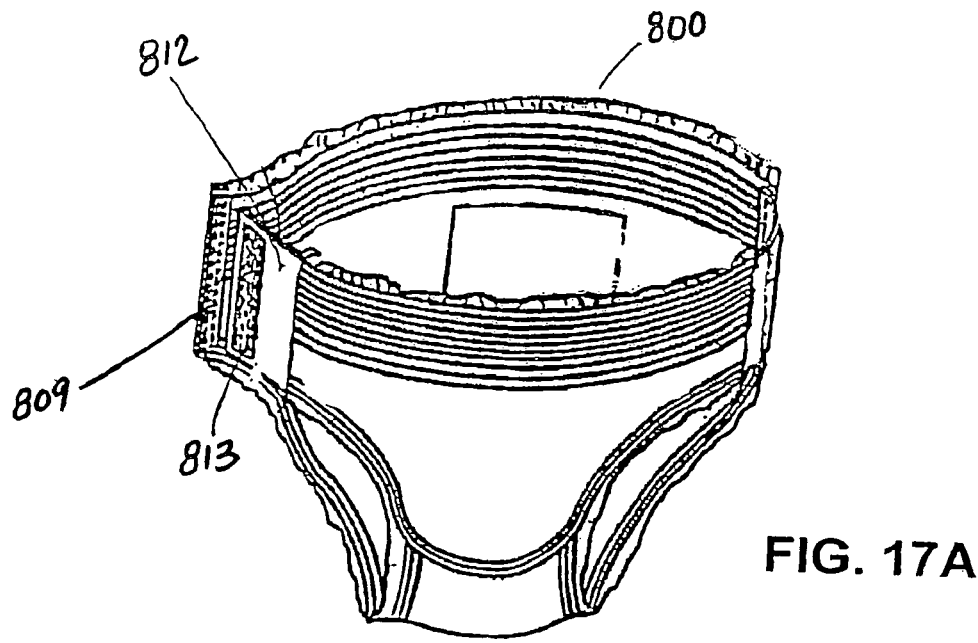
FIG. 17A is a front perspective view of the diaper which is shown in unfolded stretched position in FIG. 17.
Figure 17B:
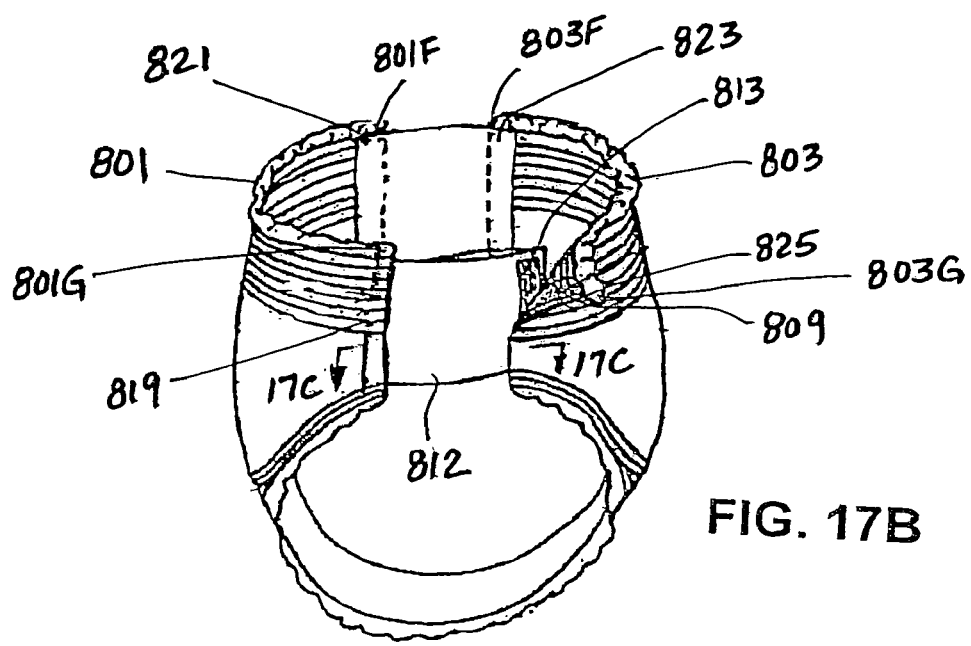
FIG. 17B is a right side view of the diaper shown in FIG. 17A.

Referring to FIGS. 17A and 17B there are shown side seals 819 and 821 formed by permanent attachment of the edges of the nonwoven connectors 812,814 to the inner end surfaces of the front waist region 801, and side seals 823,825 which releasably attach the nonwoven connectors 812,814 to the inner end surfaces of the back waist region 803 by means of the hook fastener 813 and loop fastener 809.

Figure 17C:
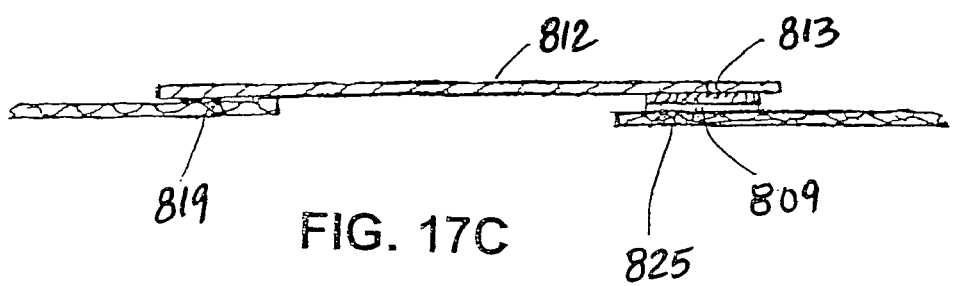
FIG. 17C is a sectional view taken along the line 17C-17C of FIG. 17B.

The diaper front waist has two opposing lateral ends or edges 801F and 801G, and the back waist region 803 has two opposing lateral ends or edges 803F, 803G. When the diaper side seals have been torn, the respective adjacent opposed edges (i.e., 801F to 803F and 801G to 803G) are connected together by the nonwoven connectors 814 and 812, respectively, thus connecting the back waist of the diaper to the front waist of the diaper as seen in FIG. 17B. As is further seen from FIGS. 17B and 17C, the nonwoven connector 812 comprises the hook 813 which is adapted to engage the loop strip 809 disposed on the inner surface of the front waist portion at or near its lateral end. As previously described in connection with the diaper shown in FIG. 2, the inner and outer surfaces of the front waist may be a nonwoven surface. Therefore, the hook fastener engages the nonwoven surface and no separate loop strip will be required.

In order to put on the diaper when a person has his pants and shoes on, the side seals 818 to 822 and 820 to 824 (when side seals are used) are torn and the diaper is put on as in a conventional diaper. Thus, the wearer can insert his legs through the leg holes and the diaper is pulled up to the waist. This can be done without removing the shoes or the pants. After the diaper is pulled up, the waist is adjusted by adjusting the fasteners to achieve a close comfortable fit. In order to remove the diaper, it may be simply pulled down in the same manner as pulling down a regular underwear.

Figure 18:
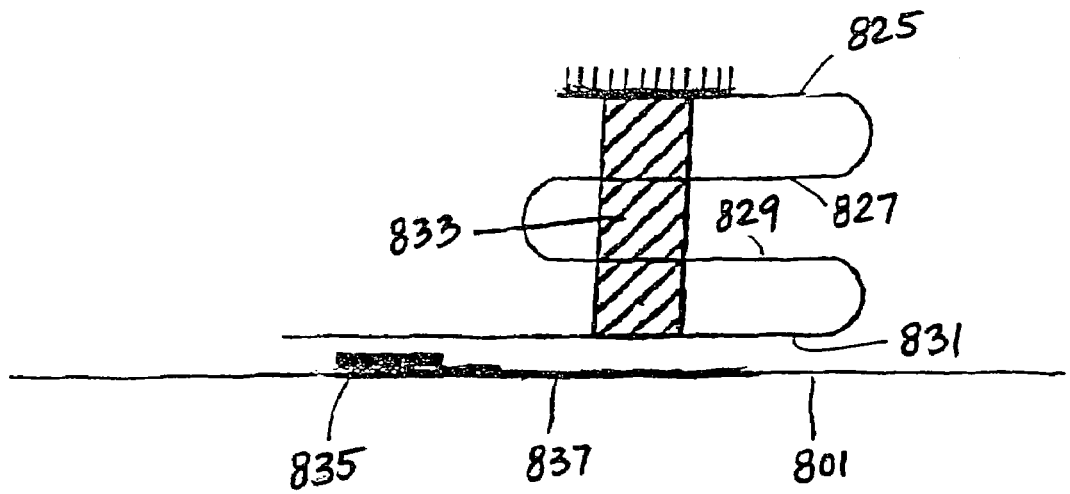
FIG. 18 is a view showing the fastening system location on the inner surface of the back waist region of the diaper shown in FIG. 17 after unfolding the diaper.
Figure 19:
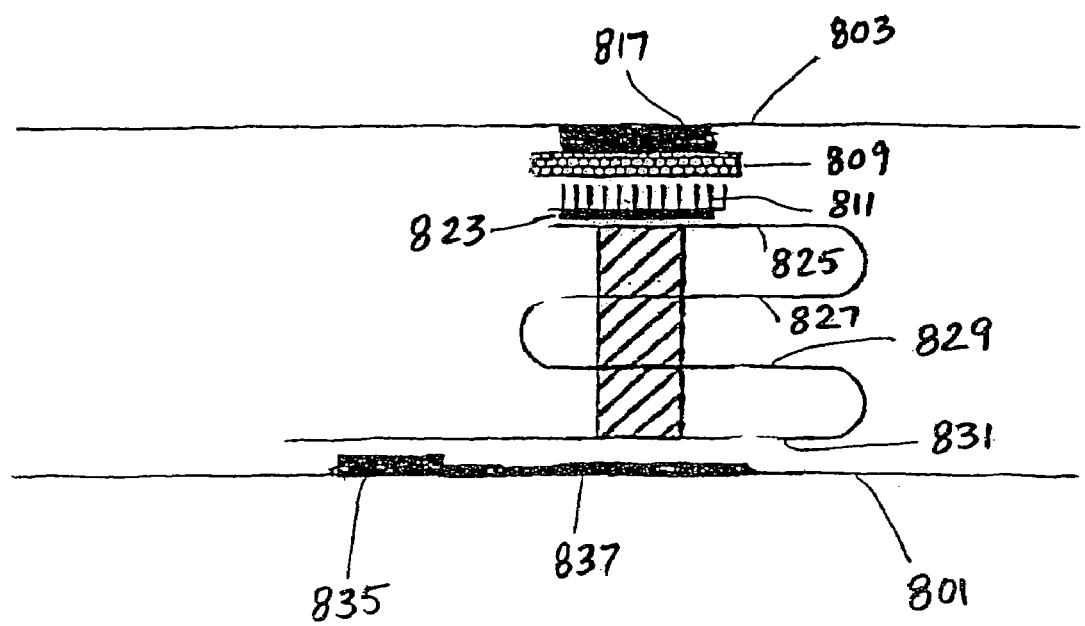
FIG. 19 is a cross sectional view taken along the line A-A of the tape tab shown on the back waist region of the diaper shown in FIG. 17 before unfolding the diaper.

FIG. 18 shows the relative locations of the tape tabs for the unfolded diaper, and FIG. 19 shows the relative locations of the tape tabs for the folded diaper. In FIG. 19, there is shown, from top to bottom, the inner front waist 803, a first adhesive layer 817 to attach the loop fastener 809 to the inside of the front waist region, a layer of hook material 811 adapted to engage the loop fastener 809, a second adhesive layer 819 for attaching the hook material 811 onto the folded tape tab backing portion 825 or the nonwoven connector. FIGS. 18 and 19 illustrate nonwoven connectors 812,814 with four folds as shown by the folds 825, 827, 829 and 831. The folded portions 825-831 are secured together by a securement means 823 which also permanently secures the tape tab onto the inside surface 835 of the back waist region 801. Optionally, a peelable adhesive layer 837 may be provided in order to temporarily attach the tape tab on the inner back waist 801. The provision of a peelable adhesive layer is beneficial in that it permits the tape tabs to be secured on the surface of the diaper and then ultrasonically welding the tape tabs permanently on the diaper surface. This is usually accomplished from the area of the tape tab that is not under the folds. Thus, the portion of the tape tab which is to be attached to the diaper should have a larger surface in order to avoid damage to the folded areas. In lieu of ultrasound welding, permanent hot melt adhesive may be used, in which case the surface of the bottom layer of the tape tab need not be larger and, in fact, it may even be smaller. Thus, the hot melt adhesive 837 may be peelable or permanent hot melt adhesive, ultrasonic weld or hot heat seal, etc. The nonwoven connector folds are releasably attached to each other by securement adhesive or ultrasound at 833.

In FIGS. 18 and 19 the tape tabs and the outer layers of each of the two-connector nonwoven are shown fastened to the inner surface of the diaper. Alternatively, the tape tabs and outer layer of each of the two connector nonwoven fasteners may be fastened to the outer surface of the diaper, in which case, the diaper may have to be reversed before use. Also, in FIGS. 18 and 19, the multifold tape tab consists of four folds although it may consist of more folds so long as the number of folds (n) is an even integer between 2 and 10. An even number of folds is necessary in order to insure inter-engagement of the hook and loop fasteners. If uneven number of folds are used, the hook and loop fasteners will not properly engage with one another. Also, the outer edge of the top layer and the outer edge of the bottom layer must be disposed toward the inner surface of the diaper.

The diaper shown in FIGS. 20A and 20B is similar to the diaper shown in FIGS. 17A and 17B except for the nonwoven connectors and the hook and loop arrangements. Thus, the diaper 900 comprises a front waist region 901 having two lateral ends or edges 901F, 901G, and a back waist region 803 having two opposing lateral ends or edges 903F, 903G. The respective adjacent opposed edges (i.e., 901F to 903F and 901G to 903G) are connected permanently to the nonwoven connectors 912 and 914, respectively, thus connecting the back waist of the diaper to the front waist of the diaper as shown in FIG. 20B. As is shown in FIGS. 20B, 20C and 20D, the nonwoven connectors 912 and 914 differ from the nonwoven connectors 812 and 814 in FIG. 17B in that each of the nonwoven connectors 912 and 914 has a perforated or weakened line such as 917 and 918, a hook strip 919 and a loop strip 921 disposed on the nonwoven connector 912 on each side of the perforated line 917 and, similarly, a hook strip 923 and a loop strip 925 disposed on the nonwoven connector 914 on each side of the perforated line 918. The diaper 900 comprises six side seals, four side seals 926, 928, 930 and 932 all permanently sealed to the diaper and two peelable lateral side seals as in FIG. 17. In order to put on the diaper when one has shoes or trousers on, the two lateral peelable side seals are torn, the perforated lines 917 and 918 are torn, the legs of the wearer are inserted through the leg openings, the front and back waist portions are wrapped around the waist of the wearer and the hook and loops on the respective nonwoven connectors are engaged into each other. FIG. 20C illustrates the sectional view 20C-20C before the perforated lines are torn, and FIG. 20D shows the engagement of the hook and loop after the perforated lines have been torn.

Figure 20:
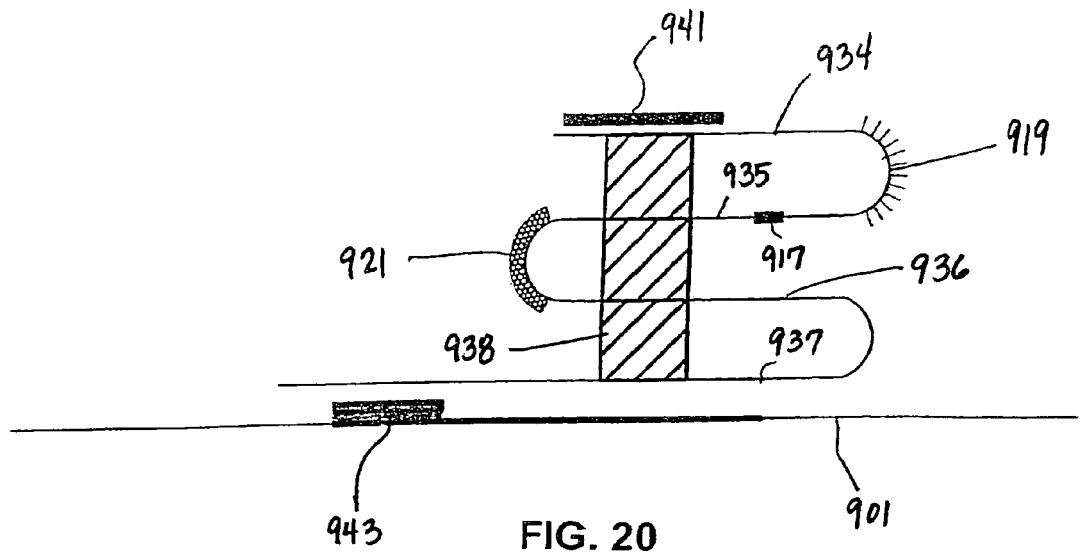
FIG. 20 is an alternate view of a tape tab fastener as in FIG. 18 prior to attachment on the inner front waist surface of the diaper.
Figure 21:
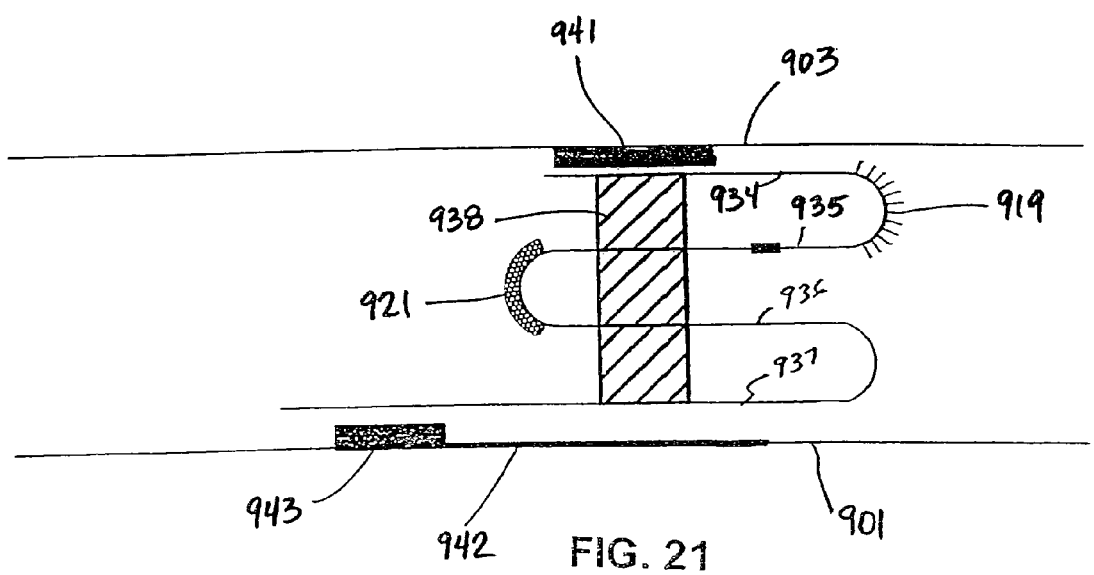
FIG. 21 is a view similar to FIG. 20 after folding the diaper showing the top and bottom layers of folded nonwoven permanently attached onto the back and front waist region.
Figure 22:
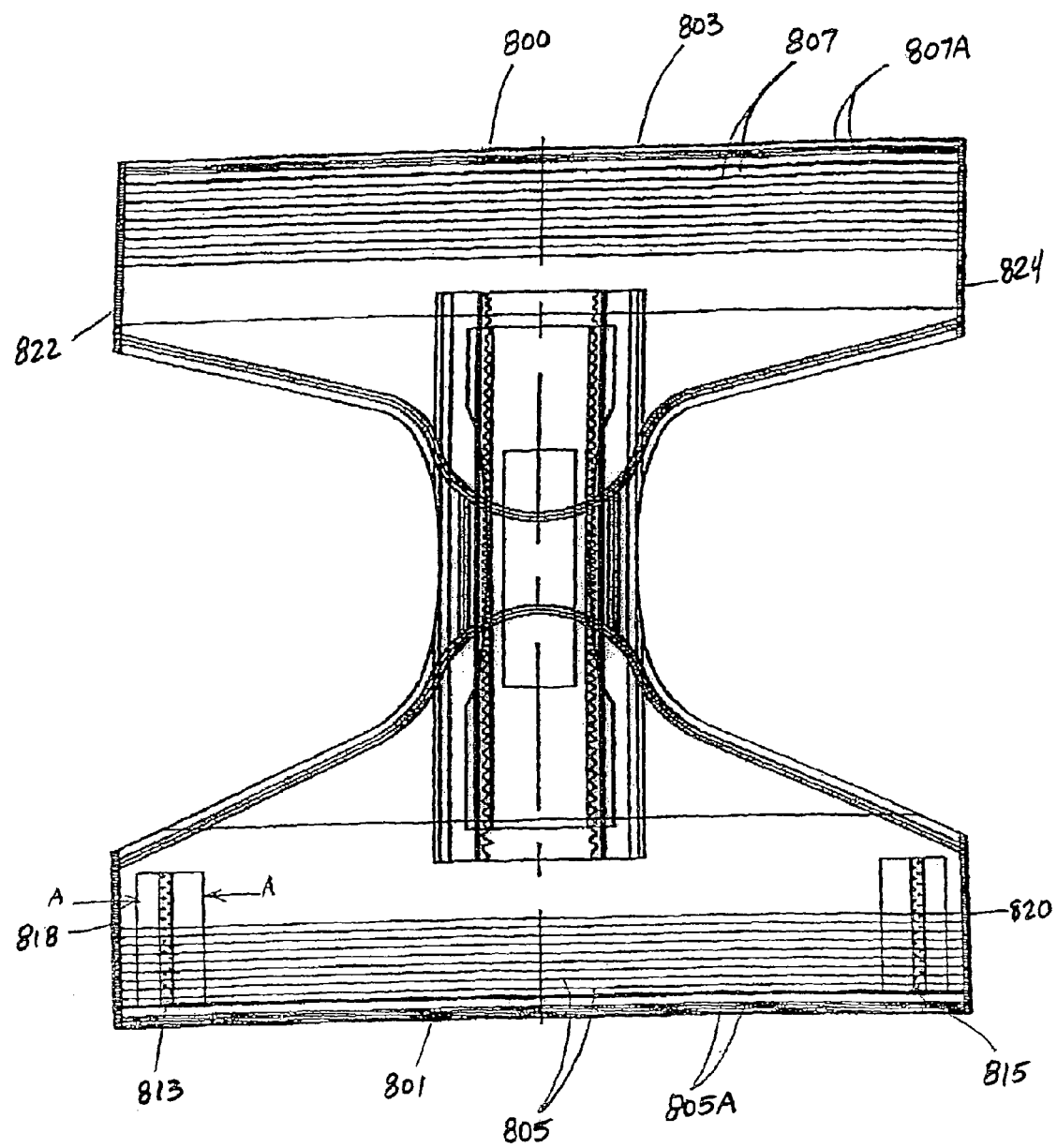
FIG. 22 is a stretched plan view of a pull-up diaper similar to FIG. 17 before final folding of the diaper.

FIGS. 20 and 21 show the tape tab construction for unfolded diaper (FIG. 20) and folded diaper (FIG. 21). Both figures show a multifolded tape tab with four folds 934, 935, 936 and 937 with a securement means 938. The hook fastener 919 is attached to the segment between the folded portions 934 and 935, and the loop fastener 920 is disposed on the side connecting the folded portions 935 and 937. The top fold 934 is permanently attached to the inner front waist portion 903 by the adhesive layers 941. Similarly, the bottom fold 937 is permanently attached to inner back waist side 901 of the diaper by the adhesive layer 942. As in the embodiments shown in FIGS. 18 and 19, a peelable glue layer such as 943 may be provided on the back waist 901. Also, a perforated line 944 is provided such that when the perforated line is torn, the hook and loop fasteners may be engaged into one another.

Figure 23:
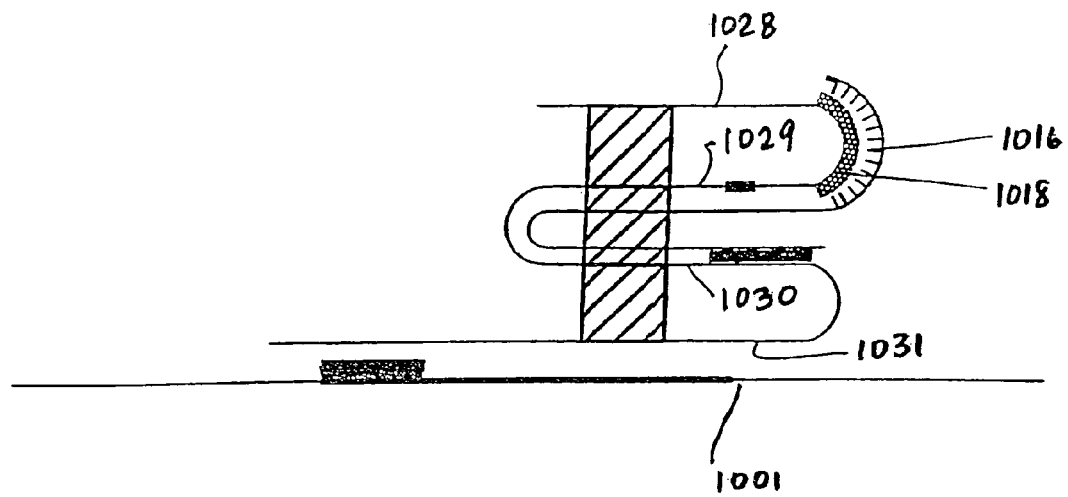
FIGS. 23 and 24 illustrate alternate construction of the tape tabs and hook and loop similar to FIGS. 20 and 21 but wherein the tape tabs are in prefastened position.
Figure 23A:
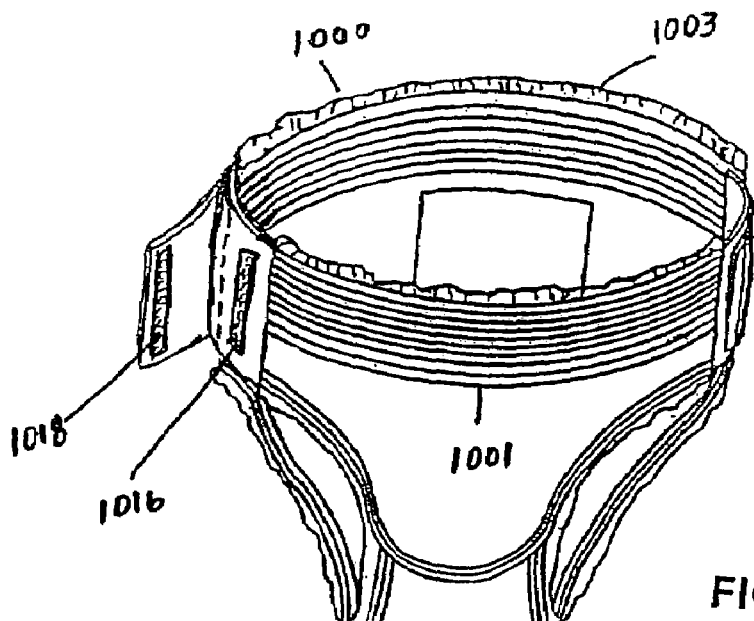
FIG. 23A is a front perspective view of the diaper similar to FIG. 21 with the hook and loop both disposed on the same nonwoven connector portion.
Figure 23B:
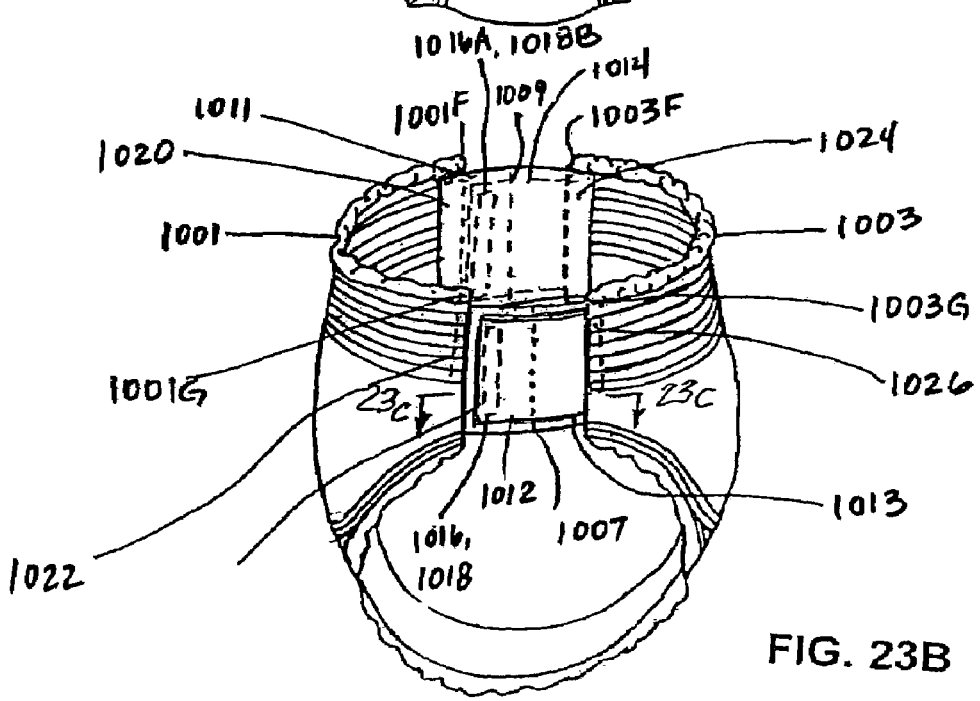
FIG. 23B is a right side view of the diaper shown in FIG. 23.
Figure 23C:
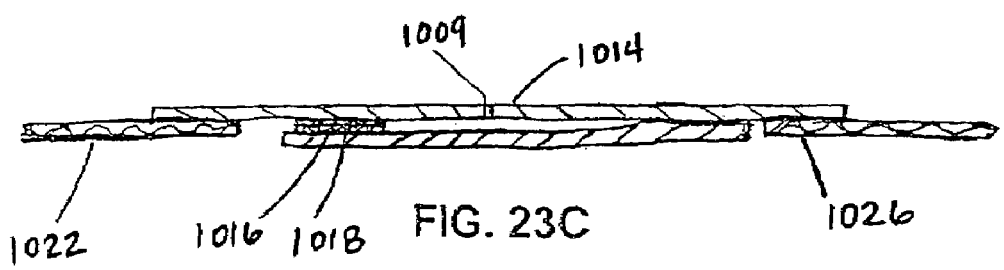
FIG. 23C is a sectional view taken along the line 23C-23C in FIG. 23B.

The diaper illustrated in FIGS. 23A and 23B is similar to the diaper shown in FIGS. 20A and 20B except that the diaper is in a prefastened condition. Thus, the diaper 1000 comprises the front waist region 1001 having two lateral ends or edges 1001F and 1001G, and a back waist region 1003 having two lateral ends or edges 1003F and 1003G. A first nonwoven connector 1011 connects the inside surface of the lateral edge 1001F to the inside surface of the opposed lateral end 1003F of the back waist portion, a second nonwoven connector 1012 connecting the inside surface of lateral edge 1001G of the front waist portion to the inside surface of the opposed lateral end 1003G of the back waist portion, a third nonwoven connector 1013 having a hook strip fastener 1016 on one side edge engages a loop strip fastener 1018 on said first nonwoven connector and having its opposed lateral edge permanently attached to the first nonwoven connector 1011, and a fourth nonwoven connector 1014 having a hook strip fastener 1016A on one if its side edges engages the loop strip fastener 1018A on said second nonwoven connector 1012 and its other side edge permanently attached to said second nonwoven connector 1012. As in the diaper 900 shown in FIGS. 20A, 20B the diaper 1000 of FIGS. 23A, 23B comprises four permanent side seals 1020, 1022, 1024 and 1026 as well as a two conventional lateral side seals as described in connection with FIG. 17 (818 to 822 and 820 to 824). Each of the nonwoven connectors 1012 and 1014 has a perforated or weakened line 1007, 1009 which can be torn when the diaper is to be worn or removed by a person having his shoes and/or pants on. The diaper shown in FIG. 23A may be worn in the same manner as the conventional diaper hereinbefore described.

Figure 24:
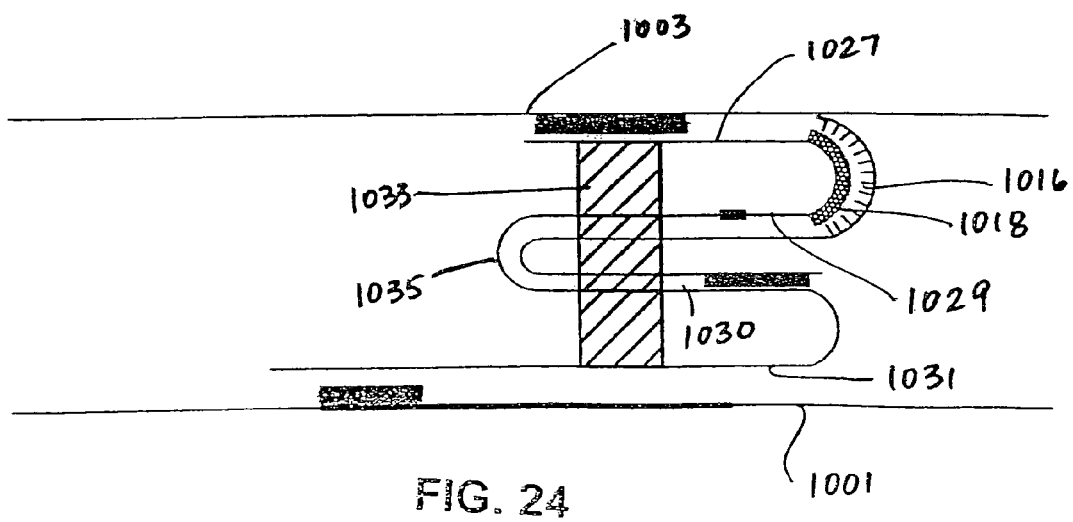

FIGS. 23 and 24 show folded tape tabs 1028, 1029, 1030 and 1031, hook strip fastener 1016 disposed on the nonwoven portion 1033 engaged with the loop strip fastener 1018 on the nonwoven 1035.

Figure 25A:
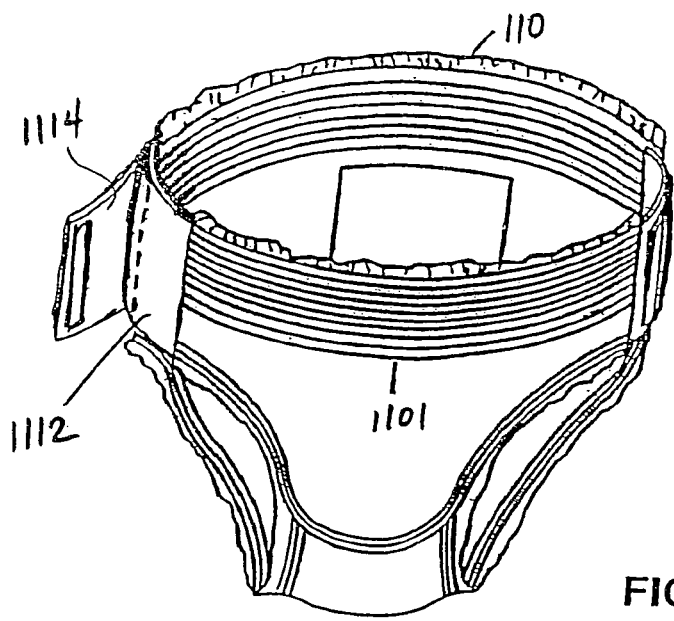
FIG. 25A is a perspective view of a diaper similar to FIG. 23 but wherein a surface of one of the nonwoven connector portions is a loop surface capable of engaging the hook fastener on the opposed surface of the other connecting web or panel.
Figure 25B:
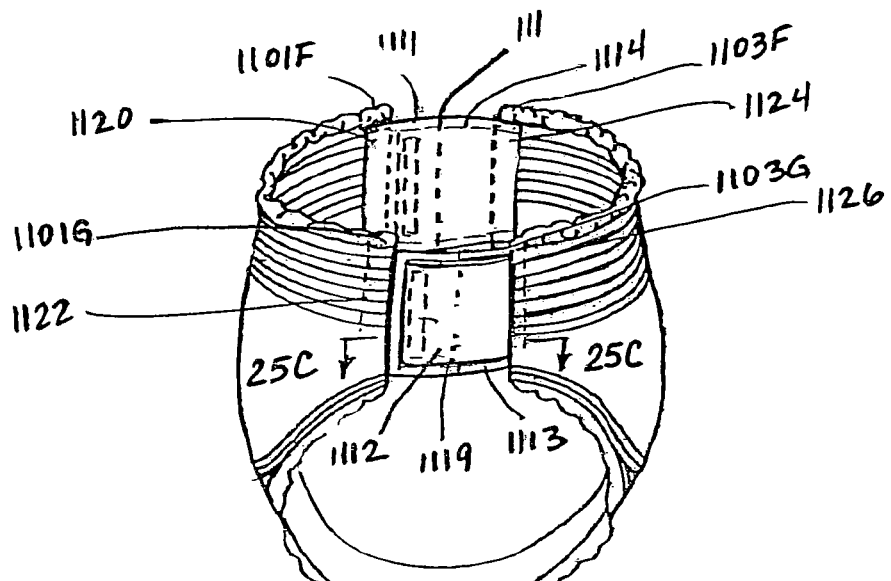
FIG. 25B is a right side view of the diaper shown in FIG. 25A.
Figure 25C:
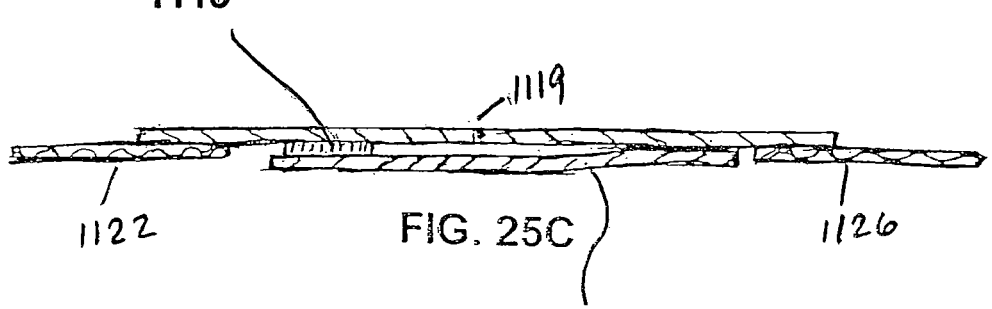
FIG. 25C is a sectional view taken along the line 25C-25C of FIG. 25B.

The diaper shown in FIGS. 25A, 25B is similar to the diaper shown in FIGS. 23A, 23B except that the surface of one of the nonwoven connectors itself is a loop surface capable of engagement with the hook fastener. As is shown in FIGS. 25A, 25B the front and back waist portions 1001,1003 are connected together by the nonwoven connectors 1111, 1112, 1113 and 1114. The nonwoven connector 1113 has a hook strip 1115 which engages the surface of the nonwoven connector. Each of the nonwoven connectors 1112 and 1114 has a perforated line 1118, 1119 which can be torn before wearing the diaper. Also, the diaper comprises four side seals 1120, 1122, 1124 and 1126 which are permanently attached to the diaper. In order to remove the diaper, as in the diaper of FIGS. 17A, 17B the two lateral peelable side seals are torn (if there be any) with the hook 1115 already attached to the loop surface of the nonwoven connector.

Figure 26:
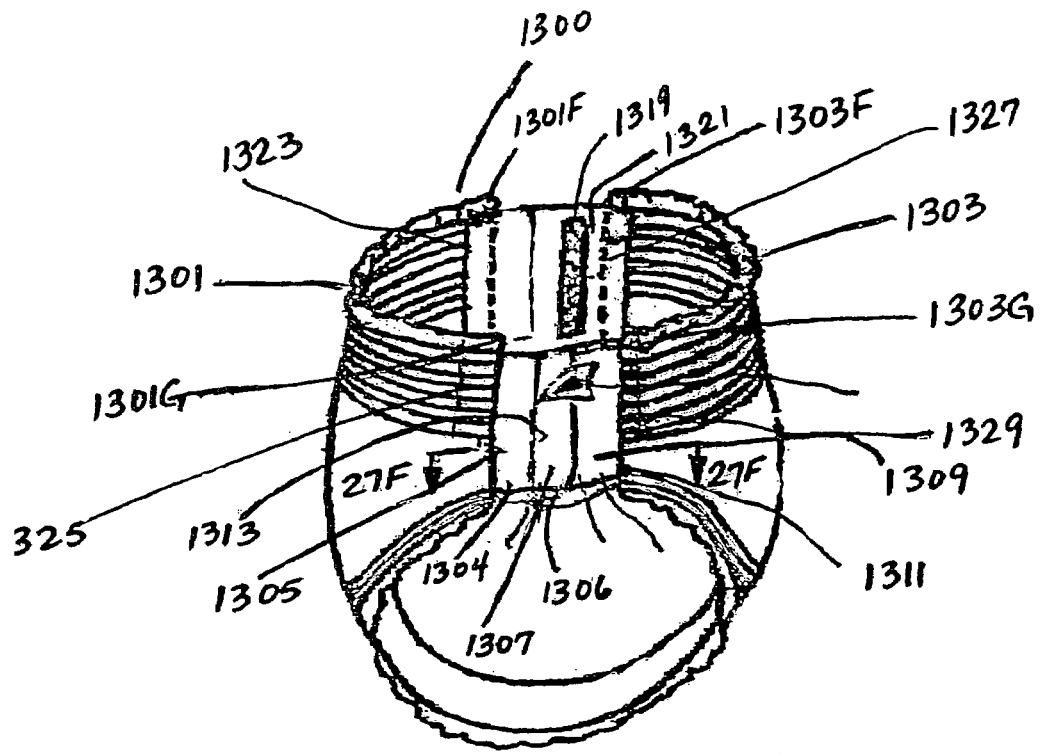
FIG. 26 is a side view of a diaper according to a further embodiment of the invention.

The diaper shown in FIG. 26 illustrates another embodiment of the invention. The diaper 1300 comprises a back waist portion 1301 having laterally opposed edges 1301F and 1301G, and a front waist portion 1303 having laterally opposed edges 1303F and 1303G. A first nonwoven connector portion 1304 has a first edge 1305 permanently sealed to the inside edge of the back waist portion and a second, opposed parallel free edge 1306 spaced away from said first edge having a loop strip fastener 1307 disposed on the outer surface of said second edge. A second nonwoven connector 1309 also has an edge 1311 permanently attached to the inside edge of the front waist portion and a second opposed parallel free edge 1313 spaced away from said sealed edge having a hook strip fastener 1317 (shown peeled away) disposed on the inner surface of the second nonwoven connector portion, adapted to engage the loop strip fastener 1307 when the second nonwoven connector portion overlaps the first nonwoven connector portion. A third nonwoven connection portion and a fourth nonwoven connection portion (not shown) are disposed opposite and behind the first and second connector portions which serve similar functions as the first and second connector portions to join the edges 1301F and 1303F by engagements of hook and loop fasteners 1319,1321.

In order to remove the diaper when a person has his shoes or pants on, the perforated lines of the nonwoven connectors are torn and the diaper is removed. In order to put on the diaper the peelable side seals (if there be any) and the perforated lines of the nonwoven connectors are torn, the tape tabs are unfolded and the diaper is put on as a conventional diaper and retained in position by using the fasteners.

Figure 27:
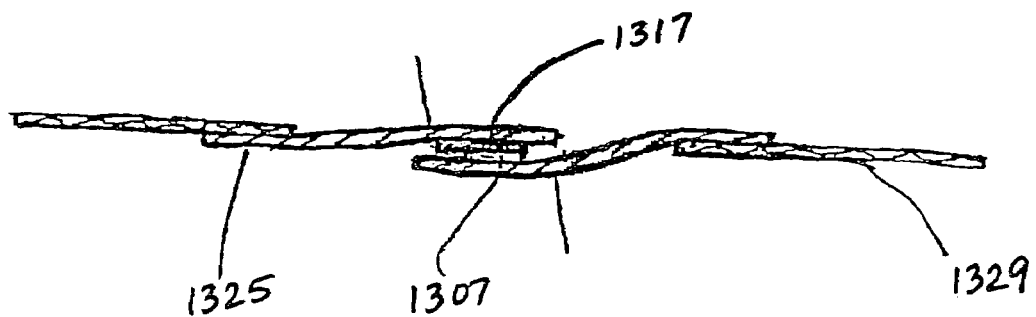
FIG. 27 is a sectional view taken along the line 20F-20F in FIG. 20E.

FIG. 27 shows the cross section 27-27 of FIG. 26 comprising two permanent side seals 1305, 1311 and a peelable side seal 1323 (pre-engaged hook and loop). Also there are three additional side seals (not shown) on the opposite side of the cross section 27-27. Therefore, the alternate construction shown in FIG. 26 has eight side seals, six as described above and two as the pull-up shown in FIG. 17. The latter side seals are optional and may be omitted.

In order to remove the diaper the hook and loop fasteners on the first and second connector portions are disengaged, and similarly the hook and loop fasteners on the third and fourth connector portions are disengaged. To wear the diaper the legs are inserted through the leg openings and the diaper is slipped on similar to pants because the hooks and loops are pre-engaged.

In FIGS. 6, 8, 10, 11, 14, 17A, 17B, 20A, 20B, 23A, 23B, 25A, 25B and 26 the products are illustrated without the two peelable side seals (818 to 822 and 820 to 824, as shown in FIG. 17). These side seals are optional and depending on product design and manufacturing process. For example, a pull-up may need these side seals to simplify production of the product, whereas a conventional diaper may not need these side seals.

Although several embodiments of the present invention have been illustrated with pull-up diapers, the invention is also applicable to conventional diapers and other absorbent articles of the types described in copending patent application Ser. No. 10/346,607 filed Jan. 17, 2003, and in U.S. Pat. Nos. 3,592,194; 3,945,386; 4,029,100; 4,050,462; 4,253,461; 4,388,075; 4,579,556; 4,636,207; 4,695,278; 4,719,261 and 5,278,100.

The nonwoven connector may be conventional nonelastic nonwoven such as spunbonded, thermally bonded, chemically bonded, hydro-entangled, or similar nonwovens. Also the nonwoven connector may be elastic nonwoven or composite elastic nonwoven made of a film or an elastic film sandwiched between two layers of nonwovens such as the ones described in copending application Ser. No. 10/346,607 filed Jan. 17, 2003, or as the elastic nonwovens manufactured by Tredegar, Fibriflex 400, Fibriflex FAB 307, Clopay 95033001, p 18-5479 or p 18-5478. The nonwoven connectors may be of any length, width or basis weight. Also, while reference is made to the use of nonwoven connectors, wings, side panels and tape tab fasteners may be interchangeable with nonwoven connectors.

The nonwoven connectors as identified above and the product outer surface are conventional nonwovens such as spunbond nonwoven made of polypropylene fibers manufactured by First Quality Products, Inc., McElhattan, Pa. or Fiber Web BBA Nonwovens, and Sofspan 200 series or 120 series available from BBA Nonwovens, Simpsonville, S.C., or similar nonwovens weighing 0.5 to about 2 ounce per yard square.

The folded or unfolded nonwoven connectors may be attached to an absorbent article (pull-up, conventional briefs, undergarments) as follows:

1) The nonwoven connectors are attached to the inner surface of the product. In this case, the inner lateral edges of the front waist is connected to the outer lateral edges of the back waist.

2) The nonwoven connectors are attached to outer surface of the back waist and the outer surface of the front waist lateral edges. The end product is the same as in 1 above, the only difference is that the area of the nonwoven connector that is attached to the outer surface of the product will not come in contact with the user's skin.

Figure 28:
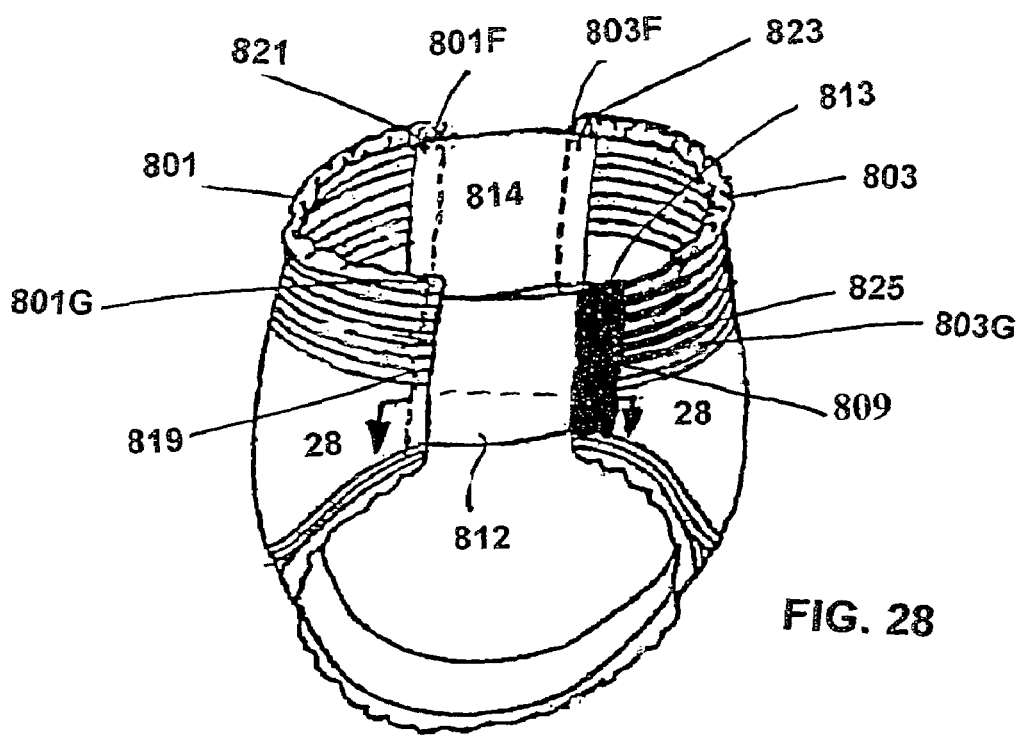
FIG. 28 is a perspective view of another embodiment showing a modification of the article illustrated in FIG. 17B.
Figure 28A:
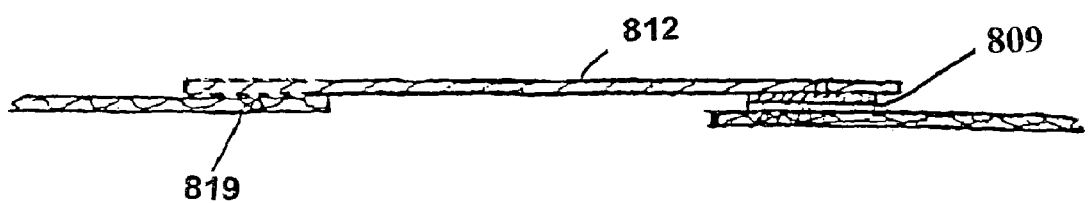
FIG. 28A is a sectional view taken along the lines 28-28 of FIG. 28.

3) The same as 1 and 2 above with the exception that only one of the edges of the nonwoven connector is attached permanently to the product back waist lateral edges (inner or outer surface). In this case, a hook fastener is attached to the nonwoven connector such that the hook fastener engages the loop strip on the front waist lateral edge of the absorbent article front waist outer or inner surface as shown by FIGS. 28 and 28A. Thus, the product may be prefastened or not prefastened. The user can put the product on identical to conventional diapers as described in copending application Ser. No. 10/346,607 filed Jan. 17, 2003, or put the diaper on identical to a pull-up diaper.

FIG. 28 is a perspective view of a diaper similar to FIG. 17B except that the nonwoven connector 812 is permanently attached to the inner surface of the lateral edge 801G of the back waist region 801. In this construction, the diaper is not provided with the loop 809 but only with the hook 813 which engages the nonwoven surface (the front waist outer surface). If desired, however, a loop fastener may be included as in FIG. 17B.

Figure 40A:
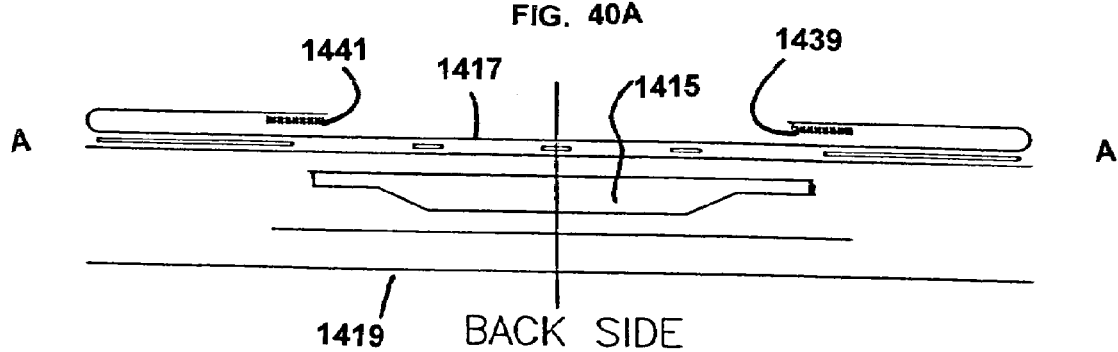
FIG. 40A is a cross section of FIG. 40 taken the along A-A.
Figure 40:
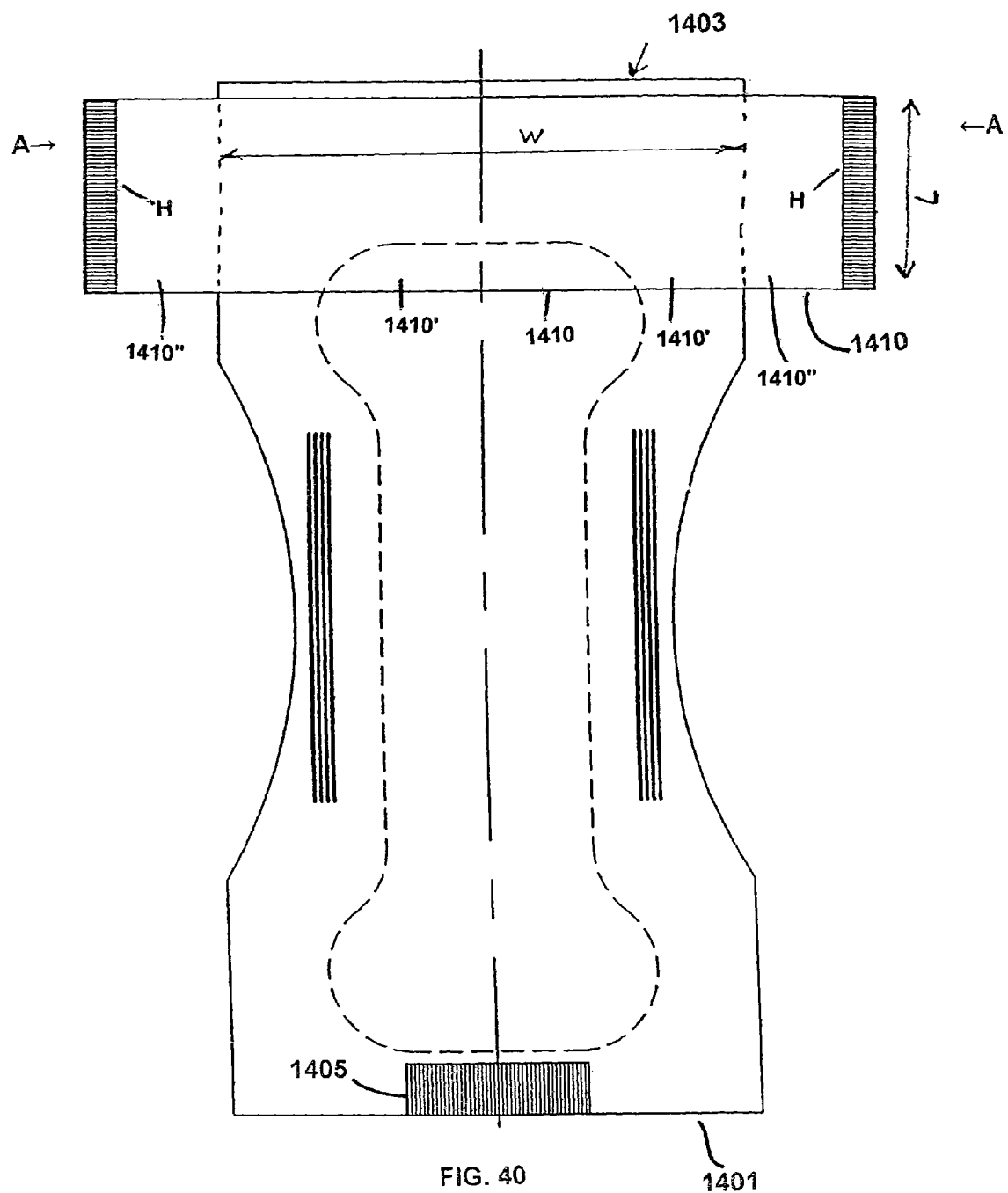
FIG. 40 is an alternate construction wherein the nonwoven connectors are one piece.

Referring to the drawings (e.g., FIG. 30), the nonwoven connectors or wings 1411, 1413 may be partly elastic (2-3 pieces attached together, elastic and non-elastic). Thus, a portion of the nonwoven connector may be an elastic substrate similar to the elastic nonwoven available from Tredegar, Fabriflex FAB 307 or 400 elastic nonwovens. The other portion of the nonwoven may be non-elastic, 15-50 GSM nonwoven such as available from First Quality Products, Inc. as conventional point bonded spun bonded nonwoven, pillow bonded or modified pillow bonded nonwoven. Preferably, only the portion of the nonwoven connector that is non-elastic is attached to the absorbent article for reasons of economy. Also, as shown in FIG. 40, the nonwoven connector may consist of three portions with the middle portion being a non-elastic strip 1410' attached permanently to the absorbent article, and the portions on each side may be elastic nonwoven 1410". The nonwoven connector may be one integral piece or three pieces joined together, if desired, with the middle piece 1410' being non-elastic and the side portion 1410" being elasticated.

Figure 29:
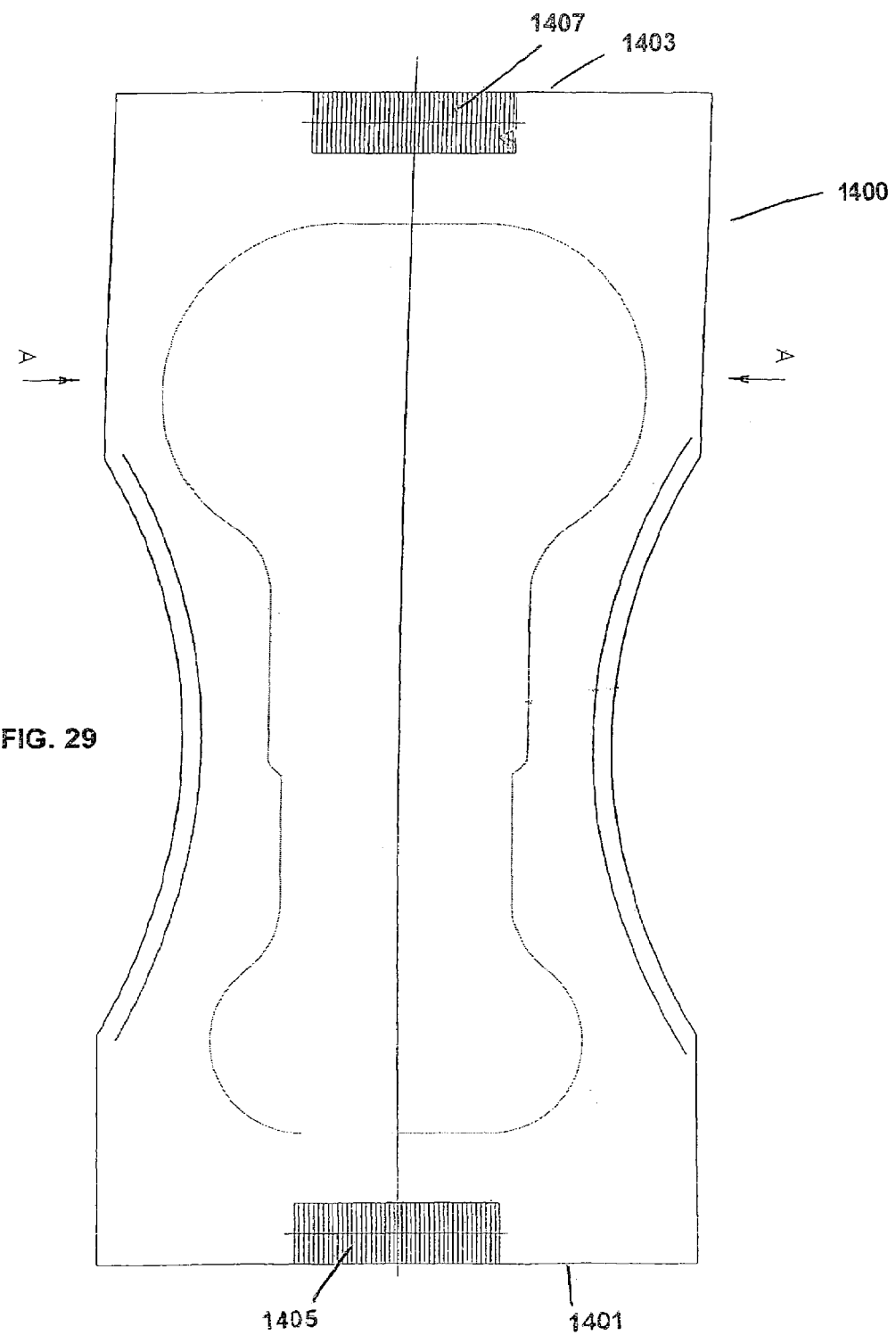
FIG. 29 is a stretched plan view of alternate conventional diaper similar to the diaper shown in FIG. 14 showing a partly elasticated portion on the front waist region and back waist region.
Figure 32:
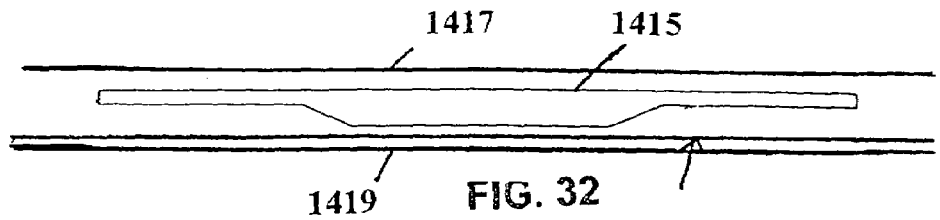
FIG. 32 is a sectional view taken along line A-A of FIG. 29.

With reference to FIGS. 29 and 32, the nonwoven connectors 1411 and 1413 (wings or side panels) may be permanently attached to the lateral sides of the absorbent article which are fluid pervious or impervious. It is preferable, however, to attach the nonwoven connector the fluid/air permeable lateral sides in order to enhance breathability.

Figure 41:
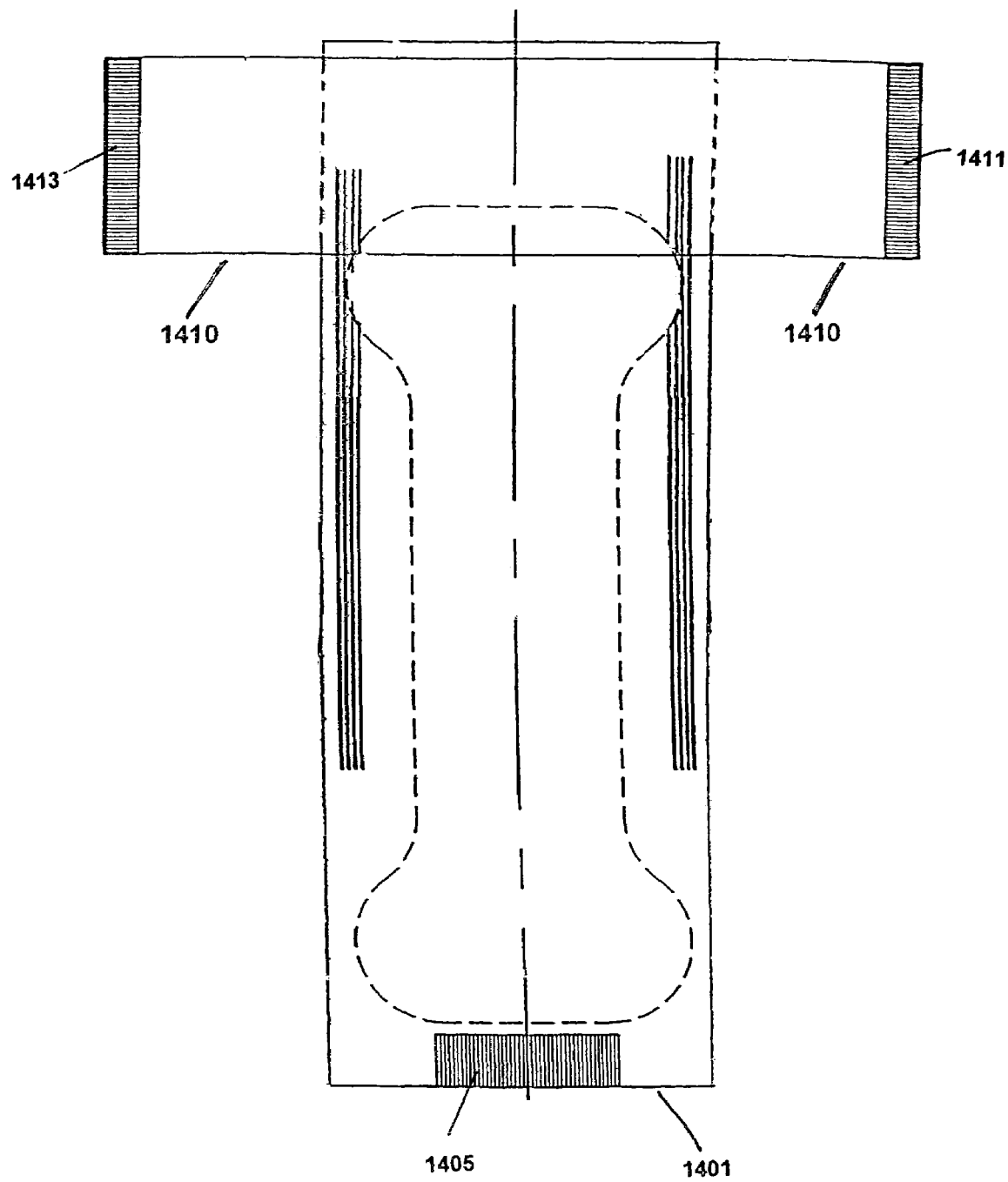
FIG. 41 is another construction of FIG. 40 wherein the crotch elastics extend to the nonwoven connectors.

The end of the nonwoven connector which is permanently attached to the absorbent article has a length L of from about 0.5 to about 15 inches and a width W of up to about 30 inches (see FIGS. 40 and 41). The entire length and a part of the width W of the nonwoven connector may be permanently attached to the absorbent article. It is preferable, however, that a segment of the nonwoven connector width W be free, i.e., not permanently attached, in order to enable or assist the wearer of the article in fitting it around the waist. Also, it is desirable to have the area of the nonwoven connector that is not permanently attached to the article, i.e., the area that does not extend beyond the lateral sides of the article, be releasably attached to the article. Such releasable adhesion can be accomplished by a low tack adhesive, hook strips, cohesive adhesives, etc. FIG. 40 shows the nonwoven connector 1410 attached to the article along its length L and part of its width W.

Figure 39:
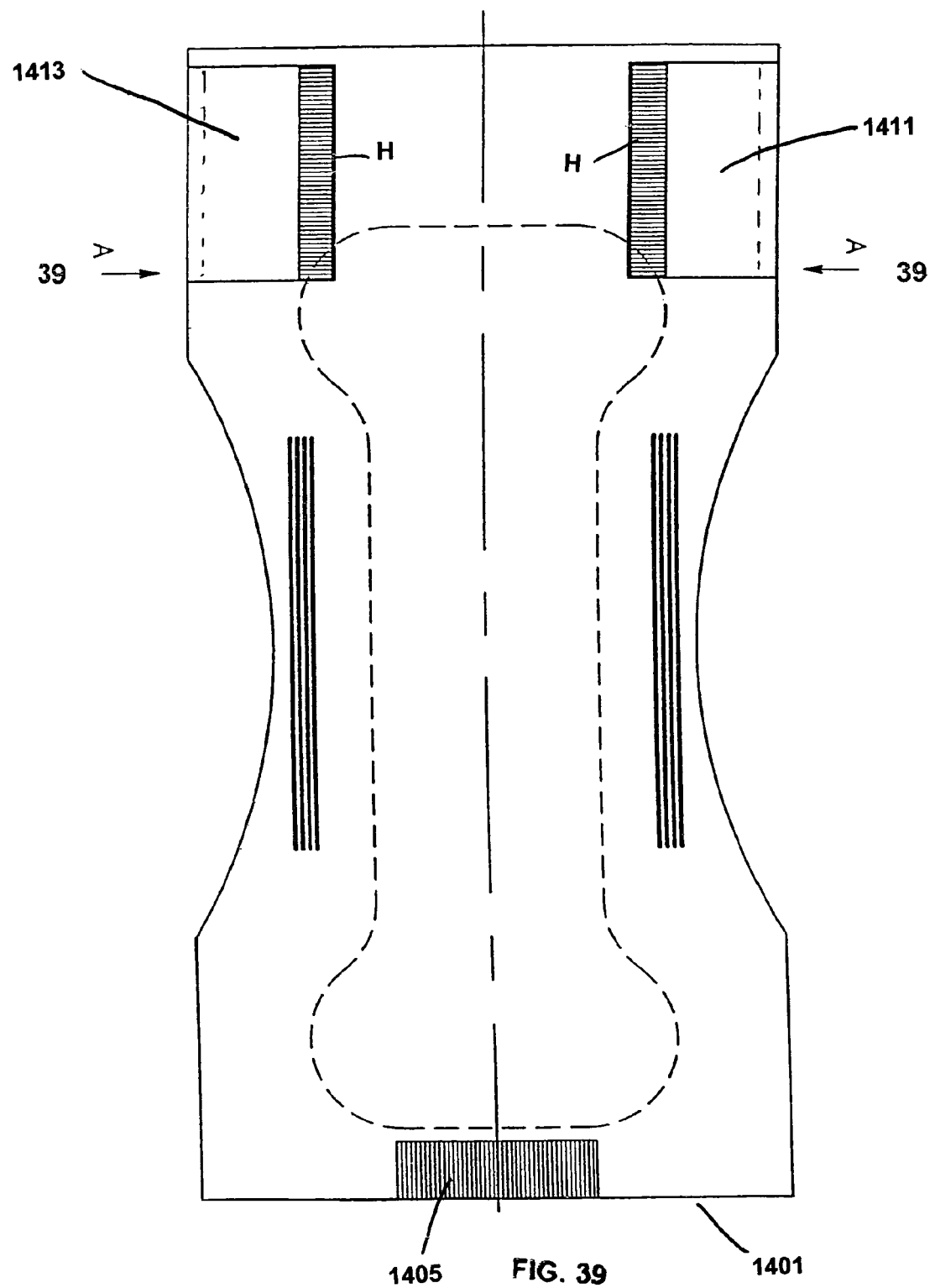
FIG. 39 is a stretched view of an alternate construction showing that the nonwoven connectors are attached to the chassis between the cover sheet and the backing.
Figure 39A:
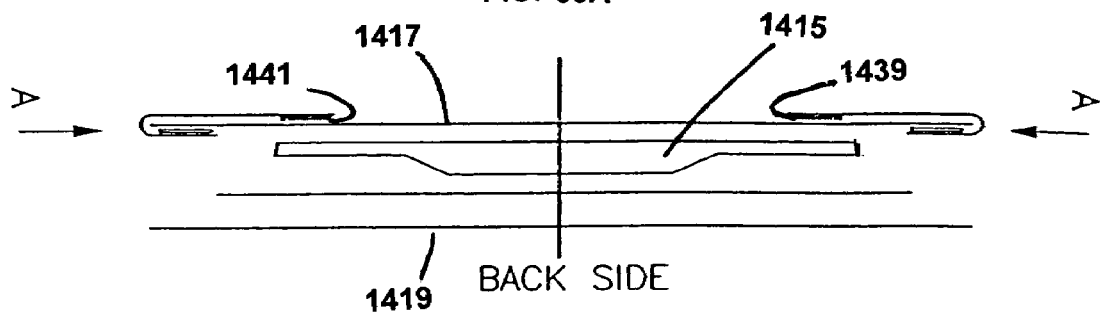
FIG. 39A is a cross section of FIG. 39 taken along the line 39-39.
Figure 39B:
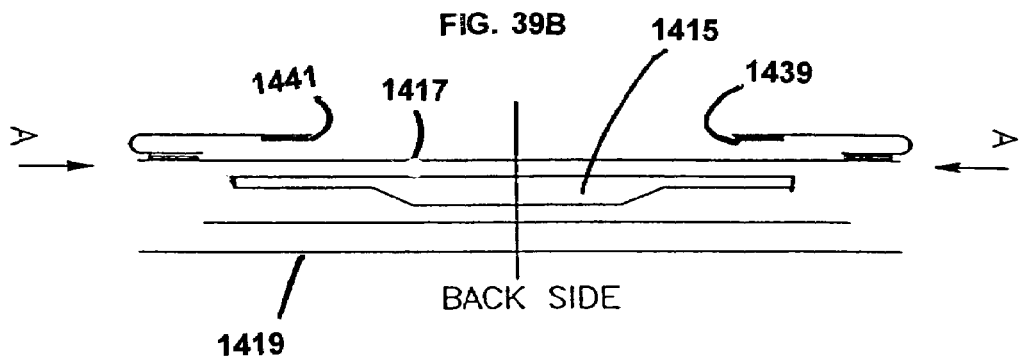
FIG. 39B is a cross section of FIG. 39 showing the nonwoven connectors or wings attached on the top surface of the coversheet.

In order to simplify the manufacture of the absorbent article, each of the two nonwoven connectors or wings may be a single piece, with its central area attached to the inner or outer surface of the article back waist, and the sides extending out of the lateral ends of the article may be attached releasably, or preattached releasably, to the absorbent article front waist outer surface. This nonwoven connector or wing may be several pieces of elastic and non-elastic nonwovens attached together. In either case the unattached nonwoven connectors/wings may be folded on or under the absorbent article surface as shown in FIGS. 39A, 39B, 39C or folded as Z or C folds similar to the folds described in copending application Ser. No. 09/891,976 filed Jun. 26, 2001. A hook strip H as in FIG. 40 or tape tab type hook fastener is attached to each outer end of the nonwoven connectors or the wings lateral ends. Also, a hook strip or tape tab type hook fastener may be attached adjacent to the insert front waist lateral sides. This allows using the product similar to conventional absorbent articles (diapers, pull-ups) or T-shaped diapers. Optionally, strips of loops may be used on the insert front waist to engage the hooks H.

The method of manufacturing the products shown in FIGS. 29-41 are basically the same as the method described in commonly assigned copending application Ser. No. 10/266,420 filed Oct. 8, 2002, the disclosure of which is fully incorporated herein by reference. The method described therein is directed to a pull-up type absorbent article as shown in FIGS. 1-28A. The product is made such that the product's longer axis is perpendicular to the machine direction.

Figure 36A:
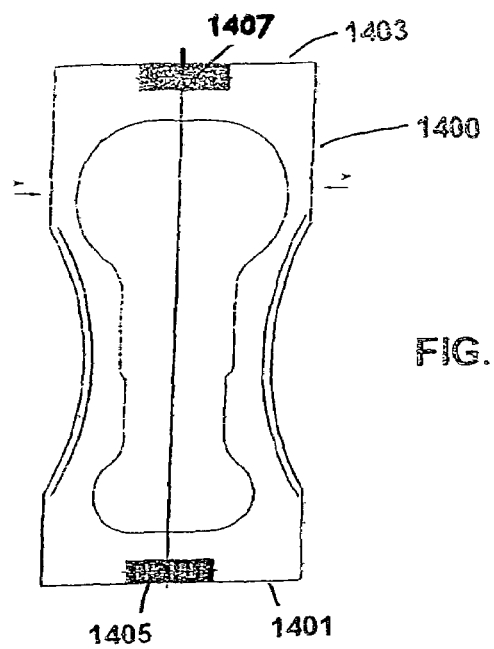
FIGS. 36(a), 36(b) 36(c) illustrate the diaper at different stages during its manufacturing operation.
Figure 36B:
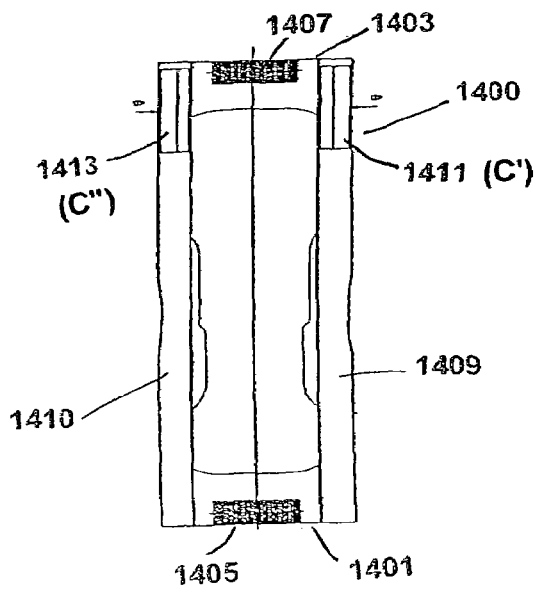
Figure 36C:
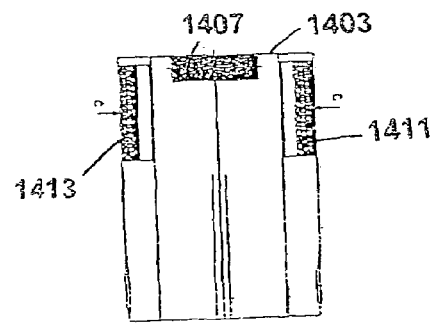
Figure 37:
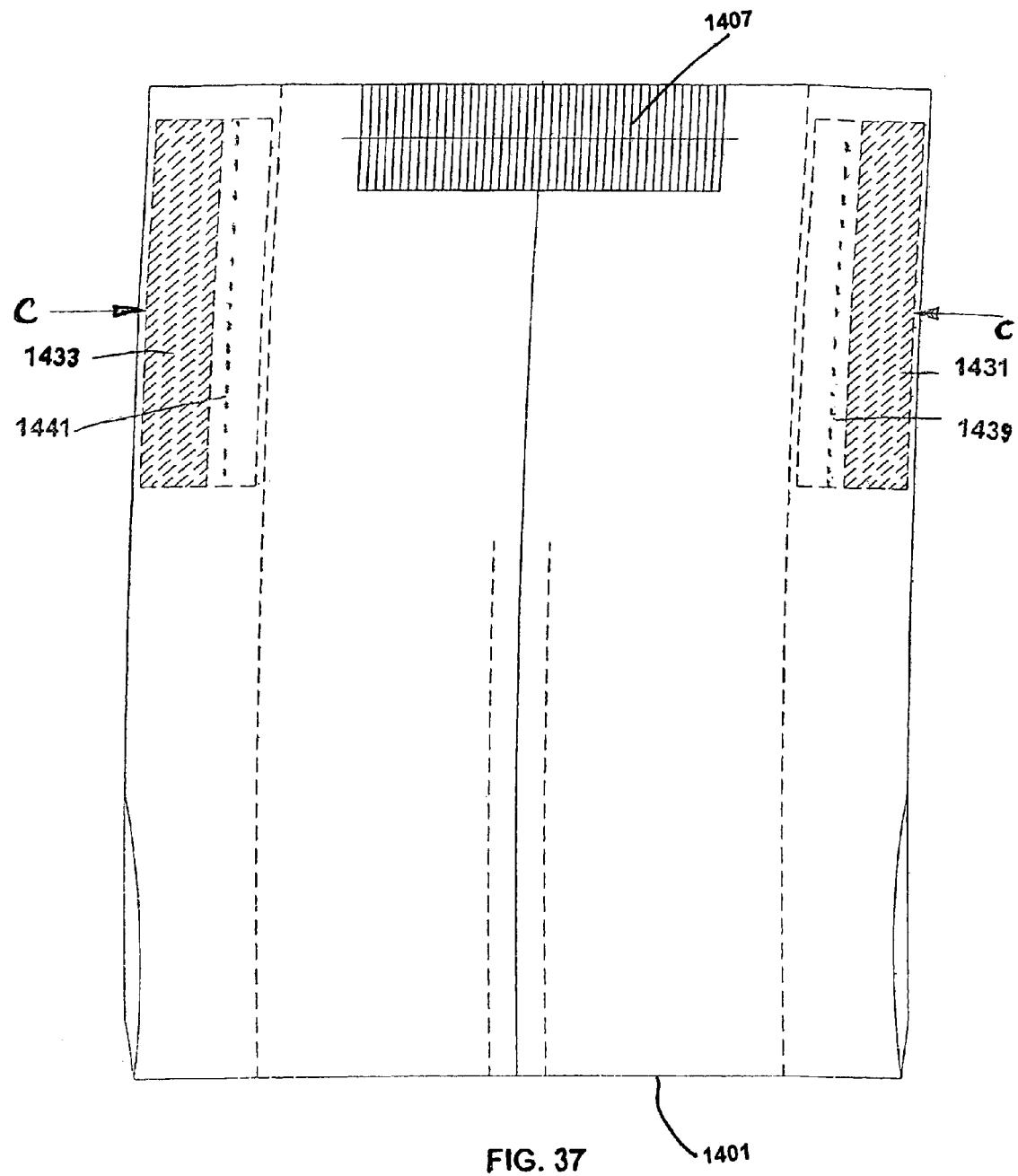
FIG. 37 illustrates a diaper as in FIG. 31 except that each of the nonwoven connectors comprises a perforated weakened line.
Figure 38:
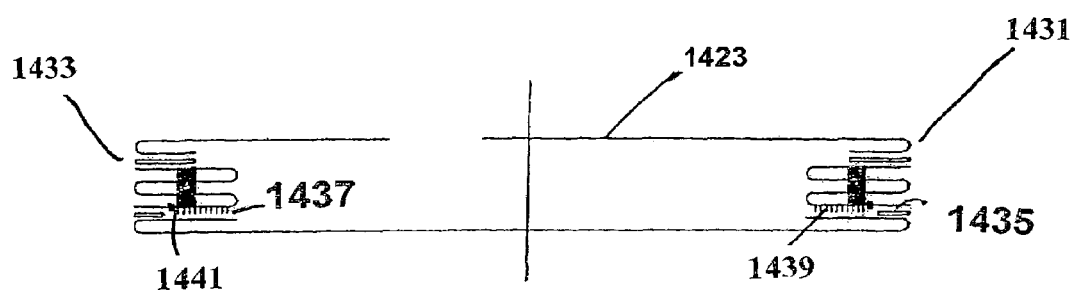
FIG. 38 is a sectional view taken along the line C-C of FIG. 37.

The method of making an absorbent article as illustrated in FIGS. 1-28A is as follows:

A. the product chassis is advanced such that the product length is perpendicular to the machine direction, B. a web of nonwoven connector is advanced perpendicularly to the direction of travel of the product chassis, C. the nonwoven connector is slit in two web portions C' and C" as shown in FIG. 36(b), D. one hook strip is attached to one of the edges of each of the nonwoven connectors of the web portions C' and C", E. the web portions C' and C" are folded such that the nonwoven connector edge without hooks is on the top surface, F. the top surface of each web portions C' and C" is coated with a suitable adhesive, G. each of the webs C' and C" is coated with a suitable adhesive, H. the product chassis web referred to in A above is advanced in parallel but opposite direction to the web such that the product outer surface (garment side) is the top surface of the web, I. each of the web portions C' and C" is rotated 90 degrees and advanced parallel to the direction of the webs in step H above, and then turned 180 degrees (flipped over) such that the adhesive surface becomes the bottom surface and attached onto the outer surface of the lateral edges of the product back waist area, and the web is then passed under a pressure roll (or a nip roll) in order to secure the nonwoven connector on the product outer surface, and J. the product is folded in the longitudinal direction, the lateral product side seals are sealed and the product is cut to the desired sized.

Optionally, the nonwoven connectors may be attached to the outer nonwoven instead of on the product chassis as described in method steps A and H, and the nonwoven connectors may be initially two separate rolls.

The method of making an absorbent article shown in FIGS. 29-41 is set forth below:

1. the product chassis is advanced such that its width is perpendicular to the machine direction axis, 2. the longitudinal sides of the product chassis are folded upwardly (see FIGS. 30 to 36C) and the folds are kept in place releasably by a suitable adhesive or other means, 3. the method is continued as in method steps A to G described above in connection with the method of making an article as in FIGS. 1-28A except that the bottom surfaces of the web portions C' and C" are coated with adhesive, 4. each of the individual webs C' and C" is attached on the longitudinal product back waist outer surface (lateral sides top surface of the product with folded sides) and passed under a press (or nip roll) to improve the securement of the nonwoven connector on the product sides, and a strip of hook is attached on the top surfaces of each of the nonwoven connectors, 5. the product is laterally folded such that the hook surface on each nonwoven connector engages the lateral side edges of the front waist (body facing) surface as shown by FIGS. 31 to 35.

Figure 34:
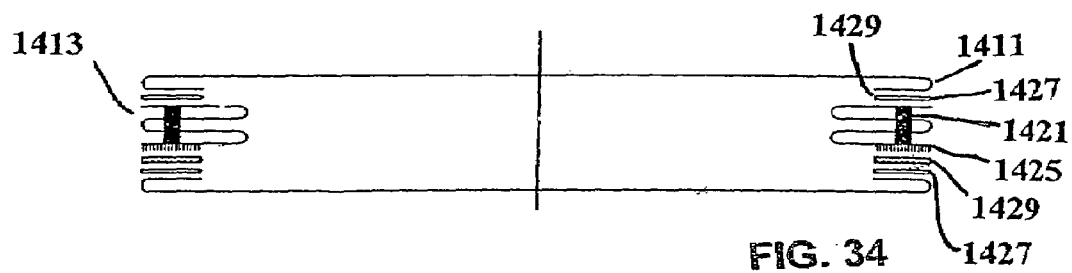
FIG. 34 is a sectional view taken along line C-C of FIG. 31.

6. In an alternative method, a strip of loop material may be attached on the top surface of each hook such that the surface of the hooks engage the surface of the loops and the upper surface of the loops are coated with a suitable adhesive. When the product is laterally folded as in step 5 above, the adhesive on each loop surface attaches permanently to the lateral sides of the front waist body side surfaces as shown in FIG. 34.

7. As a further option, the four nonwoven connector edges may be permanently attached to the product back and front waist surfaces and a perforation line may be provided before folding the nonwoven connectors as shown at 1439 and 1440 in FIGS. 36 and 37. In this case, the user may put on the product similar to a pull-up. To remove the product, the perforation lines may be torn and to the put the product on without removing the shoes the perforation lines art torn and the product put on similar to conventional diapers by utilizing the hook fastener to fasten the product around the waist. A strip of loop may be provided if desired.

8. As another option, instead of folding the product sides once inwardly as described above in step 2, the sides of the product may be folded once inwardly and once outwardly or as many folds needed to simplify manufacturing production.

Also, the hook can be selected such that it engages well to the nonwovens used in the product-nonwoven used on inner surface of the product or on the outer surface of the product. Thus, there will not be any need to have strips of loops attached onto the outer surface of the front waist. However, it is sometimes desirable for the product to have strips of loops in order to assure that the hooks will stay engaged to the loop strips. Therefore, in the above mentioned absorbent article constructions, a strip loop can be attached on each of the front waist lateral side edges (outer surface) as shown in FIGS. 28 and 34. The loop strips may be 1 to 7 inches wide, up to the same length as the product side seals or wing length. For example, the pull-up side seals length may be 3 to 9 inches.

The loop strips are preferably longer than the hooks in order to facilitate the product usage. These strips can be put on the product front waist at any place during product manufacturing. Also, as shown by FIG. 34 the loops may be attached on the top surface of the hooks (the hooks surface must engage the loop surface) in any of the above process steps before the final product fold as in FIG. 35. The nonactive (the back surface of the loop) surface of the loop may be preadhesive coated, or the adhesive can be added during the above process steps.

The absorbent articles shown in FIGS. 1-28 have been described in connection with a pull-up article. However, the invention is also applicable to other absorbent articles such as breathable absorbent articles as described in copending application Ser. No. 09/302,335 filed Apr. 30, 1999; copending application Ser. No. 09/376,282 filed Aug. 18, 1999; copending application Ser. No. 09/544,092 filed Apr. 6, 2000 and copending application Ser. No. 09/844,726 filed Apr. 27, 2001, all said applications being commonly assigned applications, and U.S. Pat. Nos. 3,592,194; 3,945,386; 4,029,100; 4,050,462; 4,253,461; 4,388,075; 4,579,556; 4,636,207; 4,695,278; 4,719,261; and 5,278,100.

In the pull-up diapers illustrated by FIGS. 1-28, the diaper has elastic elements in the front waist and the back waist, in the crotch area and the thigh belly region. In the diapers shown in FIGS. 29-41, the lateral edges of the front waist are attached to the lateral edges of the back waist. In this construction, the diaper has elastic elements in the front waist area and the crotch regions only. The present invention thus applies to any absorbent article of the type described in the aforementioned copending patent applications, and in the aforementioned patents.

The nonwoven connector may be conventional nonelastic nonwoven such as spunbonded, thermally bonded, chemically bonded, hydroentangled, or similar nonwovens. Also the nonwoven connector may of a film or a elastic film sandwiched between two layers of nonwovens such as the ones described in our above patent applications, or as the elastic nonwovens manufactured by Tredegar, Fibriflex 400 or, Fibriflex FAB 307 or Clopay 95033001 or p 18-5479 or p 18-5478.

The nonwoven connectors' outer surface as identified above and the product outer surface is covered with conventional nonwovens such as spunbond nonwoven made of polypropylene fibers available from First Quality Products or Fiber web Sofspan 200 series or 120 series or softex 21281-101 series or similar nonwovens having 2-13 ounces per square yard.

The nonwoven connectors may be prefolded, releasably attached to the folds together and then attached to the product permanently (one of its edges or both edges depending on whether the nonwoven connector is attached to the inner or outer surface of the product).

Also, it has been found that the hook length and width play a significant role in its engagement power depending on its peel and shear strength. A hook having a 2-inch length (parallel to product length) and 1 inch width has enough peel strength and shear strength to hold the product on the product user.

For a prefastened product, the nonwoven connectors have two lateral edges when the product is fully stretched. The first lateral edge is connected to the inner or outer surface of the back waist adjacent to outer lateral edge of the product and the second edge of the nonwoven connector is connected to the inner or outer surface of the front waist surface adjacent to the lateral edge of the front waist. The first and the second edges of the nonwoven connector face respectively toward the inner or outer surface of the product longitudinal centerline.

If both lateral edges of the nonwoven connector are permanently attached to the product, the product will resemble a pull-up. The user thus can slip on the product. If only one side of the nonwoven connector is attached permanently to the product then it is necessary to attach a male hook to the second lateral edge of the nonwoven connector. Thus, the user can put on the product on similar to conventional diapers. Also, such product can be put on similar to the T-shape product as described in said copending application Ser. No. 09/376,282 filed Apr. 6, 2000. Also, as previously stated, utilization of loop fastener is optional, if the product has male fastener similar to the Binder #42-288-HX-200-PP3.

The diaper 1400 shown in FIG. 29 has a front waist region 1401; a back waist region 1403 wherein the front waist region comprises a partly elasticated portion as in 1405 and the back waist region comprises a partly elasticated portion 1407. These elastics are optional.

Figure 30:
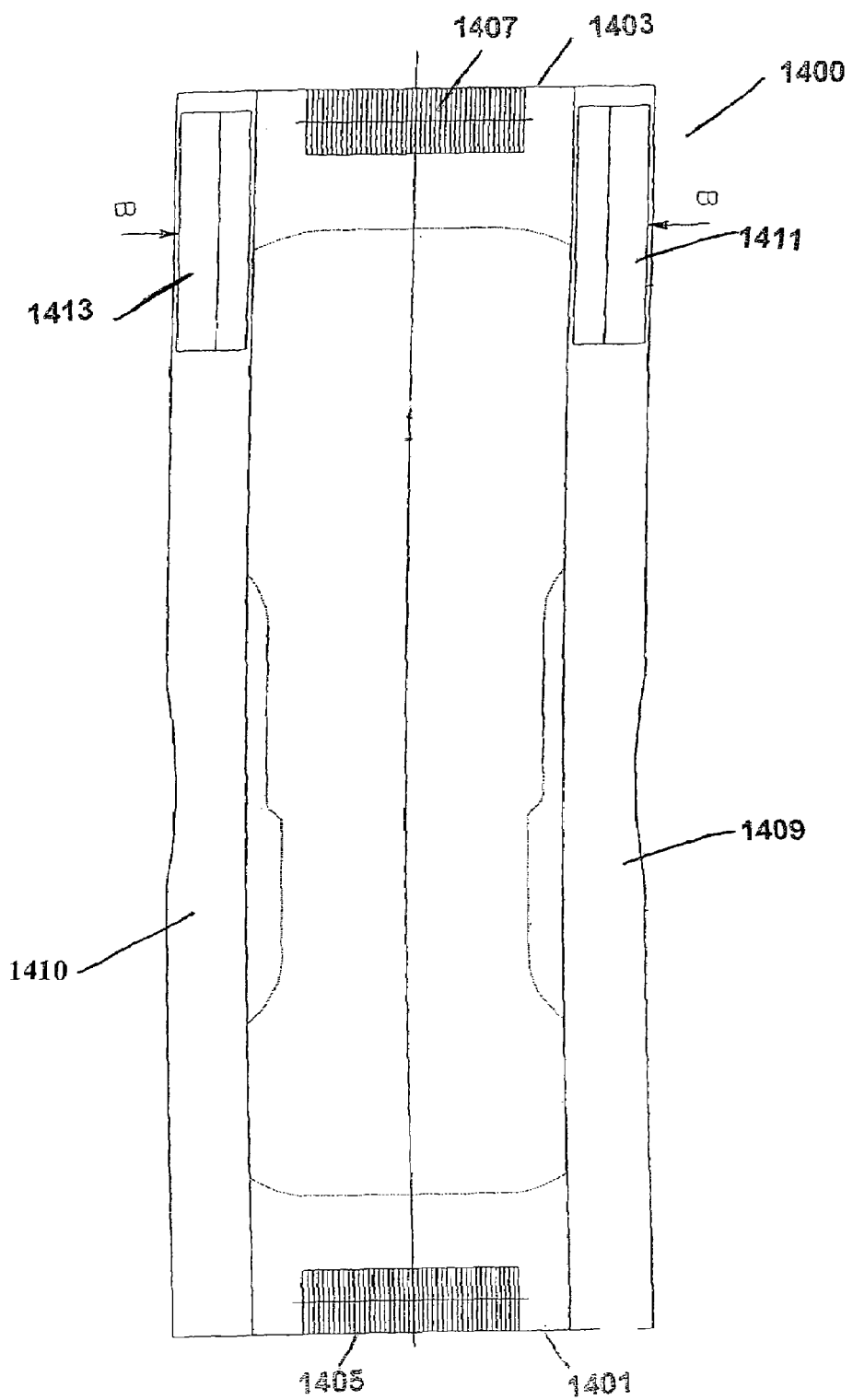
FIG. 30 illustrates a diaper similar to FIG. 29 but showing longitudinal side folds and different arrangement of nonwoven connector's attachments.
Figure 33:
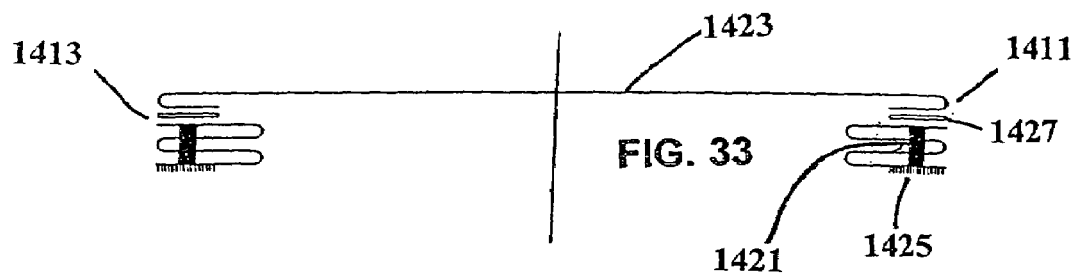
FIG. 33 is a sectional view taken along line B-B of FIG. 30.
Figure 35:
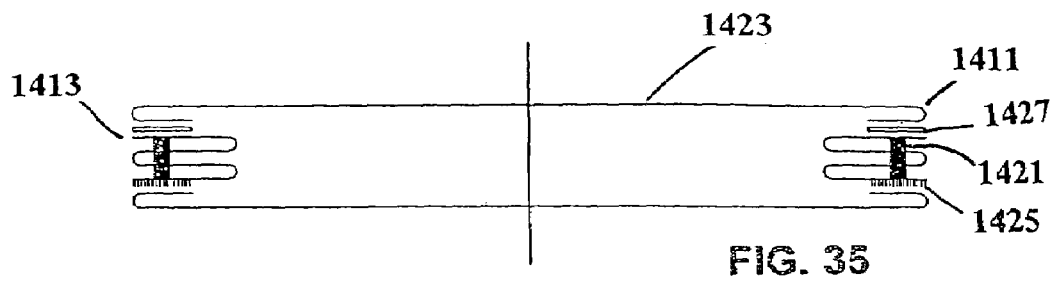
FIG. 35 is a view of an alternate construction of the diaper of FIG. 33.

FIGS. 30 and 33 show the diaper 1400 having folded longitudinal sides 1409,1410 and nonwoven connectors 1411-1413 and hooks attachment arrangements as shown in FIGS. 33, 34 and 35.

Figure 31:
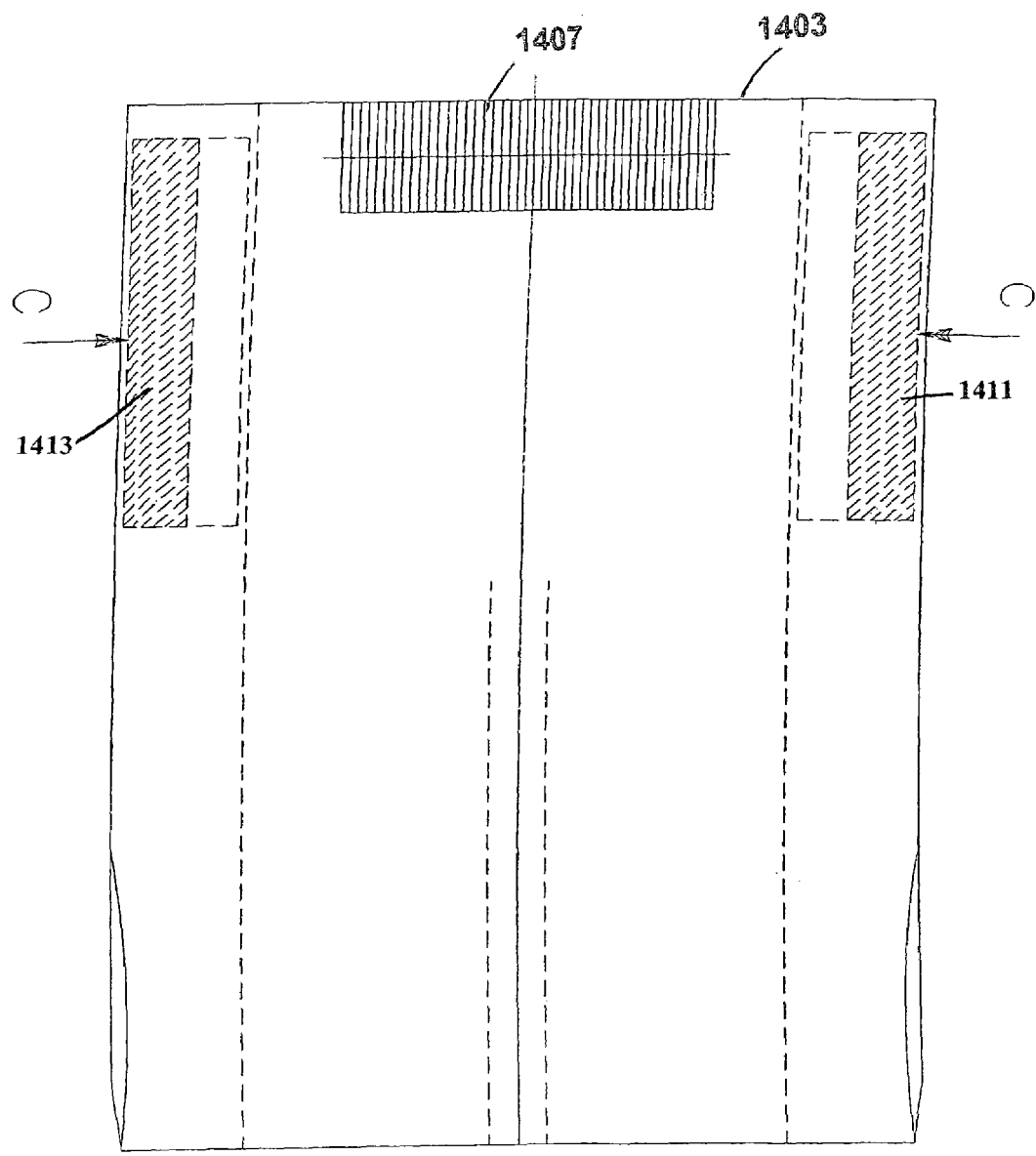
FIG. 31 illustrates the diaper of FIG. 30 in laterally folded position.

FIGS. 31 and 34 show the diaper 1400 of FIG. 30 with the front waist region 1401 folded on the back waist region 1403.

In FIG. 32, the absorbent core 1415 is positioned between the topsheet 1417 and the back sheet 1419 in the usual manner. The backsheet 1419 may be a film or a laminate or film and nonwoven. This film backing 1419 (or laminate backing) is at least as coextensive in width as the absorbent core 1415, however the product sides extend beyond the longitudinal sides of the absorbent core. Also, the backing film lateral width may be less than the nonwoven outer layer.

The absorbent articles shown in FIGS. 1-28A, commonly called pull-up diaper, is manufactured such that the product length is perpendicular to the production machine direction. The absorbent article shown in FIGS. 29-44 are commonly called a diaper or a brief having hooks and loops fastener. Optionally, the diaper backing may act as loops. The method of manufacturing the product shown in FIGS. 29-41 are different from the product shown in FIGS. 1-28A. The width of this product is perpendicular to the machine direction. One object of the present invention is to make the product (FIGS. 29-41) look like and function identical to a pull-up shown in FIGS. 1-28A. This is because products made as in FIGS. 29-41 are simple to manufacture and are less expensive since they require less raw materials.

The nonwoven connectors or wings can be attached on the longitudinal sides of the absorbent product as shown in FIGS. 29-38. The nonwoven connectors can be attached on the back or front surface of the product back waist, or they can be attached between the cover sheet 1417 and the back sheet 1419. The nonwoven connectors can be attached to an area of the product lateral sides or longitudinal sides (FIGS. 29-41) of the absorbent article that is liquid and air permeable or liquid impermeable. For example, the backing 1419 used in FIG. 32 may consist of a nonwoven (outer surface) and a polyethylene sheet (between the absorbent core 1415 and the outer nonwoven). The width of the polyethylene sheet may be narrower than the nonwoven outer layer. In this configuration the nonwoven connectors or wings may be attached to the area of the absorbent article that is only nonwoven in order to be air permeable. The polyethylene layer may have the same width as the nonwoven which makes the area that the nonwoven connectors are attached to air and liquid impermeable. The wings or nonwoven connectors may be air impermeable or air permeable. The nonwoven connectors may be releasably prefolded and the folds kept in place temporarily by hot melt adhesive, by vacuum conveyor or a drum during manufacturing.

The crotch elastics shown in FIG. 29 are in the crotch area of the absorbent article. Optionally, at least one of these elastics may cover the full length of the absorbent article with the exception of the wing 1410, or at least one of the crotch elastics may extend to a portion of the wings 1410 (FIG. 41) and nonwoven connectors 1411 and 1423 (FIG. 30). The absorbent article may have elastic elements in the back and front waist, such as 1405 and 1407 (FIG. 30). If the nonwoven connectors or wings are elastic materials, then the elastic in the back waist area becomes optional.

The absorbent core 1415 (FIG. 32) may be any shape or size and may have any thickness and density. It may be a single pad layer or multi pad layers. The absorbent core is made of fluff (fiberized wood pulp) and super absorbent polymers (SAP) in granular, powder or in wet hydrogel form. It is preferred to use 30 to 70 percent SAP and the rest fluff. Also, it is preferred to have an absorbent article which is without wood pulp fibers, although 5 to 10 percent wood pulp (based on the amount of SAP) improves the absorption rate.

Thus the objective of this invention is to make an absorbent article that would satisfy the users, is easy and economical to mass produce, is discrete, low in cost and effective. Additionally, the product is intended to be as versatile as possible. For example, the product design is such that it can be used (put on or remove/change) as traditional briefs and pull-up under garments, as T-shape articles as described in said copending application Ser. No. 09/376,282 filed Aug. 18, 1999, and one can fasten and refasten the product in a conventional way. For example, the hook type fasteners ends are permanently attached on the back waist and the user fasten or refasten the fasteners on the front waist of the product or he can reverse this operation. The permanently attached portion of the fasteners could be on the front waist and the user or care taker fastens or refastens the fasteners on the back waist. The product may be prefastened so that the user can simply take the product out of the bag or carton and put it on. Or the product can be such that the user must first fasten the product according to instructions on the bags containing the product. The product may also be such that a user is able to remove the product when he has his or hers shoes on.

The invention claimed is:

1. A prefastened absorbent article comprising:
    a top sheet;
    a back sheet;
    an absorbent core sandwiched between the top sheet and the back sheet;
    a back waist portion having an inner surface, an outer surface, a first lateral end and a second lateral end;
    a front waist portion having an inner surface, an outer surface, a first lateral end and a second lateral end;
    a prefolded unitary nonwoven connector having a prefolded first portion, a second portion and a prefolded third portion, the second portion being disposed between the prefolded first portion and the prefolded second portion, the prefolded first and third portions being retained in the prefolded condition by at least one of adhesive and heat seal, the second portion of the prefolded unitary nonwoven connector being attached permanently to the inner surface of the back waist portion so as to cover the full width of the back waist portion from the first lateral end of the back waist portion to the second lateral end of the back waist portion;
    a first hook fastener disposed at an end portion of the prefolded first portion and a second hook fastener disposed at an end portion of the prefolded third portion such that when the absorbent article is folded laterally, the first and second hook fasteners engage one of the inner and outer surfaces of the front waist portion.

2. The prefastened absorbent article of claim 1, wherein the absorbent core is rectangular.

3. The prefastened absorbent article of claim 1, wherein the first, second and third portions of the prefolded unitary nonwoven connector make up three separate pieces that are joined together.

4. The prefastened absorbent article of claim 3, wherein at least 90 percent of the second portion of the prefolded unitary nonwoven connector is non-elastic nonwoven and the first and third portions are made of a single layer elastic nonwoven or a composite of at least two layers at least one of which is a stretchable film.

5. The prefastened absorbent article of claim 1, wherein the prefolded unitary nonwoven connector is breathable.

6. The absorbent article of claim 1, wherein the absorbent core has a first longitudinal end and a second longitudinal end, and at least one of the first and second longitudinal ends of the absorbent core extends under a portion of at least one of the first and second lateral ends of the back waist portion at which the second portion of the prefolded unitary nonwoven connector is attached.

7. The absorbent article of claim 1, wherein the lateral ends of the front and back waist portions are folded at least once inwardly.

8. The absorbent article of claim 1, wherein the second portion of the prefolded unitary nonwoven connector is attached to a portion of the back waist portion that is partially fluid impermeable and partially fluid permeable.

* * * * *

UNITED STATES PATENT AND TRADEMARK OFFICE
CERTIFICATE OF CORRECTION

PATENT NO. : 7,621,901 B2  Page 1 of 1
APPLICATION NO. : 10/646937
DATED : November 24, 2009
INVENTOR(S) : Hamzeh Karami It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 646 days.

Signed and Sealed this

Twenty-sixth Day of October, 2010

David J. Kappos
*Director of the United States Patent and Trademark Office*